United States Patent [19]

Donahoe et al.

[11] Patent Number: 5,538,892
[45] Date of Patent: Jul. 23, 1996

[54] NUCLEIC ACIDS ENCODING A TGF-β TYPE 1 RECEPTOR

[75] Inventors: Patricia K. Donahoe, Weston; Michael Gustafson, Boston, both of Mass.; Wei-Wu He, Columbia, Md.; Xiao-Fan Wang, Durham, N.C.

[73] Assignees: The General Hospital Corporation, Boston, Mass.; Duke University, Durham, N.C.

[21] Appl. No.: 149,105

[22] Filed: Nov. 4, 1993

Related U.S. Application Data

[63] Continuation-in-part of Ser. No. 29,673, Mar. 11, 1993, abandoned, which is a continuation-in-part of Ser. No. 853,396, Mar. 18, 1992, abandoned.

[51] Int. Cl.$^6$ ............ C12N 15/12; C12N 15/79; C12N 5/10; C12N 7/01
[52] U.S. Cl. ............ 435/240.2; 435/320.1; 435/69.1; 435/252.3; 435/254.11; 536/23.5; 536/24.31
[58] Field of Search ............ 536/23.5, 24.31; 435/240.2, 320.1, 69.1, 252.3, 254.11

[56] References Cited

U.S. PATENT DOCUMENTS

| | | | |
|---|---|---|---|
| 4,404,188 | 9/1983 | Donahoe et al. | 424/105 |
| 4,487,833 | 12/1984 | Donahoe et al. | 435/172.2 |
| 4,510,131 | 4/1985 | Donahoe et al. | 424/105 |
| 4,753,794 | 6/1988 | Donahoe | 424/85 |
| 4,792,601 | 12/1988 | Donahoe et al. | 530/387 |
| 5,010,055 | 4/1991 | Donahoe | 514/8 |
| 5,011,687 | 4/1991 | Donahoe et al. | 424/559 |
| 5,047,336 | 9/1991 | Cate et al. | 435/69.4 |

FOREIGN PATENT DOCUMENTS

WO93/19177 9/1993 WIPO.

OTHER PUBLICATIONS

Hei, W. W., et al (1993) Dev. Dyn. 196: 133–42.
Attisano, L., et al. (1993) Cell 75: 671–80.
Ebner et al., Determination of Type I Receptor Specificity by the Type II Receptors of TGFβ or Activin, Science 262:900–901, 1993.
Franzen et al., Cloning of a TGFβ Type I Receptor that Forms a Heteromeric Complex with the TGFβ Type II Receptor, Cell 75:681–692, 1993.
Lopez–Casillas et al., Structure and Expression of the Membrane Proteoglycan Betaglycan, a Component of the TGF–β Receptor System, Cell 67:785–795, 1991.
Moren et al., Molecular Cloning and Characterization of the Human and Porcine Transforming Growth Factor–β Type III Receptors, Biochem. Biophys. Res. Comm. 189:356–362, 1992.
Wang et al., Expression Cloning and Characterization of the TGF–β Type III Receptor, Cell 67:797–805, 1991.

Bassing et al. A Single Heteromeric Receptor Complex Is Sufficient . . . JBC 269, 14861–14864 (1994).
Bassing et al. A Transforming Growth Factor Factor β Type I Receptor . . . Science 263, 87–89 (1994).
Abe et al., High concentrations of Plasma Immunoreactive Inhibin During Normal Pregnancy in Women, J. Clinical Endocrinology and Metablism 71:133–137, 1990.
Au et al., Measurement of Inhibin and an Index of Inhibiin Production by Rat Testes during Postnatal Development, Biology of Reproduction 35:37–43, 1986.
Behringer et al., Abnormal Sexual Development in Transgenic Mice Chronically Expressing Mullerian Inhibiting Substance, Nature 345:167–170, 1990.
Berta et al., Genetic Evidence Equating SRY and the Testis–determining Factor, Nature 348:48–450, 1990.
Bezard et al., Immunocytochemical Study of Anti–Mullerian Hormone in Sheep Ovarian Follicles During Fetal and Post–Natal Development, Reprod. Fert. 90:509–156, 1987.
Blanchard and Josso, Source of the Anti–mullerian Hormone Synthesized by the Fetal Testis: Mullerian–inhibiting Activity of Fetal Bovine Sertoli Cells in Tissue Culture, Pediat. Res. 8:968–971, 1974.
Boyd et al., Transforming Growth Factor–β Inhibition of Epithelial Cell Proliferation Linked to the Expression of a 53–kDa Membrane Receptor, J. Biol. Chem. 264:2272, 1989.
Budzik et al., Enhanced Purification of Mullerian Inhibiting Substance by Lectin Affinity Chromatography, Cell 21:909–916, 1980.
Budzik et al., Mullerian Inhibiting Substance Fractionation by Dye Affinity Chromatography, Cell 34:307–314, 1983.
Burger et al., Serum Inhibin Concentrations Rise Througout Normal Male and Female Puberty, J. Clinical Endocrinology and Metabolism 67:689–694, 1988.
Cate et al., Development of Mullerian Inhibiting Substance as an Anti–cancer Drug, Cold Spring Harbor Symposim 51:641–647, 1986.
Cate et al., Isolation of the Bovine and Human Genes for Mullerian Inhbiting Substance and Expression of the Human Gene in Animal Cells, Cell 45:685–698, 1986.
Catlin et al., Sex–specific Fetal Lung Development and Mullerian Inhibiting Substance, Am. Rev. Respir. Dis. 141:466–470, 1990.
Catlin et al., Mullerian Inhibiting Substance Depresses Accumulation In Vitro of Disaturated Phosphatidyl–choline in Fetal Rat Lung, Am. J. Obstet. Gynecol. 159:1299–303, 1988.

(List continued on next page.)

Primary Examiner—Stephen G. Walsh
Assistant Examiner—David L. Fitzgerald
Attorney, Agent, or Firm—Fish & Richardson

[57] ABSTRACT

Isolated DNAs (e.g., cDNAs or genomic fragments) encoding TGF-β type I receptors, or soluble, ligand-binding fragments thereof; vectors or cells which contain such DNAs; and substantially pure polypeptides encoded by such DNAs, whether produced by expression of the isolated DNAs, by isolation from natural sources, or by chemical synthesis.

21 Claims, 15 Drawing Sheets

OTHER PUBLICATIONS

Chin et al., Human Hullerian Inhibiting Substance Inhibits Tumor Growth In Vitro and In Vivo, Cancer Research, 51:201–2106, 1991.

Cohen–Haguenauer et al., Mapping of the Gene for Anti–Mullerian Hormone to the Short Arm of Human Chromosome 19, Cytogenet. Cell Genet. 44:2–6, 1987.

Coughlin et al., Mullerian Inhibiting Substance Blocks Autophosphorylation of the EGF Receptor by Inhibiting Tyrosine Kinase, Molecular and Cellular Endocrinology 49:75–86, 1987.

de Kretser et al., Serum Inhibin Levels in Normal Men and Men with Testicular Disorders, J. Endocrinology 120:517–523, 1989.

de Kretser et al., The Isolation and Physiology of Inhibin and Related Proteins, Biology of Reproduction 40:33–47, 1989.

Derynck et al., Human Transforming Growth Factor–β Complementary DNA Sequence and Expression in Normal and Transformed Cells, Nature 316:701–705, 1985.

Donahoe et al., Mullerian Duct Regression in the Embryo Correlated Activity Against Human Ovarian Cancer, Science 205:913–915, 1979.

Donahoe et al., Mullerian Inhibiting Substance Inhibits Growth of a Human Ovarian Cancer in Nude Mice, Ovarian Cancer 194:472–480, 1981.

Donahoe et al., Mullerian Inhibiting Substance Activity in Bovine Fetal, Newborn and Prepubertal Testes, Biology of Reproduction 16:238–243, 1977.

Ebner et al., Cloning of a Type I TGF–β Receptor and its Effect on TGF–β Binding to the Type II Receptor, Science 260:1344–1348, 1993.

Epstein et al., Stainless Steel Mesh Supports High Density Cell Growth and Production of Recombinant Mullerian Inhibiting Substances, In Vitro Cellular and Developemental Biology 25:213–216, 1989.

Esch et al., Complementary Deoxyribonucleic Acid (cDNA) Cloning and DNA Sequence Analysis of Rat Ovarian Inhibins, Molecular Endocrinology 1:388–396, 1987.

Forage et al., Cloning and Sequence Analysis of cDNA Species Coding for the Two Subunits of Inhibin form Bovine Follicular Fluid, Proc. Natl. Acad. Sci. USA 83:3091–3095, 1986.

Fuller et al., Mullerian Inhibiting Substance Reduction of Colony Growth of Human Gynecologic Cancers in a Stem Cell Assay, Gynecologic Oncology 22:135–148, 1985.

Fuller et al., Mullerian Inhibiting Substance Inhibition of a Human Endometrial Carcinoma Cell Line Xenografted in Nude Mice, Gynecologic Oncology 17:124–132, 1984.

Fuller et al., Mullerian Inhibiting Substance Inhibits Colony Growth of a Human Ovarian Carcinoma Cell Line, J. Clinical Endocrinology and Metabolism 54:1051–1055, 1982.

Georgi et al., daf–1, a C. elegans Gene Controlling Dauer Larva Development, Encodes a Novel Receptor Protein Kinase, Cell 61:635–645, 1990.

Gubbay et al., A Gene Mapping to the Sex–determining Region of the Mouse Y Chromosome is a Member of a Novel Family of Embryonically Expressed Genes, Nature 346:245–250, 1990.

Gustafson et al., Mullerian Inhibiting Substance as a Marker for Ovarian Sex–Cord Tumor, New England Journal of Medicine 326:466–471, 1992.

Hanks et al., The Protein Kinase Family: Conserved Features and Deduced Phylogeny of the Catalytic Domains, Science 241:42–52, 1988.

Haqq et al., Isolation of the Rat Gene for Mullerian Inhibiting Substance, Geomics 12:665–669, 1992.

Hasegawa et al., Changes in Serum Concentrations of Immunoreactive Inhibin During the Oestrous Cycle of the Rat, J. Endocrinology 121:91–100, 1989.

Hsueh et al., Heterodimers and Homodimers of Inhibin Subunits have Different Paracrine Action in the . . . of Luteinizing Hormone–Stimulated Androgen Biosynthesis Proc. Natl. Acad. Sci. USA 84:5082–5086, 1987.

Hudson et al., An Immunoassay to Detect Human Mullerian Inhihbiting Substance in Males and Females During Normal Development, J. Clinical Endocrinology and Metabolism 70:16–22, 1990.

Hutson and Donahoe, The Hormonal Control of Testicular Descent, Endocrine Reviews 7:270–283, 1986.

Josso et al., An Enzyme Linked Immunoassay for Anti–Mullerian Hormone: A New Tool for the Evaluation of Testicular Function in Infants and children, J. Clinical Endocrinology and Metabolism 70:23–27, 1990.

King et al., Mapping Anti–Mullerian Hormone (Amh) and Related Sequences in the Mouse: Identification of a New Region of Homology Between MMU10 and HSA19p, Genomics 11:273–283, 1991.

Knebelmann et al., Anti–Mullerian Hormone Bruxelles: A Nonsense Mutuation Associated with the Persistent Mullerian Duct Syndrome, Proc. Natl. Acad. Sci. USA 88:3767–3771, 1991.

Lappohn et al., Inhibin as a Marker for Granulosa–Cell Tumors, New England Journal of Medicine 321:790–793, 1989.

Laiho et al., Concomitant Loss of Transforming Growth Factor (TGF)–β Types I and II in TGF–β–. . . Mutants Implicates Both Receptor Types in Signal Transduction, J. Biol. Chem. 265:18518–18524, 1990.

Lin et al., Expression Cloning of the TGF–β Type II Receptor, a Functional Transmembrane Serine/Threonine Kinase, Cell 68:775–785, 1992.

Ling et al., Pituitary FSH is Released by a Heterodimer of the β–subunits from the Two Forms of Inhibin, Nature 321:779–782, 1986.

Lopez–Cusillas et al., Betaglycan Presents Ligand to the TGFβ Signaling Receptor, Cell 73:1435–1444, 1993.

MacLaughlin et al., Bioassay, Purification, Cloning, and Expression of Mullerian Inhibiting Substance, Methods in Enzymology 198:358–369, 1991.

Mason et al., Complementary DNA Sequences of Ovarian Follicular Fluid Inhibin Show Precursor Structure and Homology with Transforming Growth Factor–β, Nature 318:659–663, 1985.

Mason et al., Structure of Two Human Ovarian Inhibins, Biochemical and Biophysical Research Communications, 135:957–964, 1986.

Massague, The Transforming Growth Factor–β Family, Annu. Rev. Cell Biol. 6:597–641, 1990.

Mathews and Vale, Expression Cloning of an Activin Receptor, a Predicted Transmembrane Serine Kinase, Cell 65:973–982, 1991.

Mayo et al., Inhibin A–subunit cDNAs from Porcine Ovary and Human Placenta, Proc. Natl. Acad. Sci. USA 83:5849–5853, 1986.

McCullagh, Dual Endocrine Activity of the Testes, Science 70:19–20, 1932.

McLachlan et al., The Radioimmunoassay of Bovine and Human Follicular Fluid and Serum Inhibin, Molecular and Cellular Endocrinology 46:175–185, 1986.

McLachlan et al., Relative Roles of Follicle–stimulating Hormone and Luteinizing Hormone in the Conrol of Inhibin Secretion in Normal Men, J. Clin, Invest. 82:880–884, 1988.

McLachlan et al., Circulating Immunoreactive Inhibin Levels During the Normal Human Menstrual Cycle, J. Clinical Endocrinology and Metabolism 65:954–961, 1987.Meunier et al., Gonadal and Extragonadal Expression of Inhibin α, βA, and βB Subunits in Various Tissues Predicts Diverse Functions, Proc. Natl. Acad. Sci. USA 85:247–251, 1988.

Miyamoto et al., Demonstration of High Molecular Weight Forms of Inhibin in Bovine Follicular Fluid (bFF) by Using Monoclonal Antibodies to bFF 32K Inhibin, Biochem. and Biophys. Res. Commun. 136:1103–1109, 1986.

Munsterberg and Lovell–Badge, Expression of the Mouse Anti–Mullerian Hormone Gene Suggests a Role in Both Male and Female Sexual Differentiation, Development 113:613–624, 1991.

Padgett et al., A Transcript from a *Drosophila* Pattern Gene Predicts Homologous to the Transforming Growth Factor–β Family, Nature 325:81–84, 1987.

Petraglia et al., Localization, Secretion, and Action of Inhibin in Human Placenta, Science 237:187–189, 1987.

Picard and Josso, Purification of Testicular Anti–Mullerian Hormone Allowing Direct Visualization of the . . . Determination of Yield and Purification Factor, Molecular and Cellular Endocrinology 34:23–29, 1984.

Ranges et al., Inhibition of Cytotoxic T Cell Development by Transforming Growth Factor β and Reversal by Recombinant Tumor Necrosis Factor α, J. Exp. Med. 166:991–998, 1987.

Rook et al., Effects of Transforming Growth Factor βon the Functions of Natural Killer Cells: Depressed Cytolytic Activity and Blunting of Interferon Responsiveness, J. Immunology 136:3916–3920, 1986.

Schneyer et al., Immunoreactive Inhibin α–Subunit in Human Serum: Implications for Radioimmunoassay, J. Clinical Endocrinology and Metabolism 70:1208–1212, 1990.

Sheckter et al., Stimulation of Serum Inhibin Concentrations by Gonadotropin–Releasing Hormone in Men with Idiopathic Hypogonadotropic Hypogonadism, J. Clinical Endocrinology and Metabolism 67:1221–1224, 1988.

Sinclair et al., A Gene from the Human Sex–determining Region Encodes a Protein with Homology to a Conserved DNA–binding Motif, Nature 346:240–244, 1990.

Takahashi et al., Mullerian Inhibiting Substance as Oocyte Meiosis Inhibitor, Molecular and Cellular Endocrinology 47:225–234, 1986.

Takahashi et al., The Ontogeny of Mullerian Inhibiting Substance in Granulosa Cells of the Bovine Ovarian Follicle, Biology of Reproduction 35:447–453, 1986.

Taketo et al., Delay of Testicular Differentiation in the $B6.Y^{DMO}$ Ovotestis Demonstrated by Immunocyto–chemical Staining for Mullerian Inhibiting Substance, Developmental Biology 146:386–395, 1991.

Ueno et al., Cellular Localization of Mullerian Inhibiting Substance in the Developing Rat Ovary, Endocrinology 124:1000–1006, 1989.

Ueno et al., Human Recombinant Mullerian Inhibiting Substance Inhibition of Rat Oocyte Meiosis is Reversed by Epidermal Growth Factor In Vitro, Endocrinology 123:1652–1659, 1988.

Ueno et al., Mullerian Inhibiting Substance in the Adult Rat Ovary During Various Stages of the Estrous Cycle, Endocrinology 125:1060–1066, 1989.

Vale et al., Chemical and Biological Characterization of the Inhibin Family of Protein Hormones, Recent Progress in Hormone Research, 44:1–34, 1988.

Vale et al., Purification and Characterization of an FSH Releasing Protein From Porcine Ovarian Follicular Fluid Nature 321:776–779, 1986.

Vigier et al., Anti–Mullerian Hormone Produces Endocrine Sex Reversal of Fetal Ovaries, Proc. Natl. Acad. Sci. USA 86:3684–3688, 1989.

Vigier et al., Purified Bovine AMH Induces a Characteristic Freemartin Effect in Fetal Rat Prospective Ovaries Exposed to it In Vitro, Development 100:43–45, 1987.

Weeks and Melton, A Maternal mRNA Localized to the Vegetal Hemisphere in Xenopus Eggs Codes for a Growth Factor Related to TGF–β, Cell 51:861–867, 1987.

Woodruff et al., Inhibin and Activin Locally Regulate Rat Ovarian Folliculogenesis, Endocrinology 127:3196–3205, 1990.

Woodruff et al., Dynamic Changes in Inhibin Messenger RNAs in Rat Ovarian Follicles During the Reproductive Cycle, Science 239:1296–1299, 1988.

Wozney et al., Novel Regulators of Bone Formation: Molecular Clones and Activities, Science 242:1528–1534, 1988.

Wrana et al., TGFβ Signals Through a Heteromeric Protein Kinase Receptor Complex, Cell 71:1003–1014, 1992.

```
        560                   580                    600
atggtcgatggagcaatgatcctttctgtgctaatgatgatggctctccttccccgagt
MetValAspGlyAlaMetIleLeuSerValLeuMetMetMetAlaLeuProSerProSer
        620                   640                    660
atggaagatgaggagcccaaggtcaacccgaagctttacatgtgtgtgtgtgagggcctc
MetGluAspGluGluProLysValAsnProLysLeuTyrMetCysValCysGluGlyLeu
        680                   700                    720
tcctgcgggaacgaggaccactgtgagggccagcagtgttttcctccctgagcgtcaat
SerCysGlyAsnGluAspHisCysGluGlyGlnGlnCysPheSerSerLeuSerValAsn
        740                   760                    780
gatggcttccgcgtctaccagaagggctgctttcaggtctatgagcaggggaagatgacg
AspGlyPheArgValTyrGlnLysGlyCysPheGlnValTyrGluGlnGlyLysMetThr
        800                   820                    840
tgtaagacccccgccgtcgcctggccaggctgtggagtgctgccaaggggactggtgcaac
CysLysThrProProSerProGlyGlnAlaValGluCysCysGlnGlyAspTrpCysAsn
        860                   880                    900
aggaacgtcacggcccggctgcccactaaagggaaatccttccctggatcgcagaacttc
ArgAsnValThrAlaArgLeuProThrLysGlyLysSerPheProGlySerGlnAsnPhe
        920                   940                    960
cacctggaagttggccttatcatcctctccgtggtgtttgcggtatgccttttcgcttgc
HisLeuGluValGlyLeuIleIleLeuSerValValPheAlaValCysLeuPheAlaCys
        980                   1000                   1020
atccttggcgttgctctcaggaagtttaaaaggcgcaatcaagagcgcctgaaccccaga
IleLeuGlyValAlaLeuArgLysPheLysArgArgAsnGlnGluArgLeuAsnProArg
        1040                  1060                   1080
gacgtggagtacggtactatcgaagggctcatcaccaccaacgtcggagatagcactcta
AspValGluTyrGlyThrIleGluGlyLeuIleThrThrAsnValGlyAspSerThrLeu
        1100                  1120                   1140
gcggaattactagatcactcgtgtacatcaggaagtggctccggtcttcctttttctggta
AlaGluLeuLeuAspHisSerCysThrSerGlySerGlySerGlyLeuProPheLeuVal
        1160                  1180                   1200
cagagaactgtggctcgacagataaccctgttggagtgtgtcgggaagggccggtatgga
GlnArgThrValAlaArgGlnIleThrLeuLeuGluCysValGlyLysGlyArgTyrGly
        1220                  1240                   1260
gaagtgtggagggggcagctggcaaggcgaaaatgttgctgtgaagatcttctcctcccgt
GluValTrpArgGlySerTrpGlnGlyGluAsnValAlaValLysIlePheSerSerArg
        1280                  1300                   1320
gatgagaagtcgtggttcagggagacagaattgtacaacacggtgatgctgaggcatgag
AspGluLysSerTrpPheArgGluThrGluLeuTyrAsnThrValMetLeuArgHisGlu
        1340                  1360                   1380
aatatcttaggtttcattgcttcagacatgacctctagacactccagtacccagctgtgg
AsnIleLeuGlyPheIleAlaSerAspMetThrSerArgHisSerSerThrGlnLeuTrp
        1400                  1420                   1440
ctcattacacattaccacgaaatgggatcgttgtatgactaccttcagctcaccactctg
LeuIleThrHisTyrHisGluMetGlySerLeuTyrAspTyrLeuGlnLeuThrThrLeu
        1460                  1480                   1500
gacacggttagctgccttcggatcgtgttgtccatagccagcggccttgcacacttgcac
AspThrValSerCysLeuArgIleValLeuSerIleAlaSerGlyLeuAlaHisLeuHis
```

FIG. 1a

```
                    1520                1540                1560
atagagatatttgggacccaggggaagtctgccatcgcccaccgagatctaaagagcaaa
IleGluIlePheGlyThrGlnGlyLysSerAlaIleAlaHisArgAspLeuLysSerLys
                    1580                1600                1620
aacatcctcgtgaagaagaacggacagtgctgcatagcagatttgggcctggcagtcatg
AsnIleLeuValLysLysAsnGlyGlnCysCysIleAlaAspLeuGlyLeuAlaValMet
                    1640                1660                1680
cattcccagagcacgaatcagcttgatgtgggaaacaaccccgtgtggggaccaagcgc
HisSerGlnSerThrAsnGlnLeuAspValGlyAsnAsnProArgValGlyThrLysArg
                    1700                1720                1740
tacatggcccctgaagtgcttgatgaaaccatccaagtggattgctttgattcttataag
TyrMetAlaProGluValLeuAspGluThrIleGlnValAspCysPheAspSerTyrLys
                    1760                1780                1800
agggtcgatatttgggcctttggcctcgttctgtgggaagtggccaggaggatggtgagc
ArgValAspIleTrpAlaPheGlyLeuValLeuTrpGluValAlaArgArgMetValSer
                    1820                1840                1860
aatggtatagtggaagattacaagccaccattctatgatgttgttcccaatgacccaagt
AsnGlyIleValGluAspTyrLysProProPheTyrAspValValProAsnAspProSer
                    1880                1900                1920
tttgaagatatgaggaaagttgtctgtgtggatcaacagaggccaaacatacctaacaga
PheGluAspMetArgLysValValCysValAspGlnGlnArgProAsnIleProAsnArg
                    1940                1960                1980
tggttctcagacccgacattaacttctctggcgaagctgatgaaagaatgctggtaccag
TrpPheSerAspProThrLeuThrSerLeuAlaLysLeuMetLysGluCysTrpTyrGln
                    2000                2020                2040
aacccatccgccagactcacagctctacgtatcaaaaagactttgaccaaaattgataac
AsnProSerAlaArgLeuThrAlaLeuArgIleLysLysThrLeuThrLysIleAspAsn
                    2060
tccctagacaaattaaaaactgactgttga
SerLeuAspLysLeuLysThrAspCysEnd
```

FIG. 1b

```
         10                  30                  50
atggcggagtcggccggagcctcctccttcttcccccttgttgtcctcctgctcgccggc
MetAlaGluSerAlaGlyAlaSerSerPhePheProLeuValValLeuLeuLeuAlaGly
         70                  90                 110
agtggcgggtccgggccccgggggatccaggctctgctgtgtgcatgcaccagctgccta
SerGlyGlySerGlyProArgGlyIleGlnAlaLeuLeuCysAlaCysThrSerCysLeu
        130                 150                 170
cagaccaactacacctgcgaaacagatggggcctgcatggtctccatctttaacctggat
GlnThrAsnTyrThrCysGluThrAspGlyAlaCysMetValSerIlePheAsnLeuAsp
        190                 210                 230
ggcatggagcaccacgtacgcacctgcatccccaaggtggagcttgtgcctgctgggaag
GlyMetGluHisHisValArgThrCysIleProLysValGluLeuValProAlaGlyLys
        250                 270                 290
cccttctactgcctgagttcagaggacctgcgcaacacgcactgctgctatattgacttc
ProPheTyrCysLeuSerSerGluAspLeuArgAsnThrHisCysCysTyrIleAspPhe
        310                 330                 350
tgcaacaagattgacctgagggtgcccagtggacacctcaaggagcctgagcacccctcc
CysAsnLysIleAspLeuArgValProSerGlyHisLeuLysGluProGluHisProSer
        370                 390                 410
atgtggggccctgtggagctggtcggcatcattgccggtcctgtcttcctcctcttcctc
MetTrpGlyProValGluLeuValGlyIleIleAlaGlyProValPheLeuLeuPheLeu
        430                 450                 470
atcatcatcatcgtcttcctggtcatcaactatcatcagcgtgtctaccacaaccgccaa
IleIleIleIleValPheLeuValIleAsnTyrHisGlnArgValTyrHisAsnArgGln
        490                 510                 530
agactggacatggaggaccccctcatgtgagatgtgtctctccaaagacaagacgctccag
ArgLeuAspMetGluAspProSerCysGluMetCysLeuSerLysAspLysThrLeuGln
        550                 570                 590
gatctcgtctacgatctctccacttcaggatcgggctcagggttaccccttttgtccag
AspLeuValTyrAspLeuSerThrSerGlySerGlySerGlyLeuProLeuPheValGln
        610                 630                 650
cgcacagtggcccgaaccattgttttacaagagattatcggcaagggccggtttggggaa
ArgThrValAlaArgThrIleValLeuGlnGluIleIleGlyLysGlyArgPheGlyGlu
        670                 690                 710
gtatggcgtggccgctggaggggtggtgatgtggctgtgaaaatcttctcttcccgtgaa
ValTrpArgGlyArgTrpArgGlyGlyAspValAlaValLysIlePheSerSerArgGlu
        730                 750                 770
gagcggtcgtggttccgggaggcagagatctaccagactgtcatgctgcgccatgaaaac
GluArgSerTrpPheArgGluAlaGluIleTyrGlnThrValMetLeuArgHisGluAsn
        790                 810                 830
atccttgggtttattgctgctgacaataaagacaatggcacctggacccagctgtggctt
IleLeuGlyPheIleAlaAlaAspAsnLysAspAsnGlyThrTrpThrGlnLeuTrpLeu
        850                 870                 890
gtctctgactatcacgagcacggctcactgttcgattatctgaaccgctacacagtgacc
ValSerAspTyrHisGluHisGlySerLeuPheAspTyrLeuAsnArgTyrThrValThr
        910                 930                 950
attgaggggatgattaaactggccctgtctgcagccagtggtttggcacacctgcatatg
IleGluGlyMetIleLysLeuAlaLeuSerAlaAlaSerGlyLeuAlaHisLeuHisMet
```

FIG. 2a

```
                970                990                1010
     gagattgtgggcactcaggggaagcctggaattgctcatcgagacttgaagtcaaagaac
     GluIleValGlyThrGlnGlyLysProGlyIleAlaHisArgAspLeuLysSerLysAsn
                1030               1050               1070
     attctggtgaagaagaatggcatgtgtgccattgcagacctgggcctagctgtccgtcac
     IleLeuValLysLysAsnGlyMetCysAlaIleAlaAspLeuGlyLeuAlaValArgHis
                1090               1110               1130
     gatgctgtcactgacaccatagacattgctccaaatcagagggtgggaaccaaacgatac
     AspAlaValThrAspThrIleAspIleAlaProAsnGlnArgValGlyThrLysArgTyr 1150               1170               1190
     atggctcctgaagtacttgacgagaccatcaacatgaagcactttgactccttcaagtgt
     MetAlaProGluValLeuAspGluThrIleAsnMetLysHisPheAspSerPheLysCys
                1210               1230               1250
     gccgatatctacgccctcgggcttgtctattgggagattgctcggaggtgcaattctgga
     AlaAspIleTyrAlaLeuGlyLeuValTyrTrpGluIleAlaArgArgCysAsnSerGly
                1270               1290               1310
     ggagtccatgaagagtatcaactgccatattatgatttagtgccctctgacccttccatt
     GlyValHisGluGluTyrGlnLeuProTyrTyrAspLeuValProSerAspProSerIle
                1330               1350               1370
     gaggaaatgcgaaaggtcgtctgtgaccagaagctacggcccaatgtccccaactggtgg
     GluGluMetArgLysValValCysAspGlnLysLeuArgProAsnValProAsnTrpTrp
                1390               1410               1430
     cagagttatgaggccttgcgagtgatggggaagatgatgcgggagtgctggtacgccaat
     GlnSerTyrGluAlaLeuArgValMetGlyLysMetMetArgGluCysTrpTyrAlaAsn
                1450               1470               1490
     ggtgctgcccgcctgacagcgctgcgcatcaagaagactttgtcccagctaagcgtgcag
     GlyAlaAlaArgLeuThrAlaLeuArgIleLysLysThrLeuSerGlnLeuSerValGln
                1510
     gaagacgtgaagatttaa
     GluAspValLysIleEnd
```

FIG. 2b

```
              270                    290                      310
atgaccctggggattttttcgaagggtctttttgatgctgtcggtggccttgggcctaact
MetThrLeuGlyIlePheArgArgValPheLeuMetLeuSerValAlaLeuGlyLeuThr
              330                    350                      370
aagggagacttggtgaagccctccagggggtcagctggtaaactgcacttgtgagaaccca
LysGlyAspLeuValLysProSerArgGlyGlnLeuValAsnCysThrCysGluAsnPro
              390                    410                      430
cactgcaagaggccaatctgccaggggggcatggtgcacagtggtgctagttcgagagcag
HisCysLysArgProIleCysGlnGlyAlaTrpCysThrValValLeuValArgGluGln
              450                    470                      490
ggcaggcacccccaggtctatcggggctgcgggagcctgaaccaggagctctgcctggga
GlyArgHisProGlnValTyrArgGlyCysGlySerLeuAsnGlnGluLeuCysLeuGly
              510                    530                      550
cgtcccacggagtttgtgaaccatcactgctgctatagatccttctgcaaccacaatgtg
ArgProThrGluPheValAsnHisHisCysCysTyrArgSerPheCysAsnHisAsnVal
              570                    590                      610
tccctgatgctggaggccacccaaactccttcggaggagccagaagtagatgcccatctg
SerLeuMetLeuGluAlaThrGlnThrProSerGluGluProGluValAspAlaHisLeu
              630                    650                      670
cctctgatcctgggtcccgtgctggccttgctggtcctggtggccctgggcactctgggc
ProLeuIleLeuGlyProValLeuAlaLeuLeuValLeuValAlaLeuGlyThrLeuGly
              690                    710                      730
ttgtggcgtgtccggagaaggcaggagaagcagcggggtctgcacagtgacctgggcgag
LeuTrpArgValArgArgArgGlnGluLysGlnArgGlyLeuHisSerAspLeuGlyGlu
              750                    770                      790
tccagtctcatcctgaaggcatcggaacagggagacagcatgttgggggacttcctggtc
SerSerLeuIleLeuLysAlaSerGluGlnGlyAspSerMetLeuGlyAspPheLeuVal
              810                    830                      850
agcgactgtaccacaggcagcggctcagggctaccctttcttggtgcagaggacagtagcg
SerAspCysThrThrGlySerGlySerGlyLeuProPheLeuValGlnArgThrValAla
              870                    890                      910
cgacaggttgcactggtggagtgtgtgggaaagggccgatatggcgaggtgtggcgcggt
ArgGlnValAlaLeuValGluCysValGlyLysGlyArgTyrGlyGluValTrpArgGly
              930                    950                      970
tcgtggcatggcgagagtgtggcggtcaagattttctcctcacgagatgagcagtcctgg
SerTrpHisGlyGluSerValAlaValLysIlePheSerSerArgAspGluGlnSerTrp
              990                    1010                     1030
ttccgggagacagagatctacaacacagttctgcttagacacgacaacatcctaggcttc
PheArgGluThrGluIleTyrAsnThrValLeuLeuArgHisAspAsnIleLeuGlyPhe
              1050                   1070                     1090
atcgcctccgacatgacctcgcggaactccagcacgcagctgtggcttatcacccactac
IleAlaSerAspMetThrSerArgAsnSerSerThrGlnLeuTrpLeuIleThrHisTyr
              1110                   1130                     1150
cacgagcatggctccctctatgactttctgcagaggcagacgctggagccccagttggcc
HisGluHisGlySerLeuTyrAspPheLeuGlnArgGlnThrLeuGluProGlnLeuAla
```

FIG. 3a

```
          1170              1190              1210
ctgaggctggctgtgtccgcggcctgcgctggcctggcgcacctgcatgtagagatcttt
LeuArgLeuAlaValSerAlaAlaCysAlaGlyLeuAlaHisLeuHisValGluIlePhe
          1230              1250              1270
ggcactcaaggcaaaccagccatcgcccatcgtgacctcaagagccgcaacgtgctggtc
GlyThrGlnGlyLysProAlaIleAlaHisArgAspLeuLysSerArgAsnValLeuVal
          1290              1310              1330
aagagcaacttgcagtgttgcattgcagacctgggattggctgtgatgcactcgcaaagc
LysSerAsnLeuGlnCysCysIleAlaAspLeuGlyLeuAlaValMetHisSerGlnSer
          1350              1370              1390
agcgattacctggacattggtaacaaccccgagtgggtaccaagagatacatggcaccc
SerAspTyrLeuAspIleGlyAsnAsnProArgValGlyThrLysArgTyrMetAlaPro
          1410              1430              1450
gaggtgctggatgagcagatccgcacagactgttttgagtcgtacaagtggacagacatc
GluValLeuAspGluGlnIleArgThrAspCysPheGluSerTyrLysTrpThrAspIle
          1470              1490              1510
tgggccttcggcttagtgctatgggagattgcccggcggaccatcatcaatggcattgtg
TrpAlaPheGlyLeuValLeuTrpGluIleAlaArgArgThrIleIleAsnGlyIleVal
          1530              1550              1570
gaggactacaggccacccttctatgacatggtacccaatgaccccagttttgaggacatg
GluAspTyrArgProProPheTyrAspMetValProAsnAspProSerPheGluAspMet
          1590              1610              1630
aaaaaggtggtgtgtgttgaccagcagaccccaccatccctaaccgactggcagcagat
LysLysValValCysValAspGlnGlnThrProThrIleProAsnArgLeuAlaAlaAsp
          1650              1670              1690
ccggtcctctccgggctggcccagatgatgcgagagtgctggtaccccaaccccctccgct
ProValLeuSerGlyLeuAlaGlnMetMetArgGluCysTrpTyrProAsnProSerAla
          1710              1730              1750
cgcctcaccgcactgcgcataaagaagacattacagaagctcagccagaatccagagaaa
ArgLeuThrAlaLeuArgIleLysLysThrLeuGlnLysLeuSerGlnAsnProGluLys
          1770
cccaaagtgattcactag
ProLysValIleHisEnd
```

FIG. 3b

```
                    60                    80                      10
atggaggcggcgtcggctgctttgcgtcgctgcctgcttctcatcgtgttggtggcggcg
MetGluAlaAlaSerAlaAlaLeuArgArgCysLeuLeuLeuIleValLeuValAlaAla
0                  120                   140                     16
gcgacgctgctcccgggggcgaaggcattacagtgtttctgccacctctgtacaaaggac
AlaThrLeuLeuProGlyAlaLysAlaLeuGlnCysPheCysHisLeuCysThrLysAsp
0                  180                   200                     22
aattttacttgtgagacagatggtctctgctttgtctcagtcaccgagaccacagacaaa
AsnPheThrCysGluThrAspGlyLeuCysPheValSerValThrGluThrThrAspLys
0                  240                   260                     28
gttatacacaatagcatgtgtatagctgaaatcgacctaattccccgagacaggccattt
ValIleHisAsnSerMetCysIleAlaGluIleAspLeuIleProArgAspArgProPhe
0                  300                   320                     34
gtttgtgcaccatcttcaaaaacaggggcagttacgtattgctgcaatcaggatcactgc
ValCysAlaProSerSerLysThrGlyAlaValThrTyrCysCysAsnGlnAspHisCys
0                  360                   380                     40
aataaaatagaactcccaactacaggaccttttcagaaaagcagtcagctggcctcggt
AsnLysIleGluLeuProThrThrGlyProPheSerGluLysGlnSerAlaGlyLeuGly
0                  420                   440                     46
cctgtggagctggcagctgtcattgctggtccagtctgcttcgtctgcattgcacttatg
ProValGluLeuAlaAlaValIleAlaGlyProValCysPheValCysIleAlaLeuMet
0                  480                   500                     52
ctgatggtctatatctgccataaccgcactgtcattcaccacgcgtgccaaatgaagag
LeuMetValTyrIleCysHisAsnArgThrValIleHisHisArgValProAsnGluGlu
0                  540                   560                     58
gatccctcactagatcgccctttcatttcagagggcaccaccttaaaagatttaatttat
AspProSerLeuAspArgProPheIleSerGluGlyThrThrLeuLysAspLeuIleTyr
0                  600                   620                     64
gatatgacaacatcagggtctggatcaggtttaccactgcttgttcaaagaacaattgca
AspMetThrThrSerGlySerGlySerGlyLeuProLeuLeuValGlnArgThrIleAla
0                  660                   680                     70
aggaccattgtgctacaagaaagcatcggcaaaggtcggtttggagaagtttggcgaggc
ArgThrIleValLeuGlnGluSerIleGlyLysGlyArgPheGlyGluValTrpArgGly
0                  720                   740                     76
aaatggcggggagaagaagttgccgtgaagataTTCTCTTCTAGAGAAGAACGTTCATGG
LysTrpArgGlyGluGluValAlaValLysIlePheSerSerArgGluGluArgSerTrp
0                  780                   800                     82
TTCCGAGAGGCAGAGATTTATCAGACTGTAATGTTACGCCATGAAAATATCCTGGGGTTT
PheArgGluAlaGluIleTyrGlnThrValMetLeuArgHisGluAsnIleLeuGlyPhe
0                  840                   860                     88
ATAGCAGCAGACAACAAAGACAATGGTACATGgactcagctgtggttggtgtcggattat
IleAlaAlaAspAsnLysAspAsnGlyThrTrpThrGlnLeuTrpLeuValSerAspTyr
0                  900                   920                     94
catgagcatggatcccttttcgattacttgaatagatacactgttactgtggaaggaatg
HisGluHisGlySerLeuPheAspTyrLeuAsnArgTyrThrValThrValGluGlyMet
```

FIG. 4a

```
     0                960               980              100
atcaaactcgctctgtccacggcaagtggtcttgcccatcttcacatggagattgttggt
IleLysLeuAlaLeuSerThrAlaSerGlyLeuAlaHisLeuHisMetGluIleValGly
     0               1020              1040              106
acccaaggaaaaccagctattgccCATAGAGATTTGAAATCAAAGAATATCTTGGTGAAG
ThrGlnGlyLysProAlaIleAlaHisArgAspLeuLysSerLysAsnIleLeuValLys
     0               1080              1100              112
AAAAATGGAACCTGTTGTATTGCAGATTTGGGACTTGCTGTGAGACATGATTCTGCCACA
LysAsnGlyThrCysCysIleAlaAspLeuGlyLeuAlaValArgHisAspSerAlaThr
     0               1140              1160              118
GATACAATTGATATTGCTCCAAACCACAGAGTAGGCACTAAAAGGtatatggcccctgaa
AspThrIleAspIleAlaProAsnHisArgValGlyThrLysArgTyrMetAlaProGlu
     0               1200              1220              124
gttctagatgattccataaatatgaaacattttgaatccttcaaacgtgctgacatctat
ValLeuAspAspSerIleAsnMetLysHisPheGluSerPheLysArgAlaAspIleTyr
     0               1260              1280              130
gcaatgggcttagtattctgggaaatcgctcgacgctgttccattggcggaatccacgaa
AlaMetGlyLeuValPheTrpGluIleAlaArgArgCysSerIleGlyGlyIleHisGlu
     0               1320              1340              136
gactaccagttgccttactatgatcttgtaccttctgatccatccgttgaagaaatgaga
AspTyrGlnLeuProTyrTyrAspLeuValProSerAspProSerValGluGluMetArg
     0               1380              1400              142
aaagtagtttgtgaacagaagttaaggccaaatattcccaacagatggcagagctgtgag
LysValValCysGluGlnLysLeuArgProAsnIleProAsnArgTrpGlnSerCysGlu
     0               1440              1460              148
gccttgagagtgatggccaaaattatgagagaatgttggtatgccaatggagcagctagg
AlaLeuArgValMetAlaLysIleMetArgGluCysTrpTyrAlaAsnGlyAlaAlaArg
     0               1500              1520              154
ctgacagctttgcgaattaaaaaaacattgtcacagctcagccaacaggaaggcatcaaa
LeuThrAlaLeuArgIleLysLysThrLeuSerGlnLeuSerGlnGlnGluGlyIleLys
     0
atgtaa
MetEnd
```

FIG. 4b

FIG. 5a MISr1 (BCORI insert size ~2.7 kb, specific oligo sequence: 5'-GTCTACCAGAAGGGCTGCTT-3') (SEQ ID NO: 5) All inserts are in the ECORI site of plasmid pBluescript I SK(-).

FIG. 5b MISr2a (~1.4 kb, 5'-CCGGAGCCTCCTCCTTCTTC-3') (SEQ ID NO: 6)

FIG. 5c MISr2b (~2.1 kb, 5'-TCCCTACTGGGTTGAGACA-3') (SEQ ID NO: 7)

FIG. 5d MISr3 (~3.2 kb, 5'-GCTGCGGGAGCCTGAACCAG-3') (SEQ ID NO: 8)

FIG. 5e MISr4 (~2.8 kb, 5'-AAATCCAATGTTGAATACT-3') (SEQ ID NO: 9)

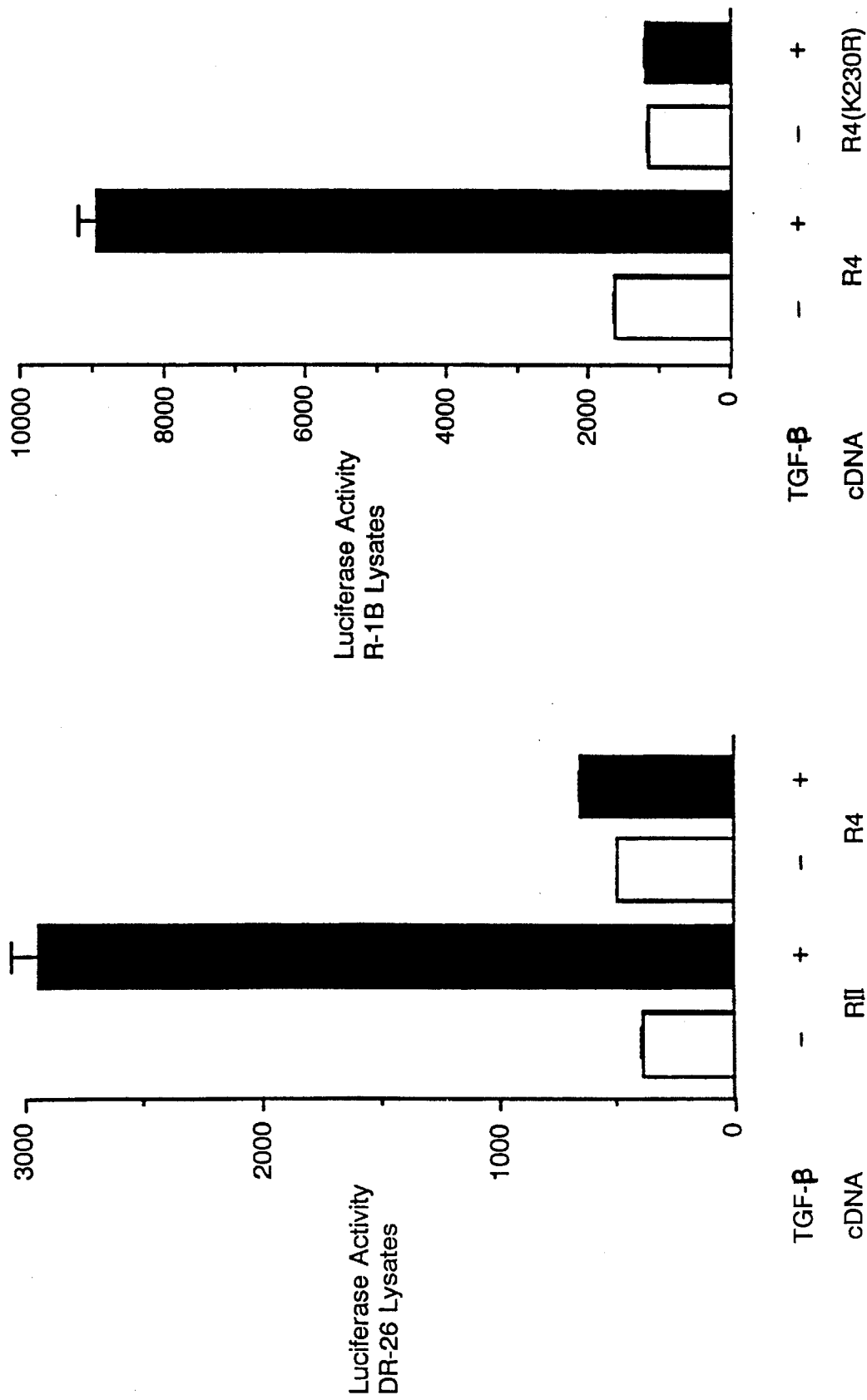

NUCLEIC ACIDS ENCODING A TGF-β TYPE 1 RECEPTOR

The work described herein was supported in part by grant No. Ca17393 from the National Institutes of Health. The U.S. government has certain rights in the invention.

This application is a continuation-in-part of Donahoe et al., U.S. Ser. No. 08/029,673, filed Mar. 11, 1993, now abandoned, which in turn is a continuation-in-part of Donahoe et al., U.S. Ser. No. 07/853,396, filed Mar. 18, 1992, now abandoned, each of which applications is herein incorporated by reference.

BACKGROUND OF THE INVENTION

The field of the invention is mammalian receptor proteins, and nucleic acids encoding same.

The transforming growth factor betas (TGF-βs) are a family of multifunctional peptide hormones that play important roles in many aspects of cellular function. TGF-β can inhibit the differentiation of certain mesodermal cells, induce differentiation of others, and inhibit proliferation of cells derived from epithelial, endothelial, neuronal, hematopoietic, lymphoid, and fibroblastic origins (Roberts and Sporn, in *Peptide Growth Factors and Their Receptors*, Sporn and Roberts, Eds., Springer-Verlag, Heidelberg, Germany, 1990, pp. 421–427; Massague, Annu. Rev. Cell Biol. 6:597, 1990). In addition to its effects on individual cells, TGF-β is also important in many biological processes (Roberts and Sporn, supra). For example, TGF-β is an important regulator of immune responses, wound healing, cell adhesion, cell-cell recognition, and extracellular matrix deposition. TGF-β acts as an immune suppressant by counteracting the proliferative effects of interleukin 2 (IL-2) on T and B cells, and by inhibiting the induction of NK cell activities and of LAK cells by IL-2 (Rook et al., J. Immunol. 136:3916, 1986). In addition, TGF-β inhibits T cell-dependent polyclonal antibody production, mixed leukocyte reactions, and the development of CTLs (Ranges et al., J. Exp. Med. 166:991, 1987). Disregulation of TGF-β function is implicated in the pathological processes of several diseases, including arthritis, atherosclerosis, and glomerulonephritis. In addition, cells that lose the ability to respond to TGF-β may be more likely to exhibit uncontrolled proliferation and become tumorigenic. In contrast to these proliferation-inhibiting effects of TGF-β, the protein is known to be chemotactic and mitogenic for fibroblasts, and to be a potent chemoattractant for macrophages. It also possesses angiogenic activity.

The biological effects of TGF-β are mediated by several specific cell surface proteins, including the so-called type I, type II, type III, type IV, type V, and type VI TGF-β receptors. Most of these were initially identified by chemically crosslinking radioiodinated TGF-β to cell surface proteins, using the bifunctional reagent DSS. Almost all TGF-β-responsive cell lines express both the type I and type II receptors, although the levels of their expression may vary among different cell types. Neither type I nor type II receptor in the absence of the other can mediate a TGF-β response, although the type II receptor alone is capable of binding TGF-β (Wrana et al., Cell 71:1, 1992; Boyd et al., J. Biol. Chem. 264:2272, 1989). It appears that the ligand signals through a heteromeric complex between the type I and type II receptors (Wrana et al., supra). The type II TGF-β receptor has been cloned; it is a member of the transmembrane serine/threonine receptor kinase family (Lin et al., Cell 68:1, 1992).

Müllerian Inhibiting Substance (MIS) plays a critical role in normal sexual dimorphism as one of the early manifestations of the SRY genetic switch (Gubbay et al., Nature 346:245–250, 1990; Sinclear et al., Nature 346:240–244, 1990; Berta et al., Nature 348:448–350, 1990; Haqq et al., Proc. Natl. Acad. Sci. USA 90:1097–1101, 1993). MIS subsequently causes regression of the Müllerian duct, inhibition of aromatase activity which leads to increased synthesis of testosterone, and probably morphological differentiation of the sex cords as seminiferous tubules, thus assuring the male phenotype. Jost's seminal observations in the late 1940s first defined a "Müllerian Inhibitor" responsible for regression of the Müllerian ducts in the male mammalian embryo (Jost, Arch. Anat. Micro. Morphol. Exp. 36:271–315, 1947). MIS was found to be a 140 kDa protein produced by the Sertoli cell (Blanchard and Josso, Pediatr. Res. 8:968–971, 1974); it was subsequently purified to homogeneity (Budzik et al., Cell 21:909–915, 1980, Cell 34:307–314, 1983; Picard et al., Mol. Cell. Endocrinol. 34:23, 1984), using the bioassay of Müllerian duct regression devised by Picon (Arch. Anat. Microsc. Morphol. Exp. 58:1–19, 1969) as a monitor. The bovine and human genes were cloned (Cate et al., Cell 45:685–698, 1986a) and subsequently expressed and produced in mammalian cell cultures (Cate et al., Cold Spring Harbor Symposium 51:641–647, 1986b; Epstein et al., In Vitro Cellular and Developmental Biol. 25:213–216, 1989); more recently, the rat (Haqq et al., Genomics 12:665–9, 1992) and mouse (Munsterberg and Lovell-Badge, Development 13:613–624, 1991) genes have also been cloned. Overexpression of MIS in transgenic female mice caused regression of Müllerian ducts and seminiferous tubular differentiation (Behringer et al., Nature 345:167–70, 1991). Several patients with Retained Müllerian Duct Syndrome were found to have point mutations in the MIS gene (Knebelman et al., Proc. Natl. Acad. Sci. 88:3767–3771, 1991), which has been localized to the short arm of chromosome 19 (Cohen-Hagenaur et al., Cytogenet. Cell. Genet. 44:2–6, 1987). In mice, the MIS gene is located on chromosome 10 (King et al., Genomics 11:273–283, 1991).

MIS is a member of the large TGF-β family, which includes, besides TGF-β (Derynck et al., Nature 316:701–5, 1985), activin (Ling et al., Nature 321:779–82, 1986; Vale et al., Nature 321:776–779, 1986); inhibin (Mason et al., Nature 318:659–63, 1985); decapentaplegia complex (Padgett et al., Nature 325:81–4, 1987); Vg-1 (Weeks and Melton, Cell 51:861–7, 1987); and bone morphogenesis factors (Wozney et al., Science 242:1528–34, 1988). A common feature of some members of this gene family is that latent precursor can be activated by plasmin cleavage and release of 25 kDa carboxyl terminal dimers.

Although originally defined and named by its ability to cause regression of the Müllerian duct, other functions have emerged for MIS. Its localization to the preantral and smaller antral follicles by immunocytochemical techniques (Takahashi et al., Biol. Reprod. 35:447–53, 1986a; Bezard et al., J. Reprod. Fertil. 80-509–16, 1987; Ueno et al., Endocrinol. 125:1060–1066, 1989a; Ueno et al., Endocrinology 124:1000–1006, 1989b) and its ability to inhibit germinal vesicle breakdown (Takahashi et al., Mol-Cell-Endocrinol. 47:225–34, 1986b; Ueno et al., Endocrinology 123:1652–1659, 1988) led to the hypothesis that it was involved in meiotic inhibition in the ovary. Developmental and experimental correlations support such a function in the testis (Taketo, et al., Devel. Biol. 146:386–395, 1991), where analysis of timing of expression suggests that MIS may be responsible for inhibition of germ cell division. Hutson and Donahoe (Endocrine Reviews 7:270–283, 1986) speculated that MIS may also play role in the transabdominal portion of testicular descent, and Vigier et al. (Development 100:43–55, 1987; Proc. Natl. Acad. Sci. USA 86:3684–8, 1989) have provided evidence that it functions as an inhibitor of aromatase in developing ovaries. Catlin et al. (Am. J. of Obstet. and Gynecol. 159:1299–1303, 1988; Am. Rev. Resp. Dis. 141:466–470, 1990) showed that MIS decreases surfactant accumulation in fetal lungs, thus contributing to the male preponderance in newborn infants of Respiratory Distress Syndrome. The development of a specific serum MIS ELISA (Hudson et al., J. Clin. and Metab. 70:16–22, 1990; Josso et al., J. Clin. Endocrinol. Metab. 70:23–7, 1990) has led to its experimental use as a diagnostic tool for the elucidation of the pathophysiology of ambiguous genitalia in the newborn, and for the use of serum MIS as a marker of granulosa and sex cord tumors in the adult female. Furthermore, the extraordinarily high MIS level observed by Gustafson et al. (New Eng. J. Med. 326:466–71, 1992) in a patient with a sex cord tumor (3200 ng/ml, compared to a normal level of 2–3 ng/ml) provides evidence that MIS is not toxic at these levels.

The role of MIS as a fetal inhibitor has led to the hypothesis that it might act as a tumor inhibitor, particularly of tumors emanating from the Müllerian ducts (Donahoe et al., Science 205:913–915, 1979; Donahoe et al., Ann. Surg. 194:472–480, 1981; Fuller et al., J. Clin. Endocrin. Metab. 54:1051–1055, 1982; Fuller et al., Gynecol. Oncol. 17:124–132, 1984; Fuller et al., Gynecol. Oncol. 22:135–148, 1985). Experimental evidence has accumulated supporting the ability of recombinant human MIS to exert an antiproliferative effect against genital tract tumors in colony inhibition assays, subrenal capsule assays (Chin, et al., Cancer Research, 51:2101–6, 1991), and now metastases assays, and more recent evidence has shown an antiproliferative effect against a series of human ocular melanomas (Parry et al., Cancer Research 51:1182–6, 1992). MIS has been shown to block tyrosine autophosphorylation of EGF receptors (Coughlin et al., Mol. and Cell. Endocrin. 49:75–86, 1987; Cigarroa et al., Growth Factors 1:179–191, 1989).

Inhibin, another member of the TGF-beta family described above, is primarily secreted by Sertoli and granulosa cells of the male and female gonad. This nonsteroidal regulatory hormone, first described in 1932 (McCullagh, Science 76:19–20), acts specifically to inhibit FSH release from the pituitary (Vale et al., Recent Prog. Horm. Res. 44:1–34, 1988). Biologically active inhibin, however, was not purified and characterized well until the successful cloning of its genes in 1985–86 (Mason et al., Nature 318:659, 1985; Forage et al., Proc. Natl. Acad. Sci. USA 83:3091, 1986; Mayo et al., Proc. Natl. Acad. Sci. USA 83:5849, 1986; Esch et al., Mol. Endocrinol. 1:388, 1987). Inhibin was shown at that time to be a glycoprotein heterodimer composed of an alpha-chain and one of two distinct beta-chains (beta-A, beta-B) (Mason et al., Biochem. Biophys. Res. Comun. 135:957, 1986). The alpha chain is processed from an initial species of 57 kDa to form an 18 kDa carboxyl-terminal peptide, while the mature beta chain of 14 kDa is cleaved from the carboxyl-terminus of a 62 kDa precursor, which would then account for the biologically active 32 kDa species which predominates in serum (DeKretser and Robertson, Biol. Reprod. 40:3347, 1989). Many other forms of bioactive inhibin with MS's of 32–120 kDa, however, have been isolated as well (Miyamoto et al., Biochem. Biophys. Res. Commun. 136:1103–9, 1986). In addition, beta-chain dimers (beta-A/beta-A, beta-B/beta-B, or beta-A/beta-B) which selectively stimulate FSH secretion from the pituitary have been identified and are called activin A, activin B, and activin AB, respectively (Vale et al., Nature 321:776, 1986; Ling et al., Nature 321:779, 1986).

As is the case with MIS, many additional functions have been postulated for inhibin and its subunits besides FSH regulation. Inhibin alpha, beta-A, and beta-B subunit RNAs have been shown to be expressed in a variety of rat tissues, including the testis, ovary, placenta, pituitary, adrenal gland, bone marrow, kidney, spinal cord, and brain (Meunier et al., Proc. Natl. Acad. Sci. USA 85:247–51, 1988). The pattern of testicular inhibin secretion appears to be developmentally regulated. In the rat, inhibin increases during maturation until 30–40 days after birth, after which values rapidly return to juvenile levels (Au et al., Biol. Reprod. 35:37, 1986). Inhibin subunits also seem to have a paracrine effect on Leydig and theca interna cell androgen synthesis (Hsueh et al., Proc. Natl. acad. Sci. USA 84:5082–6, 1987). Many studies have demonstrated the changes in inhibin which occur throughout the estrus cycle, and therefore, its role in modulating FSH in adult females (Hasegawa et al., J. Endocrinology 121:91–100, 1989; McLachlan et al., J. Clin. Endo. Metab. 65:954–61, 1987). Furthermore, changes in local inhibin concentrations may be involved in the regulation of ovarian folliculogenesis (Woodruff et al., Science 239:1296–9, 1988; Woodruff et al., Endocrinology 127:3196–205, 1990). Bioactive inhibin has been shown to be produced by human placental cells in culture and to be involved in a short-loop feedback between gonadotropin-releasing hormone and human chorionic gonadotropin (Petraglia et al., Science 237:187–9, 1987). Finally, a number of patients with ovarian granulosa cell tumors have been described who had markedly elevated serum inhibin levels secondary to tumor production of this hormone (Lappohn et al., NEJM 321:790–3, 1989).

Most of the data that exist concerning serum inhibin levels in humans has been obtained using a heterologous radioimmunoassay comprised of a polyclonal antibody to purified, intact bovine inhibin and radiolabeled 32 kDa bovine inhibin (McLachlan et al., Mol. Cell. Endocrinol. 46:175–85, 1986). Such studies have evaluated normal cycling females and adult males (McLachlan et al., J. Clin. Endo. Metab. 65:954–61, 1987; McLachlan et al., J. Clin. Invest. 82:880–4, 1988), pubertal males (Burger et al., J. Clin. Endo. Metab. 67:689–694, 1988), normal pregnant women (Abe et al., J. Clin. Endocrinol. Metab. 71:133–7, 1990), and a variety of reproductive disorders (Scheckter et al., J. Clin. Endocrinol. Metab. 67:1221–4, 1988; DeKretser et al., J. Endocrinol. 120:517–23, 1989). However, recent work has shown that this assay detects inhibin alpha-subunits as well as intact dimeric hormone, and, therefore, these results should be interpreted with caution (Schneyer et al., J. Clin. Endocrinol. Metab. 70:1208–12, 1990).

SUMMARY OF THE INVENTION

The invention features a novel isolated DNA of the TGF-β receptor family, which isolated DNA encodes a TGF-β type I receptor; this receptor is, e.g., that of a mammal such as a rat, mouse, rabbit, guinea pig, hamster, cow, pig, horse, goat, sheep, or human; or of a non-mammalian vertebrate such as a bird (e.g., a chicken or duck) or a fish. The invention also includes vectors (e.g., plasmids, phage, or viral nucleic acid) or cells (prokaryotic or eukaryotic) which contain such DNAs, and the polypeptides produced by expression of such DNAs (for example, by a cell transformed with and capable of expressing a polypeptide from the DNA). By "isolated DNA" is meant a DNA that is not immediately contiguous with both of the coding sequences with which it is immediately contiguous (i.e., one at the 5' and one at the 3' end) in the naturally-occurring genome of the organism from which the DNA of the invention is derived. The term thus encompasses, for example, a cDNA or a genomic DNA fragment produced by PCR or restriction endonuclease treatment, whether such cDNA or genomic DNA fragment is incorporated into a vector, integrated into the genome of the same or a different species than the organism from which it was originally derived, linked to an additional coding sequence to form a hybrid gene encoding a chimeric polypeptide, or independent of any other DNA sequences. The DNA may be double-stranded or single-stranded, sense or antisense. Examples of isolated DNAs of the invention include one which encodes an amino acid sequence substantially the same as that shown in FIG. 4 (SEQ ID NO: 16); and those having sequences which hybridize under conditions of high or moderate stringency to either strand of the coding sequence of the misr4 plasmid included in the ATCC deposit designated No. 75213, which plasmid can be obtained from the deposit as described below. High stringency conditions are herein defined as the following: hybridizing with 50% deionized formamide, 800 mM NaCl; 20 mM Pipes, pH 6.5, 0.5% SDS, 100 µg/ml denatured, sonicated salmon sperm DNA at 42° C. for 12–20 hours, washing with 30 mM NaCl/3.0 mM sodium citrate (0.2× SSC)/0.1% SDS at 55° C., while moderate stringency conditions are as follows: hybridizing with 50% deionized formamide, 800 mM NaCl; 20 mM Pipes, pH 6.5, 0.5% SDS, 100 µg/ml denatured, sonicated salmon sperm DNA at 42° C. for 12–20 hours, washing with 75 mM NaCl/7.5 mM sodium citrate (0.5×SSC)/0.1% SDS at 55° C.

The isolated DNA of the invention may be under the transcriptional control of a heterologous promoter (i.e., a promoter other than one naturally associated with the given receptor gene of the invention), which promoter, for example, may direct the expression of the DNA of the invention in a particular tissue or at a particular stage of development.

Also within the invention is a substantially pure preparation of a TGF-β type I receptor protein, prepared, for example, from a natural source, from an expression system expressing the isolated DNA of the invention, or by synthetic means. This protein may, for example, have a sequence the same as, or substantially identical to, that shown in FIG. 4 (SEQ ID NO: 17), or that encoded by plasmid misr4 deposited as ATCC Accession No. 75213. By "substantially pure preparation" is meant that the preparation is at least 70% free of those proteins with which the protein of the invention is naturally associated in the tissue(s) in which it naturally occurs. In preferred embodiments, the preparation is at least 90% free of such contaminating proteins.

Also within the invention is a substantially pure nucleic acid at least 20 nucleotides in length (preferably at least 50 nucleotides, more preferably at least 100 nucleotides, and most preferably 1000 nucleotides or more in length) which hybridizes under highly stringent conditions to either strand of the coding region of plasmid misr4 included in the ATCC deposit designated No. 75213. By "substantially pure nucleic acid" is meant an RNA or DNA molecule which is substantially free of those other nucleic acid molecules, if any, with which it is naturally associated in the cell from which it was originally derived (i.e., such other nucleic acid molecules make up less than 50% of the total number of nucleic acid molecules in the preparation). By "other nucleic acid molecules" is meant nucleic acid molecules which do not encode the same polypeptide as the nucleic acid of the invention. In preferred embodiments, less than 20%, and more preferably less than 10% of the preparation consists of such other nucleic acid molecules. Such a nucleic acid may be employed in a Northern analysis or in situ hybridization assay for determining the level of expression of the gene in a biological sample, which assay would include the steps of (1) providing the isolated DNA of the invention, in the form of single stranded antisense DNA; (2) contacting, under hybridizing conditions (preferably of high stringency), the isolated DNA with a biological sample suspected of containing mRNA encoding a receptor of the invention; and (3) determining the level and/or pattern of hybridization of the isolated DNA in the biological sample, such level or pattern of hybridization in the sample being indicative of the level or pattern of expression of the gene encoding the receptor in the tissue represented by that biological sample.

As described below, the TGF-β type I receptor proteins of the invention can be used for a number of purposes. They can be fixed by standard means to a matrix material which also contains TGF-β type II receptor, to form an affinity matrix capable of binding TGF-β. This affinity matrix would be useful for purifying ligand, for screening for inhibitors of the ligand/receptor interaction, or for determining the amount of ligand present in a given biological sample. They can be used in an assay including the steps of (1) providing the polypeptide of the invention (e.g., in soluble form, or imbedded in the membrane of intact or lysed cells which also bear TGF-β type II receptor); (2) contacting the polypeptide with a biological sample suspected of containing TGF-β or a biologically active fragment thereof; and (3) determining the amount of receptor/ligand complex formation in the sample, such amount of complex formation being indicative of the amount of TGF-β activity in the sample. They can also be used to generate monoclonal or polyclonal antibodies specific for (i.e., capable of forming an immune complex with) the TGF-β type I receptor, which antibodies would be useful in a method for detecting the presence of the receptor in a biological sample such as serum or tumor cells. Such a method would include the steps of (1) contacting the antibody of the invention with a biological sample suspected of containing a TGF-β type I receptor, and (2) detecting immune complex formation between the antibody and a component of the biological sample, such immune complex formation being indicative of the presence of such a receptor in the sample. Furthermore, such antibodies can be linked to a cytotoxic agent, thereby forming an immunotoxin useful for targeting and killing or disabling cells bearing the receptor of the invention.

The isolated DNA can be used to generate a transgenic animal (e.g., a mammal such as a mouse, rat, guinea pig, hamster, rabbit, cow, pig, horse, goat, or sheep) which expresses TGF-β type I receptor in a particular tissue of interest. Such a transgenic animal would be generated by standard methods, using the DNA of the invention linked to expression control sequences which induce expression in the selected tissue type. The animal can be made co-transgenic for a DNA encoding TGF-β type II receptor, or can be crossed with an animal transgenic for the type II receptor, in order to ensure that both the type I and the type II receptors are expressed in the same cells. Such animals would be useful for studying the in vivo effects induced by TGF-β in various tissue types at various stages of development.

The DNA of the invention can also be used to generate, by standard methodologies practiced by those of ordinary skill, "knock-out" animals (e.g., mice) which lack the normal genes encoding the TGF-β type I receptor. Such animals will provide information concerning the in vivo role of the type I receptor throughout the life of the animal.

Experiments described below establish that mutant cells which lack or at least fail to express a functional endogenous type I receptor gene can be transfected with a DNA encoding the TGF-β type I receptor which, upon expression, supplies the missing type I receptor function. These results indicate that it may be possible to treat, by genetic therapy utilizing a DNA of the invention, a tumor characterized by a loss of inhibition by TGF-β attributable to absence of functional type I receptor. The tumor cells would be transfected with the DNA of the invention linked to appropriate expression control sequences which permit expression in the tumor cells. The expression control sequences would preferably include an inducible promoter that would turn on expression solely in response to a particular, externally-controlled stimulus, to neutralize what is likely to be selection pressure against the TGF-β type I receptor due to its growth-inhibiting character. Examples of such externally inducible promoters include the IPTG promoter and the metallothianine promoter.

Another use for genetic therapy utilizing the TGF-β type I receptor gene is based upon the ability of TGF-β to accelerate wound healing. A DNA encoding the type I receptor linked to expression control sequences which permit expression in the fibroblasts and other cells immediately surrounding a wound would be transfected into such cells. If necessary, the type II receptor could be co-transfected into the same cells. In the presence of ample TGF-β, which can be endogenous or exogenous, the cells would be stimulated to perform the functions associated with TGF-β-induced wound healing, such as increased production and deposition of extracellular matrix components and increased connective tissue formation.

A soluble form of the receptor of the invention containing the extracellular domain of the protein can be produced by standard recombinant DNA methodology, as described below. In the presence of type II receptor, this soluble type I receptor would bind ligand but would not transduce an intracellular signal. Since the bound ligand would not be available to activate cell-surface receptors, the immune-suppressing and growth-inhibiting activities of TGF-β would be inhibited.

Alternatively, the soluble type I receptor could be chemically or recombinantly conjugated to a cytotoxin, and the cytotoxic hybrid thereby produced used to target and kill cells bearing type II but not type I receptors, such as tumor cells which have lost the type I receptor phenotype. The hybrid would target these cells by binding to cell-surface type II receptors in the presence of ligand.

Other features and advantages of the invention will be apparent from the following detailed description, and from the claims.

DETAILED DESCRIPTION

The drawings are first described.

DRAWINGS

FIGS. 1A–B are a representation of the DNA coding sequence of misr1 (SEQ ID NO: 1), and the corresponding amino acid sequence of the encoded receptor protein (SEQ ID NO: 14), which is referred to herein as MISR1 or simply R1.

FIGS. 2A–B are a representation of the DNA coding sequence (SEQ ID NO: 2) of two overlapping cloned cDNAs, misr2A and misr2B, and the corresponding amino acid sequence of the encoded receptor protein (SEQ ID NO: 15), which is referred to herein as MISR2 or simply R2.

FIGS. 3A–B are a representation of the DNA coding sequence of misr3 (SEQ ID NO: 3), and the corresponding amino acid sequence of the encoded receptor protein (SEQ ID NO: 16), which is referred to herein as MISR3, or simply R3.

FIGS. 4A–B are a representation of the DNA coding sequence of misr4 (SEQ ID NO: 4), and the corresponding amino acid sequence of/the encoded receptor protein (SEQ ID NO: 17), which is referred to herein as MISR4, or simply R4.

FIGS. 5A–5E show partial 20 nucleotide sequences of each of misr1 (SEQ ID NO: 5), misr2A (SEQ ID NO: 6), misr2B (SEQ ID NO: 7), misr3 (SEQ ID NO: 8), and misr4 (SEQ ID NO: 9), respectively.

Figure 6A:
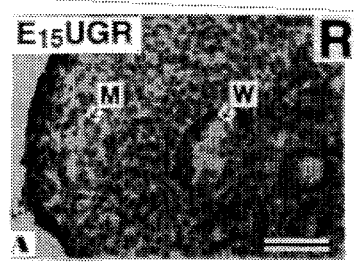
Figure 6B:
Figure 6C:
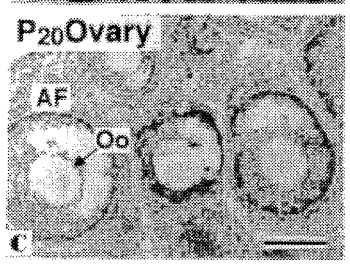
Figure 6D:
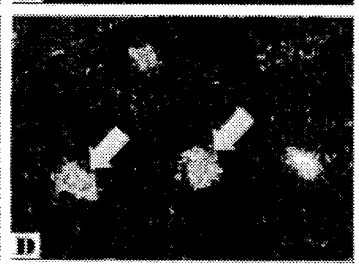
Figure 6E:
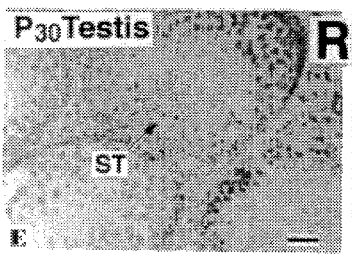
Figure 6F:
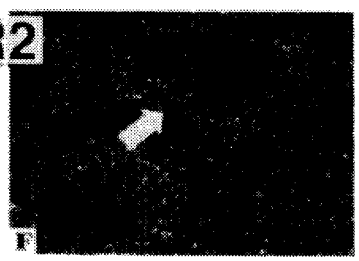

FIGS. 6A–6F are photographs showing in situ hybridization of the urogenital ridge (UGR), ovary, and testis with a riboprobe (R1) derived from misr1 (SEQ ID NO:1) and a second riboprobe (R2) derived from misr2 (SEQ ID NO: 2). Left-hand panels (FIGS. 6A, 6C, and 6E) are representative brightfield views in which hybridization signals appear as black granules (Bar=100 μm); right-hand panels (FIGS. 6B, 6D, and 6F) are identical darkfield views in which RNA message appears as bright spots (heavy arrows). FIGS. 6A and 6B: R1 hybridization signal in the 15-day (E15) fetal male UGR is conspicuous over the mesenchyme of the Mullerian duct (M), but not over the adjacent Wolffian duct (W). FIGS. 6C and 6D: R1 signal is also intense over the oocytes (Oo) of preantral and antral follicles (AF) of the postnatal day 20 (P20) ovary, with less intense signal over their adjacent granulosa cells. Two separate R1 riboprobes were used to confirm these findings in FIGS. 6A–6D: one from the 5' extracellular domain and one from the 3' intracellular region of the coding sequence. FIGS. 6E and 6F: R2 signal localizes in a heterogeneous pattern to seminiferous tubules (ST) of the postnatal day 30 (P30) testis. No R2 message was detected in the fetal Mullerian duct or the pubertal and adult ovary. Both R1 and R2 signals were found in the female postnatal anterior pituitary and hippocampus (data not shown).

Figure 7B:
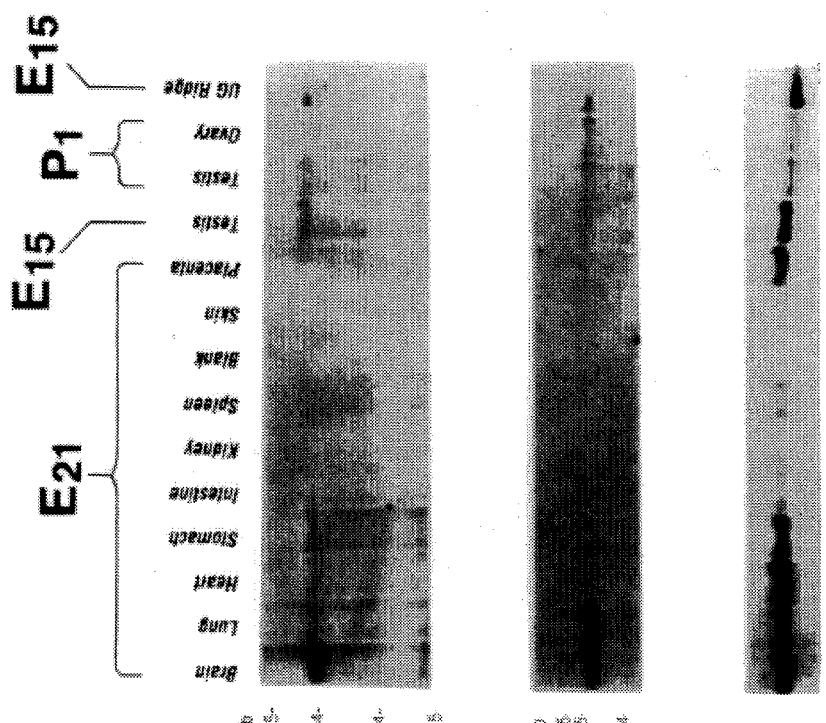
Figure 7A:
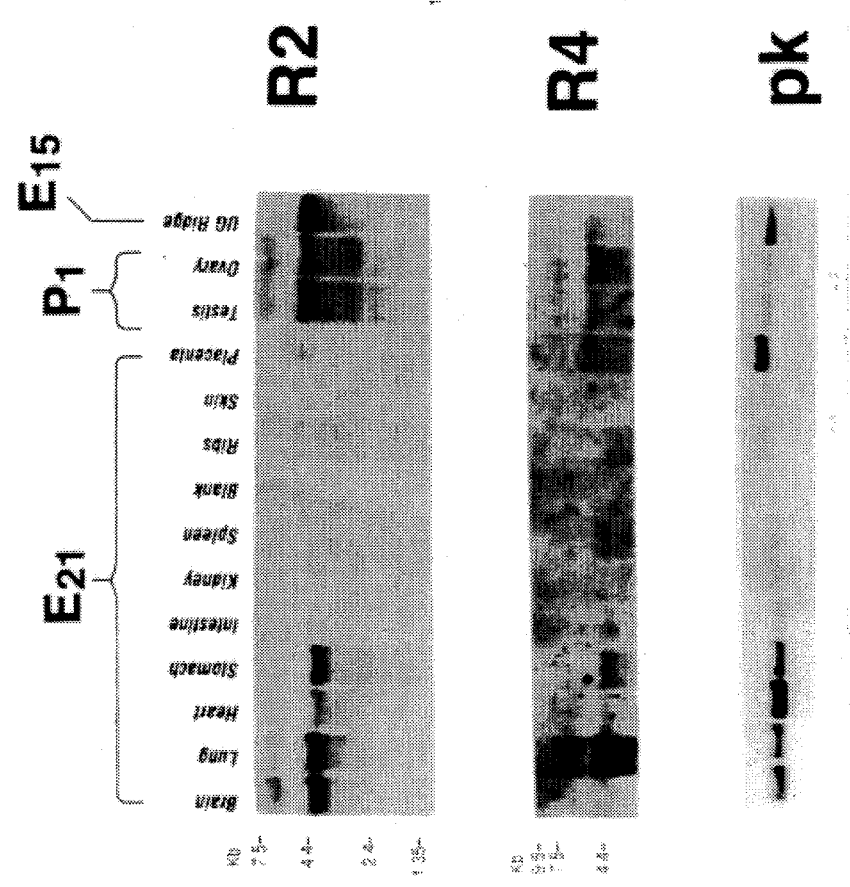

FIGS. 7A–B shows the results of Northern analysis of fetal and postnatal rat tissues for MISR1–MISR4 mRNA expression. The left blot was hybridized sequentially with misr1, misr3 and pyruvate kinase (pk) probes, while the right blot was probed serially with misr2a/misr2b, misr4 and pk. Approximately 4.0 kb MISR1, 4.4 and 1.5 kb MISR2, 4.4 kb MISR3, and 6 kb MISR4 transcripts were all detected in the 15-day (E15) fetal urogenital ridge (UGRidge) and postnatal day 1 (P1) testis and ovary. mRNAs for MISR1, MISR2, and MISR4 were abundant in the 21-day (E21) fetal brain. MISR1–MISR4 message was also present in the E21 fetal lung; other E21 issues, such as the lung, heart, and stomach, contained variable levels of MISR1 and MISR2 mRNA.

Figure 8:
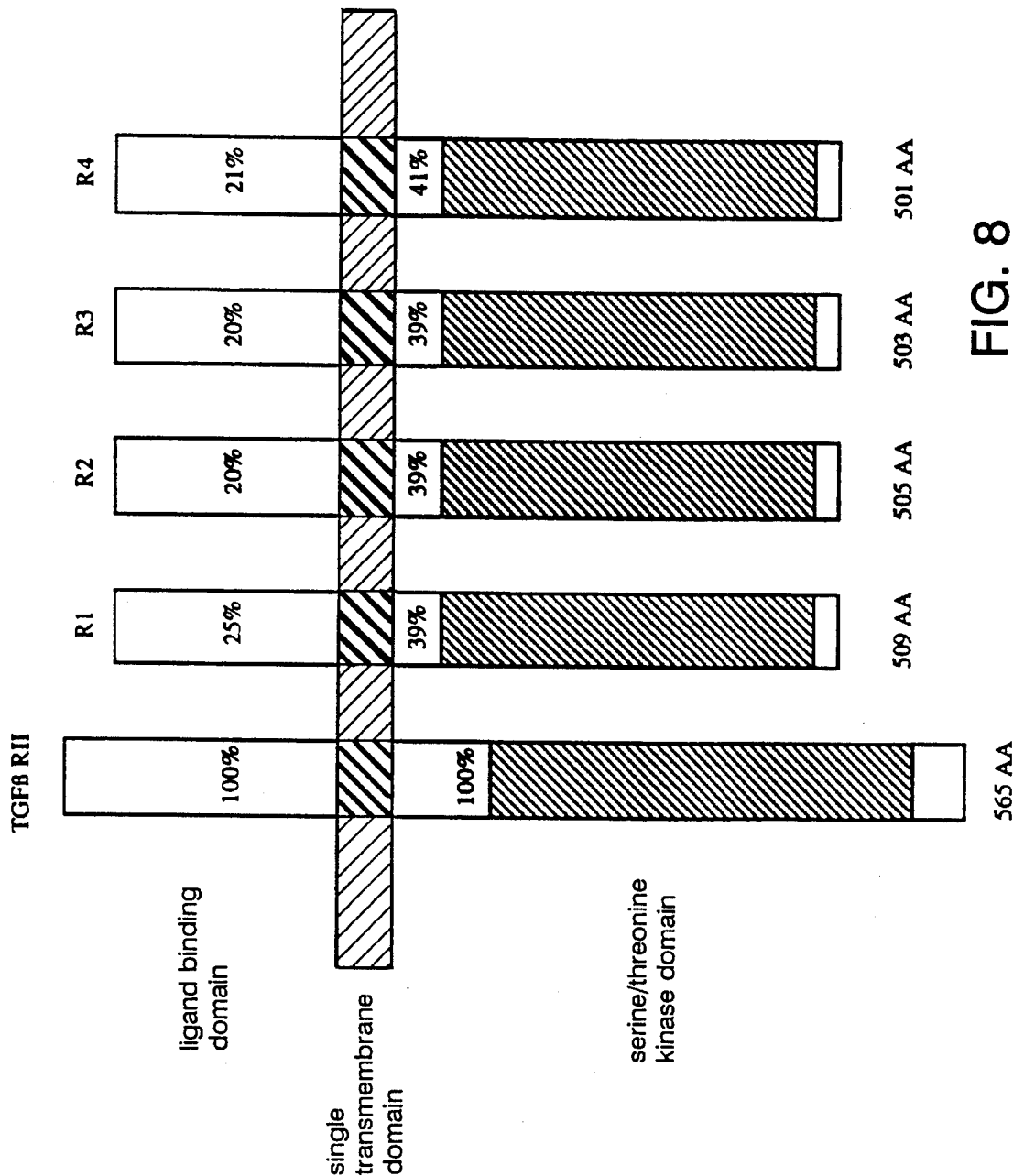

FIG. 8 is a schematic diagram generally comparing the percent similarity of the amino acid sequence of each of MISR1–MISR4 (SEQ ID NOs: 14–17) to that of the TGF-β type II receptor. The percent amino acid similarity of the extracellular and kinase domains of each clone as compared to the corresponding portion of the TGF-β type II receptor sequence is indicated. The sequence similarities were generated by the GAP program of the Genetics Computer Group. The nucleotide sequence of the MISR1–MISR4 clones (SEQ ID NOs: 1–4) have been submitted to GenBank.

Figures 9A, 9B:
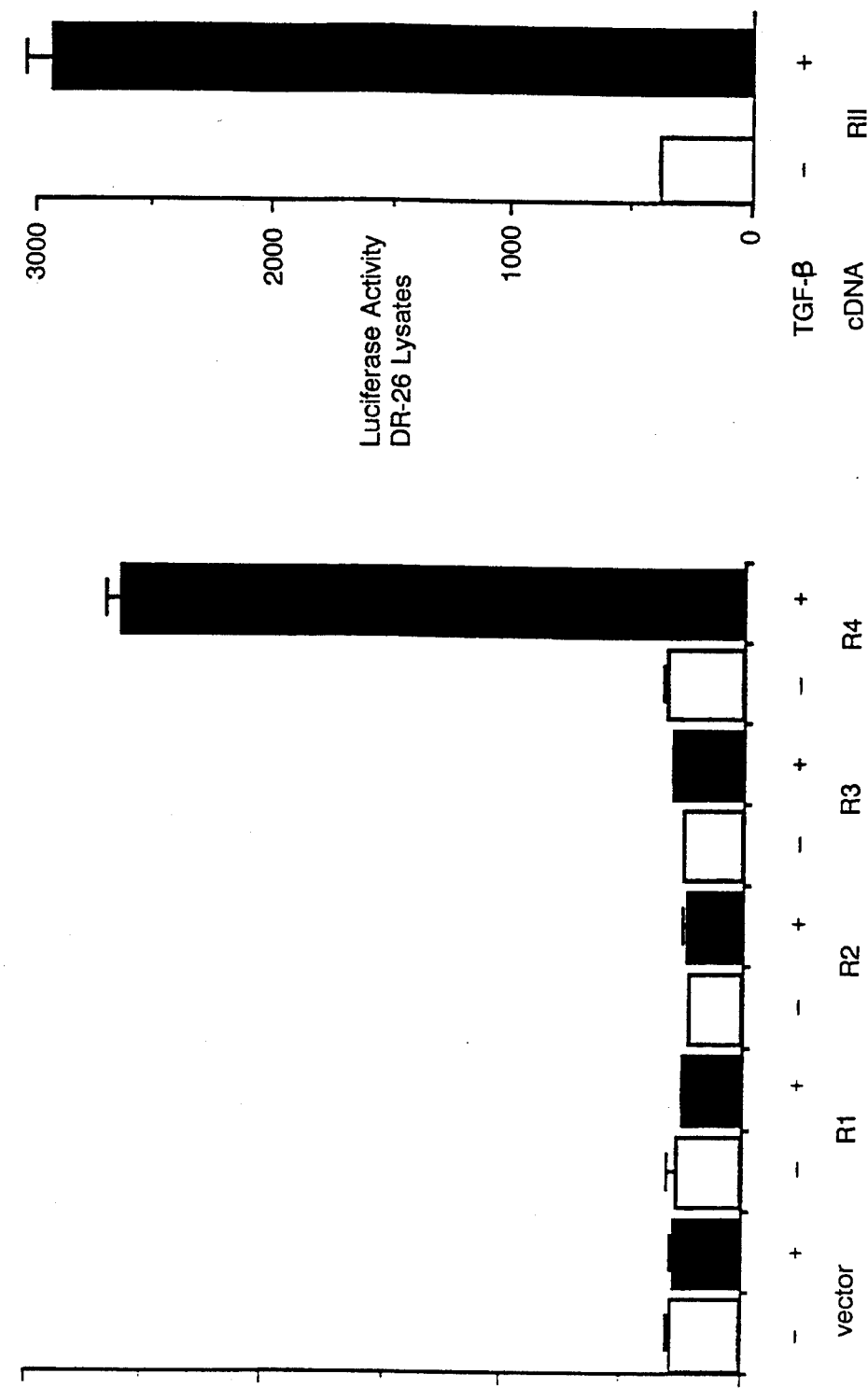

FIGS. 9A and 9B are a pair of bar graphs illustrating the results of a screen for the ability of each of MISR1–MISR4 to restore a TGF-β dependent gene response in the nonresponsive R1B mutant cell line.

FIG. 9A: R1B cells were transiently co-transfected with 6 ug of p3TP-Lux and 6 ug of either pCMV4, pCMV8-R1, pCMV4-R2, pCMV6-R3, or pCMV6-R4. Twelve hours after transfection, cells were placed in 0.2% FBS/DMEM for 36 hrs in the absence or presence of 240 pM TGF-β1. Cells were lysed and the level of luciferase activity in the extracts assayed by integrating light emission over 30 seconds on a Berthold luminometer. All the experiments involving transfection and luciferase assays, including the ones described in the next few figures, were done at least two times with triplicates in each experiments. The bars indicate the average values of luciferase activity derived from a representative experiment.

FIG. 9B: As a positive control, 6 ug of p3TP-Lux and 6 ug of the human TGF-β type II receptor cDNA (pCMV8-RII) were transiently co-transfected into the DR-26 mutant cell line. These cells were also treated with and without TGF-β1 for hrs, and then assayed for luciferase activity.

FIGS. 10A and 10B are a pair of bar graphs illustrating the functional characterization of R4.

FIG. 10A: Assay to determine if TGF-β signaling by R4 is dependent upon the presence of a functional type II receptor. DR-26 mutants were transiently co-transfected with 6 ug of p3TP-Lux and 6 ug of either pCMV8-RII or pCMV6-R4. Cells were either treated or untreated with TGF-β1 for 36 hrs and then assayed for luciferase activity.

FIG. 10B: Assay to determine if the kinase activity of R4 is required for TGF-β signaling. R1B mutants were transiently co-transfected with 6 ug of p3TP-Lux and 6 ug of either pCMV6-R4 or pCMV6-R4(K23OR). Cells were either treated or untreated with TGF-β1 for 36 hrs and then assayed for luciferase activity.

Figure 11:
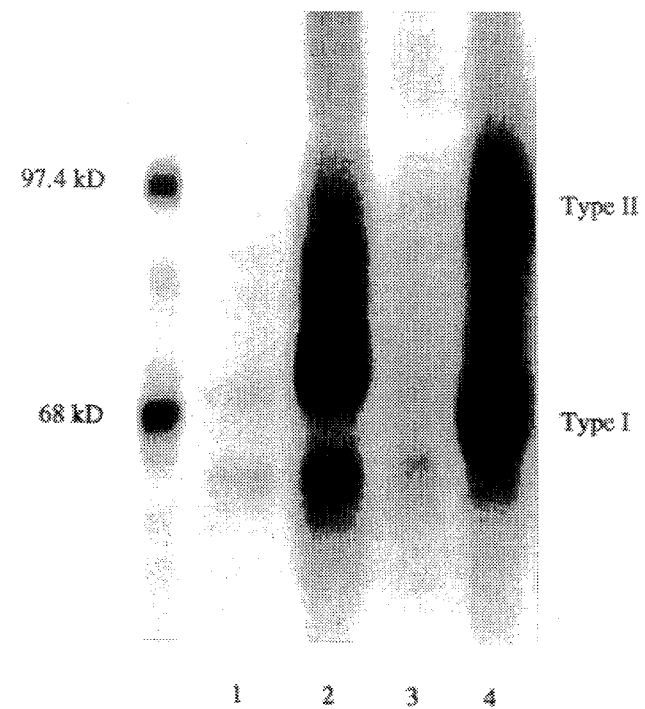

FIG. 11 is an autoradiogram of an SDS-PAGE gel made following affinity cross-linking of radioiodinated TGF-β1 to transiently transfected COS cells. COS cells were transfected with 10 ug pCMV4 (lane 1), 10 ug pCMV8-RII (lane 2), 50 ug pCMV6-R4 (lane 3), or 5 ug pCMV8-RII and 50 ug pCMV6-R4 (lane 4). Cells were grown to confluency and cross-linked with 200 pM $^{125}$I-TGF-β. Each lane represents lysate derived from one third of cells harvested from a 100 mm plate. The sizes of the molecular weight markers are indicated.

Figure 12A:
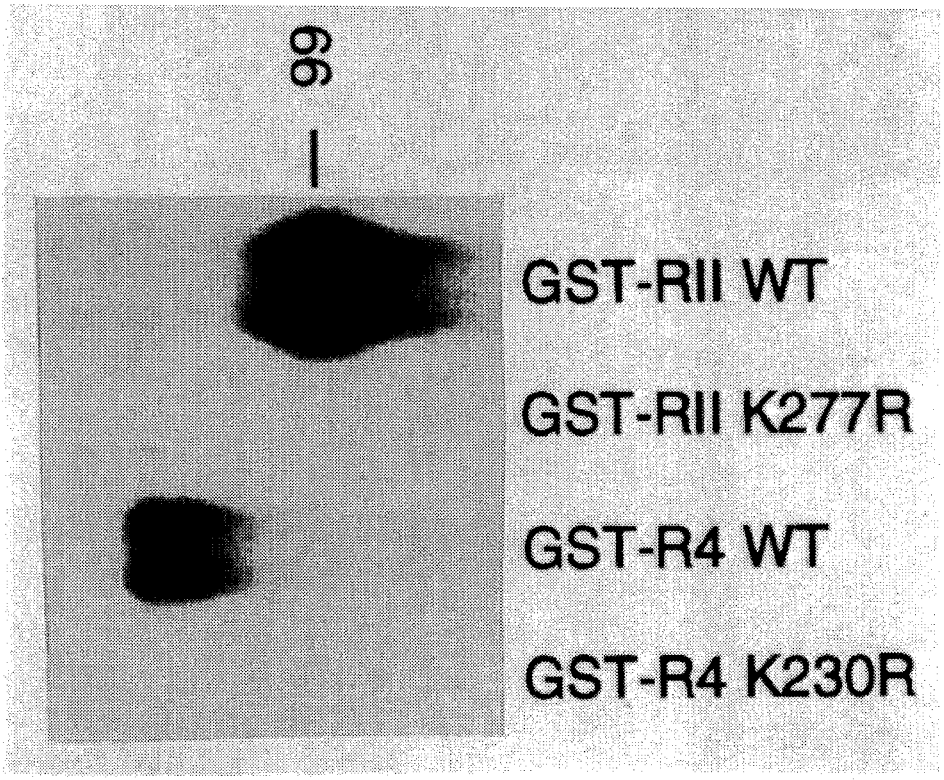

FIG. 12A is an autoradiogram of an SDS-PAGE gel of an in vitro autophosphorylation assay used to compare the kinase activity of GST-RII and GST-R4. An equal amount of protein was loaded in each lane and separated on an 8% SDS-PAGE. Autoradiography was performed at –80° C. for 1.5 hours.

Figure 12B:
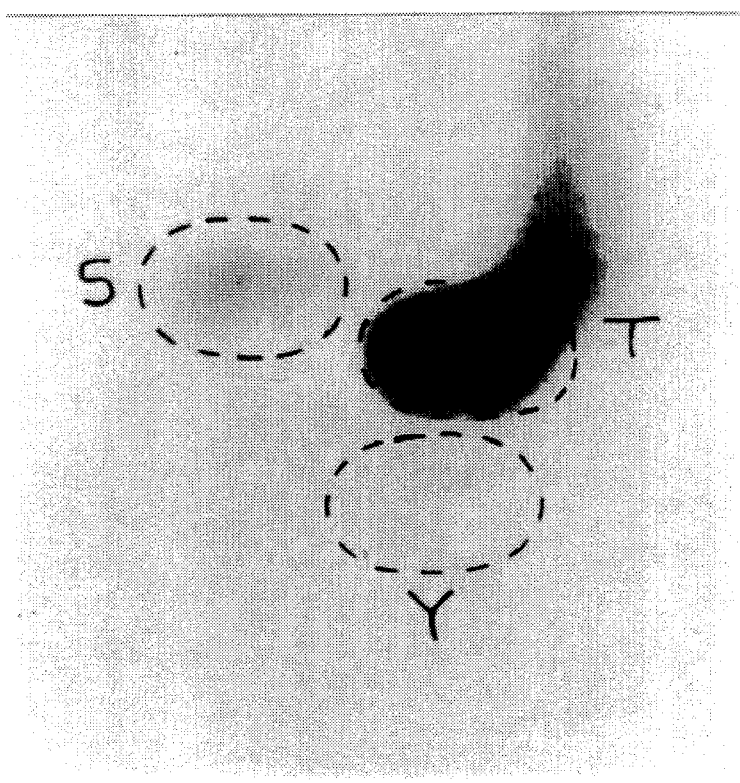

FIG. 12B is a phospho-amino acid analysis of in vitro autophosphorylated GST-R4.

PREPARATION OF THE ISOLATED DNAS OF THE INVENTION

Four different isolated DNAs of the invention were prepared by cloning from a rat embryonic urogenital ridge cDNA library, as described below. Some alternative means of preparing the isolated DNAs of the invention, using the information provided herein and standard techniques, are as follows:

(1) A nucleic acid having the nucleotide sequence shown in any one of FIGS. 1–4 (SEQ ID NOs: 1–4, respectively), or a nucleic acid encoding the amino acid sequence shown in that figure but, owing to the degeneracy of the genetic code, having a nucleotide sequence different from that shown in the figure, may be synthesized by standard chemical means as generally applied to synthesis of oligonucleotides.

(2) A nucleic acid hybridization probe containing at least 20 nucleotides, and preferably at least 50 nucleotides, of one of the DNA sequences shown in any of FIGS. 1–4 (SEQ ID NOs: 1–4) may be prepared by standard methodology and used to probe a "library" of the five plasmids making up the ATCC deposit designated No. 75213. For example, a probe which includes at least a portion of the nucleotide sequence shown in FIG. 1 (SEQ ID NO: 1), such as the partial sequence shown in FIG. 5A (SEQ ID NO: 5), will hybridize under high stringency conditions (e.g., hybridizing in 50% deionized formamide, 800 mM NaCl, 20 mM Pipes, pH 6.5, 0.4% SDS, 500 μg/ml denatured, sonicated salmon sperm DNA at 42° C. for 12–20 hours; and washing in 30 mM NaCl, 3.0 mM sodium citrate, 0.5% SDS at 65° C.) solely with a plasmid containing the complementary sequence, and so would identify clones containing the misr1 sequence. Similarly, the partial sequences shown in FIGS. 5B, 5C, 5D, and 5E (SEQ ID NOs: 6–9, respectively) can be used to identify misr2A, misr2B, misr3, and misr4, respectively. The desired plasmid can be selected as follows:

The plasmid samples deposited with the ATCC and given accession No. 75123 contain 500 ng of each of the five plasmid DNAs in 50 μl final volume. A given clone may be isolated from such a sample by transforming 1 μl of DNA from the sample into bacteria HB 101 by either chemical transformation or electroporation. The transformed bacteria are selected on 1.5% agar plates containing 50 μg/ml ampicillin. Ampicillin-resistant colonies are picked individually and grown in 5 ml of LB broth containing 50 μg/ml ampicillin. The plasmid DNA of a few colonies may then be isolated using the standard plasmid DNA mini-prep procedure. The mini-prep DNA is then characterized by means of a DNA dot-blot, using as hybridization probe one of the $^{32}$P-labelled misr1, misr2A, misr2B, misr3, or misr4-specific probes discussed above. Alternatively, a cDNA library prepared from a tissue that expresses the gene of interest (such as the rat urogenital ridge cDNA library described below), or a genomic library from rat, can be probed with such a hybridization probe under highly stringent conditions.

(3) An isolated DNA prepared by any of the methods outlined herein (including the methods originally used to obtain the DNAs of the invention) may be used to probe an appropriate cDNA library or genomic DNA library from any vertebrate species. The stringency of the hybridization conditions would be adjusted as necessary to obtain the desired homolog, while minimizing the number of related but distinct receptor (such as TGF-β type II or activin receptor) sequences picked up in the assay. It is expected that hybridization and wash conditions such as the highly stringent conditions set forth in (2) above would be adequate; if necessary, the stringency may be increased or decreased, without undue experimentation, using methods well known to those of ordinary skill in the art (see, e.g., Sambrook et al., Molecular Cloning: A Laboratory Manual, Cold Spring Harbor Laboratory, Cold Spring Harbor, N.Y., 1989). A given cloned cDNA or genomic DNA would be identified as a homolog of misr1, misr2, misr3, or misr4 by means of sequence comparison, wherein an encoded amino acid sequence that is at least 70% identical to the amino acid sequence encoded by any one of misr1 (SEQ ID NO: 1), misr2 (SEQ ID NO: 2), misr3 (SEQ ID NO: 3), or misr4 (SEQ ID NO: 4) is considered to be a homolog of that receptor. Given the apparent evolutionary conservation of TGF-β, MIS, inhibin, and bone morphogenesis proteins (BMPs) among vertebrate species in which they have been sought, it is expected that most or all vertebrate species, and certainly all mammalian species, will be found to have genes encoding at least one TGF-β type I receptor, MIS receptor, inhibin receptor, and BMP receptor which can be identified by the methods described herein. It is further expected, based upon the information disclosed herein, that many if not all such species will be found to harbor a plurality of isoforms of such receptor genes.

Each such homolog can be definitively identified as a TGF-β type I receptor (or MIS receptor, inhibin receptor, or BMP receptor, as appropriate) by any of the following assays:

(a) Following transient transfection and expression of the putative TGF-β type I receptor DNA in an appropriate expression system (i.e., a eukaryotic cell line which normally expresses functional type II but not the type I TGF-β receptor (Boyd and Massague, J. Biol. Chem. 264:2272, 1989; Laiho et al., J. Biol. Chem. 265:18518, 1990), the cells are exposed to TGF-β (either recombinant or naturally occurring). Those cells which are successfully transfected with DNA encoding the type I receptor, and which express the type I receptor on their surfaces, are identified by their acquired ability to respond to signalling induced by the ligand's interaction with the type I/type II receptor complex. For example, see the assay described below, which employs mutagenized mink lung epithelial (MvlLu) cells. Alternatively, a cell line which normally expresses neither type I nor type II receptor can be cotransfected with a cDNA encoding type II and a second cDNA encoding a putative type I receptor, and binding to the complex detected by crosslinking labelled ligand to the receptors with a bifunctional reagent such as DSS. Binding of the ligand by transfected but not untransfected cells is evidence that the putative receptor DNA does encode a receptor specific for the ligand. Such experiments could be carried out using as ligand recombinant human TGF-β produced as disclosed in Derynck et al., Nature 316:701–705, 1985 (herein incorporated by reference), and purified by means of an affinity column using an anti-TGF-β monoclonal antibody.

(b) TGF-β can be fixed to an affinity matrix material by standard methods, and then used to assay for proteins which bind to the matrix in the presence of type II receptor (or soluble extracellular domain of type II receptor): for example, the putative type I receptor protein expressed by cells transfected with a cloned DNA of the invention, and isolated from the cells' membranes by standard techniques, can be mixed with recombinant type II receptor (or a soluble fragment thereof) and passed over a column of such affinity matrix material. In a variation on this technique, the putative receptor protein itself can be fixed to the matrix material, and a preparation including the ligand (TGF-β) and soluble type II receptor passed over the column.

(c) Eukaryotic cells which do not normally express the TGF-β type I receptor are transfected with the putative receptor DNA of the invention, and used, in accordance with standard procedures, to generate monoclonal antibodies which can differentiate between such transfected cells and identical but untransfected cells. These monoclonal antibodies are then labelled and used in immunohistochemical analysis of given tissues, in order to determine what tissues normally express the putative receptor DNA, and at what stages of development. A pattern of expression that correlates with the expected pattern (the expected pattern being determined, for example, by the pattern of binding of TGF-β in such tissues) would provide evidence that the putative receptor DNA did indeed encode the predicted receptor.

(d) Monoclonal antibodies raised as described above could also be used in a competitive binding assay. A given tissue sample which, by virtue of its ability to respond to natural or recombinant TGF-β, is known to bear naturally occurring TGF-β I and II receptors, could be employed in a competitive binding assay with either labelled ligand and excess unlabelled antibody raised against the putative receptor (as described above), or labelled antibody and excess unlabelled ligand. Evidence that the ligand and the antibody compete for the same binding sites would support the conclusion that the putative receptor was indeed a TGF-β type I receptor.

(d) Another technique for confirming the identity of a putative receptor of the invention is by the use of Northern blots, probing the RNA of various tissues with a single-stranded hybridization probe made of labelled DNA encoding the putative receptor. The expression of putative receptor-specific genes in tissues known to be affected TGF-β, including both normal and disease-state tissues, and the lack of detectable expression in other tissues known to be insensitive to the candidate ligand, is evidence that the putative receptor is indeed a receptor for the candidate ligand.

USE

The cDNAs of the invention, or fragments thereof long enough to serve as specific hybridization probes, can be duplicated by standard means by transfection into appropriate cells (e.g., bacterial cells), purified, and then used as hybridization probes in Northern or in situ hybridization analyses, in order to determine the level of expression of the relevant mRNA in a particular tissue sample. Alternatively, a vector encoding a receptor of the invention plus appropriate expression control elements can be transfected into a cell capable of expressing the receptor polypeptide. Such cells may express the polypeptide as a surface-anchored receptor, or may secrete the polypeptide or accumulate it within the cell. Purified receptor protein; or cells or membrane preparations bearing the receptor; or synthetic, proteolytic or recombinant fragments of the receptor protein, may be used to generate monoclonal or polyclonal antibodies specific for the given receptor, which antibodies can be employed in assays for detecting the presence or the amount of such receptor in biological samples such as serum or tissue biopsies. TGF-β is known to inhibit the growth of certain lung and colon carcinomas. Similarly, some tumors of the female genital tract, as well as certain ocular melanomas, are susceptible to the antiproliferative effects of MIS (Donahoe et al., Science 205:913–915, 1979; Donahoe et al., Ann. Surg. 194:472–480, 1981; Fuller et al., J. Clin. Endo. Metab. 54:1051–1055, 1982; Fuller et al., Gynecol. Oncol. 22:135–148, 1985; Chin et al., Cancer Res. 51:2101–2106, 1991; Parry et al., Cancer Res. 52:1182–1186, 1992; and Donahoe, U.S. Ser. No. 683,966, herein incorporated by reference), and it is postulated that the growth of other tumor types may be similarly reduced by inhibin or BMP. The antibodies of the invention would therefore be useful for identifying candidate tumors likely to respond to therapy with TGF-β, MIS, inhibin, BMP, or agonists or antagonists thereof. The receptor polypeptides of the invention, and their respective antibodies, could be used as receptor agonists or antagonists in the management of relevant clinical disorders. The antibodies can also be used as the targeting means for directing cytotoxic agents to cells (such as tumor cells) bearing the given receptor. Examples of cytotoxic agents commonly used in such applications include, for example, polypeptide toxins such as diphtheria toxin, Pseudomonas exotoxin A, ricin, and gelonin, or defined toxic portions thereof; radioisotopes; and agents such as cisplatinum, adriamycin, bleomycin, and other therapeutic cytotoxins. Methods for making such immunotoxins are well known to those of ordinary skill in the art, and may include genetic engineering technology as well as chemical-based techniques.

Purified receptor protein, or transformed cells expressing the receptor protein, can be used to screen candidate drugs for their ability to block or enhance the binding of TGF-β and other ligands to their respective receptors. This could be accomplished by means of a competition assay using, for example, labelled ligand and excess candidate drug. Inhibitors of TGF-β binding would potentially be useful for blocking the immune-suppressive and antiproliferative activities of TGF-β, or for preventing arteriosclerosis attributable to excessive wound healing within a blood vessel.

Cells expressing recombinant TGF-β type I receptor (as well as type II receptor), can be used to measure the amount of functional TGF-β present in a biological sample. This could be accomplished, for example, by means of a binding assay. The recombinant receptors of the invention would also be useful as a means for assaying receptor binding by analogs of TGF-β, in order to develop analogs with an enhanced affinity for the type I/type II receptor complex. Those analogs which are capable of stimulating a signal through the receptor can then be used in TGF-β replacement therapy, while those analogs which bind but do not activate the receptor complex will be useful as inhibitors of the natural ligand.

The receptors of the invention may also have therapeutic applications. Transfecting a DNA encoding the TGF-β type I receptor, and containing appropriate expression control elements, into a tumor cell would make the cell more susceptible to growth inhibition by TGF-β, while transfecting the cells in the vicinity of a wound would stimulate wound healing. A soluble fragment of the type I receptor containing the extracellular domain but lacking the membrane-spanning domain would be useful as an inhibitor of TGF-β activity, since it would act, in concert with the type II receptor, to bind free TGF-β. Such soluble receptor fragments can be readily produced by genetically engineering the receptor cDNAs of the invention to delete those portions encoding the largely hydrophobic putative transmembrane regions, but leaving intact the sequences encoding the putative extracellular domains. Such methods are well known in the art. One example of a soluble fragment of MISR4 would include most or all of amino acids 1 to 123 of the sequence shown in FIG. 4 (SEQ ID NO: 17), but would not include amino acids 124 to 146. Alternatively, a given soluble receptor fragment may be produced by proteolytic treatment of naturally occurring or recombinant membrane-bound TGF-β type I receptor.

DEPOSIT

Under the terms of the Budapest Treaty on the International Recognition of the Deposit of Microorganisms for the Purpose of Patent Procedure, a deposit of plasmids misr1, misr2A, misr2B, misr3, and misr4 has been made with the American Type Culture Collection (ATCC) of Rockville, 12301 Parklawn Drive, Md., USA, where the deposit was given Accession No. 75213.

Applicants' assignee, the General Hospital Corporation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

EXPERIMENTAL DATA

Four novel membrane serine/threonine kinase receptor cDNAs from the rat urogenital ridge were cloned and characterized as described below.

POLYMERASE CHAIN REACTION (PCR) USING CONCENSUS PRIMERS

The DNA sequence of the cDNA encoding a murine activin receptor (Mathews and Vale, Cell 65:973–982, 1991) was compared to that of certain related cDNAs: human and porcine TGF-β type II receptor (Lin et al., Cell 68:775–785, 1992) and the daf-1 receptor of C. elegans (Georgi et al., Cell 61:635–645, 1990), and two highly conserved regions defined. These two regions formed the basis for the design of two degenerate oligonucleotides:
5'- GTGGCCGT(G/C)AA(A/G)AT(C/T)TT - 3' (SEQ ID NO: 10)
and 5'- GAC(T/C)TCTGG(G/A)GCCAT(G/A)TA - 3' (SEQ ID NO: 11).
The oligonucleotides were synthesized with an Applied Biosystems 391 DNA synthesizer, and used as primers for polymerase chain reaction (PCR)-based selection from a 14.5 day rat urogenital ridge COS cell expression cDNA library. PCR was carried out in a 50 μl reaction mixture containing about 1 μg of cDNA plasmid; 10 mM Tris-HCl, pH 8.3; 50 mM KCl; 5 mM MgCl$_2$; 0.001% gelatin; 250 μM each of dATP, dCTP, dGTP, and dTTP; 1 unit of Taq polymerase (Perkin-Elmer Cetus); and 50 pmol each of the above oligonucleotides. Thirty cycles of PCR (consisting of denaturation at 94° C. for 1 min; annealing at 37° C. for 1 min; and elongation at 72° C. for 1 min) were performed. The PCR products were separated on a 1.5% agarose gel and a predicted 400–500 bp DNA fragment was sliced out and purified by Gene-clean™. The purified PCR product was blunt-ended with Klenow fragment and phosphorylated with T4 polynucleotide kinase. The final PCR fragment was ligated, using T4 DNA ligase, with plasmid pGEM7Z(+) vector which was digested with Sma I and dephosphorylated. The ligation mixture was incubated at room temperature for 3 hours, and then transformed into bacteria HB 101 by electroporation. Bacterial colonies resistant to ampicillin were selected overnight on 1.5% agar plates containing 50 µg/ml ampicillin. Individual colonies were picked and grown in 5 ml of LB broth, and plasmids were isolated according to a standard plasmid mini-prep protocol. The plasmid DNA was then sequenced with bacterial phage promoter SP6 and T7 primers using Sequenase (USB). Four clones containing PCR fragments encoding portions of four novel polypeptides (putative serine/threonine kinases) were designated pGEM7-Misr1, pGEM7-Misr2, pGEM7-Misr3 and pGEM7-Misr4, respectively. In addition, cDNAs encoding portions of TGF-beta receptor and activin receptor were isolated during this procedure; these were designated pGEM7-tgfb and pGEM7-actr, respectively.

cDNA Library Synthesis

Approximately 450 urogenital ridges and their adjacent gonads were collected from 24 litters of 14.5–15 day gestational age fetal rats, and flash frozen in liquid nitrogen. RNA was then extracted from this tissue by homogenization in 50% guanidinium thiocyanate/14.5% lithium chloride/0.2% β-mercaptoethanol, centrifugation through 5.7M cesium chloride (50 k rpm for 2 hours), and precipitation with NaOAc and ethanol. Poly A+ RNA was further obtained by oligo dT—cellulose chromatography of 620 µg total RNA. Twenty µg of this poly A+ RNA was subsequently used for first strand cDNA synthesis, using 4 µl of reverse transcriptase (RT-XL, Life Sciences), 2.5 µl of 20 mM ultrapure dNTP, 1 µl of oligo dT (Collaborative Research, 5 µg/µl) as primer, 20 µL of RT1 buffer, 1 µL 1.0M DTT, and 2 µl of placental RNase inhibitor (Boehringer, 36 U/µl) in a total volume of 100 µl, incubated for forty-five minutes at 42° C. The second strand synthesis reaction, which employed 5 µl of DNA polymerase I (Boehringer, 5 U/µl) and 2 µl of RNase H (BRL, 2 U/µl), was performed for one hour at 15° C. followed by one hour at 22° C., prior to termination with 20 µl of 0.5M EDTA, pH 8.

The cDNA mixture was then phenol extracted and ethanol precipitated, and then ligated to non-self-complimentary BstX1 linkers (Invitrogen) using 1 µl of T4 DNA ligase (NE Biolabs, 400 U/µl), in a volume of 50 µl incubated at 15° C. overnight. Small cDNA and free linkers were removed by centrifugation through a 5–20% KOAc gradient. Fractions of the gradient that contained cDNA larger than one kilobase were ethanol precipitated with linear polyacrylamide and pooled. After test ligations had determined the optimal ratios, the cDNA was ligated into the COS cell expression vector CDM8, previously digested with BstX1. The cDNA/vector products were electroporated (BioRad Gene Pulser) into competent E. coli MC1061/p3 cells, which were then grown on 20 LB/ampicillin bacterial plates. The resulting cDNA library contained 1×10⁶ individual clones, with an average insert size of 1.5–2.0 kb. Maxiprep plasmid DNA (total yield 1.9 mg) was subsequently obtained from a "pooled" overnight liquid culture of these clones.

A lambda Zap II library was constructed by Stratagene using 20 µg of urogenital ridge mRNA.

Cloning of the full-length cDNAs for Misr1, Misr3 and Misr4, and two partial cDNAs for Misr2

The plasmid DNA of each of pGEM7-misr1, pGEM7-misr2, pGEM7-misr3, and pGEM7-misr4 was prepared in large quantities according to a standard plasmid large-prep protocol. The inserts of individual clones were excised out of the plasmid vector with restriction enzymes Eco RI and Bam HI. The inserts were then gel-separated and purified with Gene-clean™. The purified DNA inserts were labeled with $^{32}$P-dCTP using a random-priming technique, to a specific activity of greater than 1×10⁹ cpm/µg. The individually labeled DNA probes were then used to screen a 14.5 day rat urogenital ridge lambda ZAP II cDNA library made by Stratagene. Positive clones were plaque-purified and the inserts were excised into plasmid pBluescript I SK according to Stratagene's protocol. Full-length clones were sequenced with Sequenase on both strands by synthesizing internal 16–17 oligonucleotide sequencing primers. The full-length DNA coding sequence of misr1 (SEQ ID NO: 1) and the amino acid sequence of its encoded polypeptide (referred to as MISR1; SEQ ID NO: 14) are shown in FIG. 1. The full coding sequence of misr2A/misr2B is shown in FIG. 2 (SEQ ID NO: 2), where the overlap between the two cloned sequences is indicated. The full length polypeptide encoded by a DNA sequence resulting from the ligation of appropriate portions of misr2A and misr2B to produce a single, full-length coding sequence is also shown in FIG. 2; this full-length polypeptide is referred to herein as MISR2 (SEQ ID NO: 15). Full-length sequences of clones misr3 and misr4 are shown in FIG. 3 (SEQ ID NO: 3) and FIG. 4 (SEQ ID NO: 4), respectively. The full-length polypeptide encoded by misr3 is termed MISR3 (shown in SEQ ID NO: 16), while the full-length polypeptide encoded by misr4 is termed MISR4 (shown in SEQ ID NO: 17). Each sequence was compared to sequences in the GenBank database, and found to be unique. Misr1 (SEQ ID NO: 1) is believed to encode an isoform of the rat MIS receptor, while misr2A/misr2B (SEQ ID NO: 2), misr3 (SEQ ID NO: 3), and misr4 (SEQ ID NO: 4) are believed to encode monomeric isoforms of the rat inhibin receptor and/or BMP receptor.

Each putative receptor of 501–509 amino acid residues possesses the characteristic domain features of the TGF-β receptor superfamily, including a hydrophobic signal peptide of 19–23 residues (von Heijne, Biochim. Biophys. Acta 947:307, 1988); an extracellular, cysteine-rich, hydrophilic, ligand-binding domain of 100–150 residues, a hydrophobic single transmembrane domain of 23–25 residues (Kyte et al, J. Mol. Biol. 157:105, 1982), an intracellular serine/threonine kinase domain of approximately 300 residues, and a short serine/threonine rich tail. Sequence alignment with the TGF-β and activin type II receptors and daf-1 reveals greatest the similarity between their intracellular domains, including conservation of 22 amino acid residues that are characteristic of the serine/threonine subfamily of protein kinases (Hanks, Meth. Enzymol. 200:38, 1991). All such kinases, including members of the TGF-β receptor family and MISR1–MISR4, have 12 subdomains of highly conserved residues. For example, $GXGXXGXVX_{11-28}K$, conserved in subdomains I and II and thought to form an ATP binding site, aligns well in MISR1–MISR4 as $GKGR(Y/F)GEVX_{12}K$ (SEQ ID NOs: 12 and 13). Subdomains VIB and VIII are key regions which determine tyrosine and serine/threonine kinase specificity; in each of MISR1–MISR4, these domains are more homologous to the serine/threonine motif than to the tyrosine sequence (Hanks et al., Science 241:42–52, 1988).

In situ Hybridization

Plasmids pGEM7-Misr1, pGEM7-Misr2, pGEM7-Misr3, and pGEM7-Misr4 were linearized with appropriate restriction enzymes. Antisense or sense RNA probes labelled with [$^{35}$S]-UTP were generated by transcription of the linearized plasmid DNA using the Riboprobe Gemini System II (Promega Biotech) with SP6 or T7 RNA polymerases.

Tissue sections were postfixed in 4% paraformaldehyde in 0.1M phosphate buffer, pH 7.4, for 5 minutes at room temperature, then rinsed twice in PBS. The sections were rinsed briefly with 0.1M triethanolamine-HCl, pH 8.0, and then treated with 0.25% acetic anhydride in 0.1M triethanolamine-HCl, pH 8.0, for 10 min. at room temperature. The sections were rinsed twice in 2× sodium chloride/sodium citrate (SCC), then dehydrated in increasing concentrations of ethanol, delipidated in chloroform, rehydrated, and air dried for 30 min. at room temperature. Sections were hybridized under coverslips for 15 hours at 55° C. using $^{35}$S-labelled sense or antisense probe ($2\times10^7$ cpm/ml) in 50% formamide, 600 mM NaCl, 10 mM Tris-HCl (pH 7.5), 0.02% Ficoll, 0.02% bovine serum albumin, 0.02% polyvinylpyrrolidone, 1 mM EDTA, 0.01% salmon testis DNA, 0.05% total yeast RNA, 0.005% yeast tRNA, 10% dextran sulfate, 0.1% SDS, 0.1% sodium thiosulfate, and 100 mM DTT. After hybridization, slides were immersed in 2× SSC for 30 min. at room temperature, and floated off the coverslips. The slides were first treated with RNase A (20 mg/ml) in RNase buffer (0.5M NaCl, 10 mM Tris-HCl, pH 8.0, 1.0 mM EDTA) for 30 min. at 37° C. and washed in the same buffer for 30 min. at 37° C. The slides were then washed in 2× SSC for 1 hour at 50° C., 0.2× SSC for 1 hour at 55° C., 0.2× SSC for 1 hour at 60° C., then dehydrated sequentially in 70%, 80%, and 95% ethanol containing 300 mM ammonium acetate, and absolute ethanol before air drying. To detect autoradiographic silver grains, the slides were dipped into Kodak NTB-2 nuclear track emulsion diluted 1:1 with 0.1% Aerosol 22 (Sigma) at 42° C., dried gradually in a high humidity chamber for 2 hours, then exposed at 4° C. for 7–14 days. The slides were developed in Kodak D19 for 2 min. at 16° C., rinsed in deionized water for 30 sec., fixed in Kodak fixer for 5 min., then washed in deionized water and stained with hematoxylin. Sections were examined using bright and darkfield illumination.

To identify potential ligands for MISR1–MISR4 binding studies, in situ hybridization was performed with 13 to 16-day fetal urogenital ridge and fetal, peripubertal, and adult gonads (FIG. 6). Remarkably, misr1 was the only clone to localize specifically to 14.5 to 15-day fetal male Mullerian duct mesenchyme, but not to the adjacent Wolffian duct or gonad or to 13 or 16-day Mullerian tissue. This was a consistent finding using misr1 riboprobes derived from either the 3' conserved domain or the 5' extracellular region, making cross-hybridization with homologous receptors unlikely. In addition, misr1 message localized to oocytes of preantral and antral follicles of the peripubertal and adult ovary. Because the expression and ontogeny of misr1 mRNA is consistent with both the known site (Trelstad et al., Develop. Biol. 92:27–40, 1982; Tsuji et al., Endocrinology 131:1481–1488, 1992) and timing (Picon, Arch. Anat. Micro. Morphol. Exp. 58:1–19, 1969) of MIS action in the urogenital ridge, as well as the cycling adult ovary (Takahashi et al., Molec. Cell. Endocr. 47:225–234, 1986; Ueno et al., Endocrinology 125:1060–1066, 1989), MISR1 is the best candidate for the rat MIS receptor. MISR2 mRNA, on the other hand, localized in a heterogeneous pattern to seminiferous tubules of pubertal and adult testes, but was not detectable within the fetal or adult ovary (FIGS. 6E and 6F). Both MISR1 and MISR2 transcripts were also observed in the postnatal female anterior pituitary and hippocampus (data not shown), but their cellular localization has not been clearly delineated.

Northern Analysis

Northern analysis of a variety of fetal and adult rat tissues was performed to determine both the tissue and temporal specificity of expression of RNA corresponding to each of the four newly identified receptor clones. Total RNA was extracted by a modification of the method of Chirgwin using guanidinium thiocyanate/lithium chloride; RNA quantification was by spectrophotometric analysis and ethidium bromide staining of test gels. Ten μg of total RNA (or in selected cases, 1 μg of poly-A+ RNA) were loaded in each lane of 1.5% Morpholinopropanesulfonic acidformaldehyde agarose gels, electrophoresed at 5 V/cm, transferred to Biotrans nylon membranes (ICN Biomedicals, Irvine, Calif.) by capillary action in 25 mM sodium phosphate, and then fixed by UV irradiation.

Membranes were prehybridized in plaque screen buffer (0.05M Tris-Cl, 0.1% Na pyrophosphate, 1M NaCl, 0.2% polyvinylpyrrolidone, 0.2% Ficoll, 0.2% BSA, 1% SDS) containing 0.1 mg/ml tRNA for 2 hours at 65° C. Membranes were then hybridized with one of the four randomly primed, $^{32}$P-labeled receptor cDNA clones, which varied in length from 0.5 to 3.0 kb. Overnight hybridization was performed with $1\times10^6$ cpm/ml in plaque screening buffer containing 0.1 mg/ml tRNA. All hybridizations and washes were done at 65° C.; 30 mM NaCl/3.0 mM Na citrate/0.5% SDS was the most stringent wash. Autoradiographic exposures were for 3–10 days.

As shown in FIGS. 7A–B, mRNA transcripts of 4.0 kb (misr1), 4.4 and 1.5 kb (misr2A/misr2B), 4.4 kb (misr3), and 6 kb (misr4) were detected in 15-day (E15) fetal urogenital ridge tissue and postnatal day 1 (P1) testis and ovary. Similar levels of expression were found for each clone in pubertal and adult gonads. misr1, misr2, and misr4 message was also abundant in the 21-day (E21) fetal brain, with misr1 mRNA persisting in the adult female brain (data not shown). Interestingly, all four of these mRNAs are present in the E21 lung (particularly misr3 and misr4) and persist there to adulthood (data not shown). Transcripts for misr1 and misr2, and less so for misr3, were detected in other E21 tissues such as the lung, heart, and stomach, suggesting a more universal distribution of these receptors than anticipated.

Identification of TGF-β Type I Receptor

Mink lung epithelial (MvlLu) cells are highly responsive to the effects of TGF-β. Through chemical mutagenesis, several classes of TGF-β resistant MvlLu cell lines have been generated (Boyd et al., J. Biol. Chem. 264:2272, 1989; Laiho et al., J. Biol. Chem., 265:18518, 1990). Mutants of MvlLu cells defective in either the type I (R mutants) or type II (DR mutants) TGF-β receptor lack TGF-β-induced gene responses and TGF-β-induced growth inhibition (Wrana et al., supra; Boyd et al., supra; Laiho et al., supra). A TGF-β reporter construct (p3TP-Lux) containing a TGF-β-inducible promoter controlled luciferase gene was generated to study TGF-β-induced gene responses in MvlLu cell lines (Wrana et al., supra). In a transient assay, transfection of p3TP-Lux into MvlLu cells allows the measurement of TGF-β-dependent induction of luciferase activity. This response is not observed when the assay is performed with either of the TGF-β nonresponsive mutant cell lines. Co-transfection of the human type II TGF-β receptor cDNA along with p3TP-Lux into the DR mutants restores TGF-β inducible gene response (Wrana et al., supra). The same experimental design was used to screen the ability of MISR1–MISR4 to restore a functional TGF-β-induced plasminogen activator inhibitor gene response in a TGF-β nonresponsive MvlLu R mutant cell line, R1B (Boyd et al., supra).

Eukaryotic high-expression vectors (Anderson et al., J. Biol. Chem. 264:8222, 1989) containing the cDNAs encoding MISR1–MISR4 were transiently co-transfected with p3TP-Lux into R1B cells (Wrana et al., supra). Transfectants treated with 240 pM TGF-β1 for 36 hrs were lysed and assayed for luciferase activity. As shown in FIG. 9A, only R1B cells transfected with the MISR4 cDNA showed a high level of TGF-β-dependent luciferase activity. Cells transfected with cDNAs for MISR1–MISR3 showed the same low level of luciferase activity as the negative control cells transfected with the vector alone. The result clearly shows that MISR4 is the only clone capable of restoring a TGF-β inducible gene response in the nonresponsive R1B cells. The level of luciferase activity induced by the MISR4 clone is comparable to that of the DR mutant cells (DR-26) co-transfected with the type II receptor cDNA and p3TP-Lux (FIG. 9B). Furthermore, the magnitude of induction in luciferase activity in MISR4-transfected R1B mutant cells is equivalent to that of the wild-type MvlLu cells (data not shown), indicating that a full TGF-β-induced plasminogen activator inhibitor gene response was restored by transfection of MISR4 into the cells.

The observation that MISR4 expression fully restores a TGF-β-induced plasminogen activator inhibitor gene response to the non-responsive R1B cells which lack endogenous type I receptor expression, strongly suggests that MISR4 is a functional type I TGF-β receptor. Previous studies on the MvlLu mutants have indicated that both the type I and type II receptors are required for TGF-β signaling (Wrana et al., supra). To verify further this conclusion, we tested whether MISR4 was capable of inducing a TGF-β response when transfected into the DR mutants which lack expression of endogenous type II receptor, the DR-26 cells. As shown in FIG. 10A, co-transfection of MISR4 along with p3TP-Lux failed to induce luciferase activity in the presence or the absence of TGF-β. In contrast, co-transfection of the human type II receptor along with p3TP-Lux restored the TGF-β response in a ligand-dependent fashion (FIG. 10A). This result indicates that MISR4 requires the presence of a functional type II TGF-β receptor to transduce the TGF-β signal, and further establishes the molecular nature of MISR4 as a functional type I receptor.

Previous studies with the type II TGF-β receptor in DR mutant cell lines indicated that a functional type II receptor kinase is essential for TGF-β signaling through both the gene activation and growth inhibitory pathways (Wrana et al., supra). We investigated whether the kinase activity of the type I receptor is also required for TGF-β signal transduction. Site-directed mutagenesis of the MISR4 receptor was carried out as follows: Lysine-230 of the ATP-binding site in the kinase domain was mutated to an arginine residue by oligonucleotide site-directed mutagenesis using the unique site elimination system (Pharmacia). Template was generated by subcloning the MISR4 cDNA into the EcoRI side of the pBSK$^+$ vector (Stratagene). A mutagenic oligonucleotide was used to create an arginine codon in place of the lysine-230 codon. The mutation was verified by dideoxy chain termination sequence analysis. This amino acid substitution has been shown to eliminate the kinase activity of known kinases (Hanks et al., Science 241:42, 1988). A high expression vector encoding this kinase-negative K230R MISR4 mutant was transiently co-transfected with the p3TP-Lux reporter plasmid into R1B cells. In contrast to the results with wildtype MISR4, the kinase-negative mutant did not induce luciferase activity in the presence or absence of TGF-β (FIG. 10B). This result demonstrates that the kinase activity of the type I receptor is essential for signaling TGF-β-induced gene responses.

Studies with the MvlLu mutants suggest that TGF-β binding to the type I receptor requires the presence of the type II receptor, while ligand-binding to the type II receptor can occur independently of the type I receptor (Wrana et al., supra). Differences in (a) ability to bind ligand independently and (b) molecular weight for the type types of receptors have been used as distinguishing criteria to classify members of the TGF-β family of receptors into two subtypes. To determine if MISR4 represents a classic type I receptor based on this standard, we examined the ligand binding properties of MISR4 in transfected cells. Since the MvlLu cells are known to be poor recipients for DNA transfection, we performed ligand-binding and crosslinking assays on transiently transfected COS cells. As shown in FIG. 11, radioiodinated TGF-β1-affinity labelling of COS cells transfected with only the MISR4 cDNA showed no additional cross-linked bands when compared to mock transfected COS cells. Cells transfected solely with type II cDNA displayed an increase in intensity for the 85–97 kD band above the background of ligand-binding by endogenous receptors. When MISR4 cDNA was co-transfected with the human type II receptor cDNA, however, a dramatic increase in the amount of labelled proteins migrating as 63–65 kD and 85–97 kD bands was observed. These bands correspond to the classic type I and type II TGF-β receptor proteins. This result demonstrates that MISR4 possesses the binding properties of the type I TGF-β receptor characterized previously (Boyd et al., supra; Mathews et al., Cell 65:973, 1991). The significant increase in binding of TGF-β1 to the type II receptor when the type I receptor was co-expressed suggests that the two receptors may interact to form a complex with a higher ligand-binding affinity than either receptor alone. This observation is in agreement with earlier findings that overexpression of the type II receptor enhanced ligand-binding to the type I receptor (Wang, unpublished result), and the proposed model that the type II receptor gains affinity for TGF-β1 when it binds ligand in concert with the type I receptor (Lopez-Cusillas et al., Cell 73:1435, 1993). It was also found that co-transfection of MISR1 cDNA and type II receptor cDNA results in a slight increase in binding of TGF-β to the 63–65 kD protein (data not shown), a result consistent with published data (Ebner et al., Science 260:1344, 1993).

The type II TGF-β receptor was shown to be an active kinase capable of autophosphorylation in an in vitro kinase assay (FIGS. 12A and 12B). Since the cytoplasmic domain of MISR4 also contains a putative serine-threonine kinase domain which shares significant (41%) homology with the type II receptor kinase, it was of interest to determine whether MISR4 could act as a functional serine-threonine kinase in vitro. A fusion protein containing glutathione-S-transferase linked to the type I receptor cytoplasmic domain was generated as follows: To create the in frame fusion protein, a portion of MISR4 cDNA encoding the cytoplasmic domain (between Asp161 and the carboxy terminal end of the protein) was subcloned into plasmid pGEX-1. In vitro kinase assays were performed with the proteins bound to glutathione (GT) beads in 50 mM Tris pH 7.4, 150 mM NaCl, 1 mM $MgCl_2$, 1 mM $MnCl_2$, 1 mM $Na_2MoO_4$, 2 mM NaF, 1 mM DTT and 10 uCi [$^{32}$p-θ]ATP at 30° C. for 40 min.]). As a control, we constructed a similar fusion protein using the MISR4 cytoplasmic domain containing the K230R null kinase mutation. The fusion protein containing the wild-type MISR4 kinase domain (GST-R4 WT) was found to possess kinase activity in the in vitro kinase assay, while the second fusion protein containing the mutated MISR4 kinase domain (GST-R4 K230R) was incapable of autophosphorylation (FIG. 12A). In parallel experiments, a comparable TGF-β type II receptor kinase domain fusion protein (GST-RII WT) showed four times more activity than the GST-R4 WT MISR4 kinase domain fusion protein (FIG. 12A). Similarly, a fusion protein containing the MISR1 kinase domain was generated and assayed for autophosphorylation activity. It was found to be approximately 100-fold less active than the type II receptor kinase domain fusion protein (data not shown). This result suggests that the MISR4 type I receptor, like the type II receptor, can function as a serine-threonine kinase in vitro. The similar levels of kinase activity in vitro suggest that neither the type I nor the type II receptor plays a dominant role in transducing signals from the receptor complex.

Previous phospho-amino acid analysis of the GST-RII fusion protein showed the type II receptor to be mainly a serine kinase with a small amount of threonine activity (Lin et al., Cell 68:1, 1992). Phospho-amino acid analysis of the GST-R4 fusion protein kinase reaction products revealed mainly phospho-threonine, with a small amount of phosphoserine (FIG. 12B). It should be emphasized that this result does not rule out the possibility that the type I and/or the type II receptor may be induced to undergo tyrosine phosphorylation under specific conditions. In unpublished work, the kinase of TGF-β type II receptor has been found to be capable of tyrosine autophosphorylation in vitro when certain deletion and point mutations are introduced into the kinase domain, suggesting that activation of tyrosine phosphorylation activity may involve conformational changes in the receptor. It is thus possible that tyrosine autophosphorylation of the TGF-β receptor complex may occur in vivo, perhaps as a result of a ligand-induced conformational change, and could play an important role in TGF-β induced signal transduction.

R1B cells have lost both the gene activation and the growth inhibition responses of wildtype MvlLu cells to TGF-β. To determine whether MISR4 could restore the growth inhibition pathway in these cells, MISR4 cDNA and a plasmid carrying a selectable marker were co-transfected into the R1B cells, in an attempt to establish a stable R1B cell line that expresses the MISR4 protein. This was carried out as follows: plasmids pCMV6-R4 (50 ug) and pBabePuro (2 ug) were co-transfected into R1B mutant cells using LipofectAMINE™, in accordance with the protocol provided by the manufacturer (Gibco-BRL). Colonies were selected with 0.4 ug/ml puromycin. After two weeks of drug selection, several dozen stable clones were grown out and analyzed for inhibition of DNA synthesis by TGF-β. In our initial experiment, only one of these stable lines, R1B-R4(41), displayed a significant TGF-β-dependent growth inhibition. The magnitude of inhibition (82%) was equivalent to the response by wild-type MvlLu cells in the same experiment. This preliminary observation suggests that expressing the MISR4 type I receptor in type 1-deficient R1B cells restores both gene activation and growth inhibition responses.

Because the transfected cells have an extremely slow growth rate, the growth inhibition assay could not be repeated until two weeks later. Within the interim, however, it was found that the R1B-MISR4(41) cells had changed morphology and lost the growth-inhibitory response to TGF-β. This intriguing and puzzling phenomenon, combined with the observation that only one of the grown-out colonies did not expressed the introduced type I receptor and was nonresponsive to TGF-β growth inhibition, suggests that the expression of MISR4 at high levels results in a growth disadvantage to the cells during the colony selection and expansion process. This tentative conclusion was further supported by evidence that there were two populations of colonies with drastically different morphological phenotypes observed during the selection. The first class contained fast growing cells with morphology similar to that of the parental R1B cells. The second class contained very slow growing cells that were comparatively enlarged and flattened, relative to the parental cells. Most of the colonies that eventually grew changed their phenotype to become fast growing cells during colony expansion. It can be assumed that the first class of cells contained only the drug-resistant gene, while the second class, to which the R1B-R4(41) clone initially belonged, represented cells that expressed the MISR4 gene. This difference in cell morphology was not observed when the MISR4 mutant gene with a null kinase was introduced into the R1B cells. This abnormal growth phenotype, apparently derived from overexpression of the wild-type type I receptor, is likely to be a reflection of the signaling mechanism involving receptor complex formation and activation/inactivation of downstream growth regulatory pathways.

MISR4 appears to be a functional type I TGF-β receptor, based on the following criteria: it can restore a TGF-β-induced gene response in the nonresponsive R1B mutant cells which lack an endogenous functional type I receptor; it requires the presence of a functional type II receptor to bind ligand and to signal; its kinase activity is required for signaling; and the kinase domain is capable of serine-threonine autophosphorylation under in vitro conditions. The interactions between TGF-β type I and type II receptors are likely to involve both autophosphorylation and transphosphorylation events within the heteromeric complex. The lack of dominance of either kinase suggests that the activity of each receptor could be modulated by its partner in the complex. It is also possible that MISR4 represents only one of multiple functional type I receptors for TGF-β.

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 1530
        ( B ) TYPE: nucleic acid
        ( C ) STRANDEDNESS: double (D) TOPOLOGY: linear (xi) SEQUENCE DESCRIPTION: SEQ ID NO: 1:

| | | | | | | | | | | | | | | | | |
|---|---|---|---|---|---|---|---|---|---|---|---|---|---|---|---|---|
| ATG | GTC | GAT | GGA | GCA | ATG | ATC | CTT | TCT | GTG | CTA | ATG | ATG | ATG | GCT | CTC | 48 |
| Met | Val | Asp | Gly | Ala | Met | Ile | Leu | Ser | Val | Leu | Met | Met | Met | Ala | Leu | |
| 1 | | | | 5 | | | | | 10 | | | | | 15 | | |
| CCT | TCC | CCG | AGT | ATG | GAA | GAT | GAG | GAG | CCC | AAG | GTC | AAC | CCG | AAG | CTT | 96 |
| Pro | Ser | Pro | Ser | Met | Glu | Asp | Glu | Glu | Pro | Lys | Val | Asn | Pro | Lys | Leu | |
| | | | 20 | | | | | 25 | | | | | 30 | | | |
| TAC | ATG | TGT | GTG | TGT | GAG | GGC | CTC | TCC | TGC | GGG | AAC | GAG | GAC | CAC | TGT | 144 |
| Tyr | Met | Cys | Val | Cys | Glu | Gly | Leu | Ser | Cys | Gly | Asn | Glu | Asp | His | Cys | |
| | | 35 | | | | | 40 | | | | | 45 | | | | |
| GAG | GGC | CAG | CAG | TGT | TTT | TCC | TCC | CTG | AGC | GTC | AAT | GAT | GGC | TTC | CGC | 192 |
| Glu | Gly | Gln | Gln | Cys | Phe | Ser | Ser | Leu | Ser | Val | Asn | Asp | Gly | Phe | Arg | |
| | 50 | | | | | 55 | | | | | 60 | | | | | |
| GTC | TAC | CAG | AAG | GGC | TGC | TTT | CAG | GTC | TAT | GAG | CAG | GGG | AAG | ATG | ACG | 240 |
| Val | Tyr | Gln | Lys | Gly | Cys | Phe | Gln | Val | Tyr | Glu | Gln | Gly | Lys | Met | Thr | |
| 65 | | | | | 70 | | | | | 75 | | | | | 80 | |
| TGT | AAG | ACC | CCG | CCG | TCG | CCT | GGC | CAG | GCT | GTG | GAG | TGC | TGC | CAA | GGG | 288 |
| Cys | Lys | Thr | Pro | Pro | Ser | Pro | Gly | Gln | Ala | Val | Glu | Cys | Cys | Gln | Gly | |
| | | | | 85 | | | | | 90 | | | | | 95 | | |
| GAC | TGG | TGC | AAC | AGG | AAC | GTC | ACG | GCC | CGG | CTG | CCC | ACT | AAA | GGG | AAA | 336 |
| Asp | Trp | Cys | Asn | Arg | Asn | Val | Thr | Ala | Arg | Leu | Pro | Thr | Lys | Gly | Lys | |
| | | | 100 | | | | | 105 | | | | | 110 | | | |
| TCC | TTC | CCT | GGA | TCG | CAG | AAC | TTC | CAC | CTG | GAA | GTT | GGC | CTT | ATC | ATC | 384 |
| Ser | Phe | Pro | Gly | Ser | Gln | Asn | Phe | His | Leu | Glu | Val | Gly | Leu | Ile | Ile | |
| | | 115 | | | | | 120 | | | | | 125 | | | | |
| CTC | TCC | GTG | GTG | TTT | GCG | GTA | TGC | CTT | TTC | GCT | TGC | ATC | CTT | GGC | GTT | 432 |
| Leu | Ser | Val | Val | Phe | Ala | Val | Cys | Leu | Phe | Ala | Cys | Ile | Leu | Gly | Val | |
| | 130 | | | | | 135 | | | | | 140 | | | | | |
| GCT | CTC | AGG | AAG | TTT | AAA | AGG | CGC | AAT | CAA | GAG | CGC | CTG | AAC | CCC | AGA | 480 |
| Ala | Leu | Arg | Lys | Phe | Lys | Arg | Arg | Asn | Gln | Glu | Arg | Leu | Asn | Pro | Arg | |
| 145 | | | | | 150 | | | | | 155 | | | | | 160 | |
| GAC | GTG | GAG | TAC | GGT | ACT | ATC | GAA | GGG | CTC | ATC | ACC | ACC | AAC | GTC | GGA | 528 |
| Asp | Val | Glu | Tyr | Gly | Thr | Ile | Glu | Gly | Leu | Ile | Thr | Thr | Asn | Val | Gly | |
| | | | | 165 | | | | | 170 | | | | | 175 | | |
| GAT | AGC | ACT | CTA | GCG | GAA | TTA | CTA | GAT | CAC | TCG | TGT | ACA | TCA | GGA | AGT | 576 |
| Asp | Ser | Thr | Leu | Ala | Glu | Leu | Leu | Asp | His | Ser | Cys | Thr | Ser | Gly | Ser | |
| | | | 180 | | | | | 185 | | | | | 190 | | | |
| GGC | TCC | GGT | CTT | CCT | TTT | CTG | GTA | CAG | AGA | ACT | GTG | GCT | CGA | CAG | ATA | 624 |
| Gly | Ser | Gly | Leu | Pro | Phe | Leu | Val | Gln | Arg | Thr | Val | Ala | Arg | Gln | Ile | |
| | | 195 | | | | | 200 | | | | | 205 | | | | |
| ACC | CTG | TTG | GAG | TGT | GTC | GGG | AAG | GGC | CGG | TAT | GGA | GAA | GTG | TGG | AGG | 672 |
| Thr | Leu | Leu | Glu | Cys | Val | Gly | Lys | Gly | Arg | Tyr | Gly | Glu | Val | Trp | Arg | |
| | 210 | | | | | 215 | | | | | 220 | | | | | |
| GGC | AGC | TGG | CAA | GGC | GAA | AAT | GTT | GCT | GTG | AAG | ATC | TTC | TCC | TCC | CGT | 720 |
| Gly | Ser | Trp | Gln | Gly | Glu | Asn | Val | Ala | Val | Lys | Ile | Phe | Ser | Ser | Arg | |
| 225 | | | | | 230 | | | | | 235 | | | | | 240 | |
| GAT | GAG | AAG | TCG | TGG | TTC | AGG | GAG | ACA | GAA | TTG | TAC | AAC | ACG | GTG | ATG | 768 |
| Asp | Glu | Lys | Ser | Trp | Phe | Arg | Glu | Thr | Glu | Leu | Tyr | Asn | Thr | Val | Met | |
| | | | | 245 | | | | | 250 | | | | | 255 | | |
| CTG | AGG | CAT | GAG | AAT | ATC | TTA | GGT | TTC | ATT | GCT | TCA | GAC | ATG | ACC | TCT | 816 |
| Leu | Arg | His | Glu | Asn | Ile | Leu | Gly | Phe | Ile | Ala | Ser | Asp | Met | Thr | Ser | |
| | | | 260 | | | | | 265 | | | | | 270 | | | |
| AGA | CAC | TCC | AGT | ACC | CAG | CTG | TGG | CTC | ATT | ACA | CAT | TAC | CAC | GAA | ATG | 864 |
| Arg | His | Ser | Ser | Thr | Gln | Leu | Trp | Leu | Ile | Thr | His | Tyr | His | Glu | Met | |
| | | 275 | | | | | 280 | | | | | 285 | | | | |
| GGA | TCG | TTG | TAT | GAC | TAC | CTT | CAG | CTC | ACC | ACT | CTG | GAC | ACG | GTT | AGC | 912 |
| Gly | Ser | Leu | Tyr | Asp | Tyr | Leu | Gln | Leu | Thr | Thr | Leu | Asp | Thr | Val | Ser | |
| | | 290 | | | | | 295 | | | | | 300 | | | | |

| | | | | | | | | | | | | | | | | |
|---|---|---|---|---|---|---|---|---|---|---|---|---|---|---|---|---|
| TGC | CTT | CGG | ATC | GTG | TTG | TCC | ATA | GCC | AGC | GGC | CTT | GCA | CAC | TTG | CAC | 960 |
| Cys | Leu | Arg | Ile | Val | Leu | Ser | Ile | Ala | Ser | Gly | Leu | Ala | His | Leu | His | |
| 305 | | | | 310 | | | | | 315 | | | | | | 320 | |
| ATA | GAG | ATA | TTT | GGG | ACC | CAG | GGG | AAG | TCT | GCC | ATC | GCC | CAC | CGA | GAT | 1008 |
| Ile | Glu | Ile | Phe | Gly | Thr | Gln | Gly | Lys | Ser | Ala | Ile | Ala | His | Arg | Asp | |
| | | | | 325 | | | | | 330 | | | | | 335 | | |
| CTA | AAG | AGC | AAA | AAC | ATC | CTC | GTG | AAG | AAG | AAC | GGA | CAG | TGC | TGC | ATA | 1056 |
| Leu | Lys | Ser | Lys | Asn | Ile | Leu | Val | Lys | Lys | Asn | Gly | Gln | Cys | Cys | Ile | |
| | | | 340 | | | | | 345 | | | | | 350 | | | |
| GCA | GAT | TTG | GGC | CTG | GCA | GTC | ATG | CAT | TCC | CAG | AGC | ACG | AAT | CAG | CTT | 1104 |
| Ala | Asp | Leu | Gly | Leu | Ala | Val | Met | His | Ser | Gln | Ser | Thr | Asn | Gln | Leu | |
| | | 355 | | | | | 360 | | | | | 365 | | | | |
| GAT | GTG | GGA | AAC | AAC | CCC | CGT | GTG | GGG | ACC | AAG | CGC | TAC | ATG | GCC | CCT | 1152 |
| Asp | Val | Gly | Asn | Asn | Pro | Arg | Val | Gly | Thr | Lys | Arg | Tyr | Met | Ala | Pro | |
| | 370 | | | | | 375 | | | | | 380 | | | | | |
| GAA | GTG | CTT | GAT | GAA | ACC | ATC | CAA | GTG | GAT | TGC | TTT | GAT | TCT | TAT | AAG | 1200 |
| Glu | Val | Leu | Asp | Glu | Thr | Ile | Gln | Val | Asp | Cys | Phe | Asp | Ser | Tyr | Lys | |
| 385 | | | | | 390 | | | | | 395 | | | | | 410 | |
| AGG | GTC | GAT | ATT | TGG | GCC | TTT | GGC | CTC | GTT | CTG | TGG | GAA | GTG | GCC | AGG | 1248 |
| Arg | Val | Asp | Ile | Trp | Ala | Phe | Gly | Leu | Val | Leu | Trp | Glu | Val | Ala | Arg | |
| | | | | 415 | | | | | 420 | | | | | 425 | | |
| AGG | ATG | GTG | AGC | AAT | GGT | ATA | GTG | GAA | GAT | TAC | AAG | CCA | CCA | TTC | TAT | 1296 |
| Arg | Met | Val | Ser | Asn | Gly | Ile | Val | Glu | Asp | Tyr | Lys | Pro | Pro | Phe | Tyr | |
| | | | 430 | | | | | 435 | | | | | 440 | | | |
| GAT | GTT | GTT | CCC | AAT | GAC | CCA | AGT | TTT | GAA | GAT | ATG | AGG | AAA | GTT | GTC | 1344 |
| Asp | Val | Val | Pro | Asn | Asp | Pro | Ser | Phe | Glu | Asp | Met | Arg | Lys | Val | Val | |
| | | 445 | | | | | 450 | | | | | 455 | | | | |
| TGT | GTG | GAT | CAA | CAG | AGG | CCA | AAC | ATA | CCT | AAC | AGA | TGG | TTC | TCA | GAC | 1392 |
| Cys | Val | Asp | Gln | Gln | Arg | Pro | Asn | Ile | Pro | Asn | Arg | Trp | Phe | Ser | Asp | |
| | 460 | | | | | 465 | | | | | 470 | | | | | |
| CCG | ACA | TTA | ACT | TCT | CTG | GCG | AAC | GTG | ATG | AAA | GAA | TGC | TGG | TAC | CAG | 1440 |
| Pro | Thr | Leu | Thr | Ser | Leu | Ala | Asn | Val | Met | Lys | Glu | Cys | Trp | Tyr | Gln | |
| 475 | | | | | 480 | | | | | 485 | | | | | 490 | |
| AAC | CCA | TCC | GCC | AGA | CTC | ACA | GCT | CTA | CGT | ATC | AAA | AAG | ACT | TTG | ACC | 1488 |
| Asn | Pro | Ser | Ala | Arg | Leu | Thr | Ala | Leu | Arg | Ile | Lys | Lys | Thr | Leu | Thr | |
| | | | | 495 | | | | 500 | | | | | 505 | | | |
| AAA | ATT | GAT | AAC | TCC | CTA | GAC | AAA | TTA | AAA | ACT | GAC | TGT | TGA | | | 1530 |
| Lys | Ile | Asp | Asn | Ser | Leu | Asp | Lys | Leu | Lys | Thr | Asp | Cys | | | | |
| | | | 510 | | | | | 515 | | | | | | | | |

( 2 ) INFORMATION FOR SEQ ID NO: 2:

( i ) SEQUENCE CHARACTERISTICS:
        ( A ) LENGTH: 1506
        ( B ) TYPE: nucleic acid
        ( C ) STRANDEDNESS: double
        ( D ) TOPOLOGY: linear ( x i ) SEQUENCE DESCRIPTION: SEQ ID NO: 2:

| | | | | | | | | | | | | | | | | |
|---|---|---|---|---|---|---|---|---|---|---|---|---|---|---|---|---|
| ATG | GCG | GAG | TCG | GCC | GGA | GCC | TCC | TCC | TTC | TTC | CCC | CTT | GTT | GTC | CTC | 48 |
| Met | Ala | Glu | Ser | Ala | Gly | Ala | Ser | Ser | Phe | Phe | Pro | Leu | Val | Val | Leu | |
| 1 | | | | 5 | | | | | 10 | | | | | 15 | | |
| CTG | CTC | GCC | GGC | AGT | GGC | GGG | TCC | GGG | CCC | CGG | GGG | ATC | CAG | GCT | CTG | 96 |
| Leu | Leu | Ala | Gly | Ser | Gly | Gly | Ser | Gly | Pro | Arg | Gly | Ile | Gln | Ala | Leu | |
| | | | | 20 | | | | | 25 | | | | | 30 | | |
| CTG | TGT | GCA | TGC | ACC | AGC | TGC | CTA | CAG | ACC | AAC | TAC | ACC | TGC | GAA | ACA | 144 |
| Leu | Cys | Ala | Cys | Thr | Ser | Cys | Leu | Gln | Thr | Asn | Tyr | Thr | Cys | Glu | Thr | |
| | | | 35 | | | | | 40 | | | | | 45 | | | |
| GAT | GGG | GCC | TGC | ATG | GTC | TCC | ATC | TTT | AAC | CTG | GAT | GGC | ATG | GAG | CAC | 192 |
| Asp | Gly | Ala | Cys | Met | Val | Ser | Ile | Phe | Asn | Leu | Asp | Gly | Met | Glu | His | |
| | | 50 | | | | | 55 | | | | | 60 | | | | |
| | CAC | GTA | CGC | ACC | TGC | ATC | CCC | AAG | GTG | GAG | CTT | GTG | CCT | GCT | GGG | AAG | 240 |

| | | | | | | | | | | | | | | | | |
|---|---|---|---|---|---|---|---|---|---|---|---|---|---|---|---|---|
| His | Val | Arg | Thr | Cys | Ile | Pro | Lys | Val | Glu | Leu | Val | Pro | Ala | Gly | Lys | |
| 65 | | | | 70 | | | | | 75 | | | | | | 80 | |
| CCC | TTC | TAC | TGC | CTG | AGT | TCA | GAG | GAC | CTG | CGC | AAC | ACG | CAC | TGC | TGC | 288 |
| Pro | Phe | Tyr | Cys | Leu | Ser | Ser | Glu | Asp | Leu | Arg | Asn | Thr | His | Cys | Cys | |
| | | | | 85 | | | | | 90 | | | | | 95 | | |
| TAT | ATT | GAC | TTC | TGC | AAC | AAG | ATT | GAC | CTG | AGG | GTG | CCC | AGT | GGA | CAC | 336 |
| Tyr | Ile | Asp | Phe | Cys | Asn | Lys | Ile | Asp | Leu | Arg | Val | Pro | Ser | Gly | His | |
| | | | 100 | | | | | 105 | | | | | 110 | | | |
| CTC | AAG | GAG | CCT | GAG | CAC | CCC | TCC | ATG | TGG | GGC | CCT | GTG | GAG | CTG | GTC | 384 |
| Leu | Lys | Glu | Pro | Glu | His | Pro | Ser | Met | Trp | Gly | Pro | Val | Glu | Leu | Val | |
| | | 115 | | | | | 120 | | | | | 125 | | | | |
| GGC | ATC | ATT | GCC | GGT | CCT | GTC | TTC | CTC | CTC | TTC | CTC | ATC | ATC | ATC | ATC | 432 |
| Gly | Ile | Ile | Ala | Gly | Pro | Val | Phe | Leu | Leu | Phe | Leu | Ile | Ile | Ile | Ile | |
| 130 | | | | | 135 | | | | | 140 | | | | | | |
| GTC | TTC | CTG | GTC | ATC | AAC | TAT | CAT | CAG | CGT | GTC | TAC | CAC | AAC | CGC | CAA | 480 |
| Val | Phe | Leu | Val | Ile | Asn | Tyr | His | Gln | Arg | Val | Tyr | His | Asn | Arg | Gln | |
| 145 | | | | | 150 | | | | | 155 | | | | | 160 | |
| AGA | CTG | GAC | ATG | GAG | GAC | CCC | TCA | TGT | GAG | ATG | TGT | CTC | TCC | AAA | GAC | 528 |
| Arg | Leu | Asp | Met | Glu | Asp | Pro | Ser | Cys | Glu | Met | Cys | Leu | Ser | Lys | Asp | |
| | | | | 165 | | | | | 170 | | | | | 175 | | |
| AAG | ACG | CTC | CAG | GAT | CTC | GTC | TAC | GAT | CTC | TCC | ACT | TCA | GGA | TCG | GGC | 576 |
| Lys | Thr | Leu | Gln | Asp | Leu | Val | Tyr | Asp | Leu | Ser | Thr | Ser | Gly | Ser | Gly | |
| | | | 180 | | | | | 185 | | | | | 190 | | | |
| TCA | GGG | TTA | CCC | CTT | TTT | GTC | CAG | CGC | ACA | GTG | GCC | CGA | ACC | ATT | GTT | 624 |
| Ser | Gly | Leu | Pro | Leu | Phe | Val | Gln | Arg | Thr | Val | Ala | Arg | Thr | Ile | Val | |
| | | 195 | | | | | 200 | | | | | 205 | | | | |
| TTA | CAA | GAG | ATT | ATC | GGC | AAG | GGC | CGG | TTT | GGG | GAA | GTA | TGG | CGT | GGC | 672 |
| Leu | Gln | Glu | Ile | Ile | Gly | Lys | Gly | Arg | Phe | Gly | Glu | Val | Trp | Arg | Gly | |
| 210 | | | | | 215 | | | | | 220 | | | | | | |
| CGC | TGG | AGG | GGT | GGT | GAT | GTG | GCT | GTG | AAA | ATC | TTC | TCT | TCC | CGT | GAA | 720 |
| Arg | Trp | Arg | Gly | Gly | Asp | Val | Ala | Val | Lys | Ile | Phe | Ser | Ser | Arg | Glu | |
| 225 | | | | | 230 | | | | | 235 | | | | | 240 | |
| GAG | CGG | TCG | TGG | TTC | CGG | GAG | GCA | GAG | ATC | TAC | CAG | ACT | GTC | ATG | CTG | 768 |
| Glu | Arg | Ser | Trp | Phe | Arg | Glu | Ala | Glu | Ile | Tyr | Gln | Thr | Val | Met | Leu | |
| | | | | 245 | | | | | 250 | | | | | 255 | | |
| CGC | CAT | GAA | AAC | ATC | CTT | GGG | TTT | ATT | GCT | GCT | GAC | AAT | AAA | GAC | AAT | 816 |
| Arg | His | Glu | Asn | Ile | Leu | Gly | Phe | Ile | Ala | Ala | Asp | Asn | Lys | Asp | Asn | |
| | | | 260 | | | | | 265 | | | | | 270 | | | |
| GGC | ACC | TGG | ACC | CAG | CTG | TGG | CTT | GTC | TCT | GAC | TAT | CAC | GAG | CAC | GGC | 864 |
| Gly | Thr | Trp | Thr | Gln | Leu | Trp | Leu | Val | Ser | Asp | Tyr | His | Glu | His | Gly | |
| | | 275 | | | | | 280 | | | | | 285 | | | | |
| TCA | CTG | TTC | GAT | TAT | CTG | AAC | CGC | TAC | ACA | GTG | ACC | ATT | GAG | GGG | ATG | 912 |
| Ser | Leu | Phe | Asp | Tyr | Leu | Asn | Arg | Tyr | Thr | Val | Thr | Ile | Glu | Gly | Met | |
| | 290 | | | | | 295 | | | | | 300 | | | | | |
| ATT | AAA | CTG | GCC | CTG | TCT | GCA | GCC | AGT | GGT | TTG | GCA | CAC | CTG | CAT | ATG | 960 |
| Ile | Lys | Leu | Ala | Leu | Ser | Ala | Ala | Ser | Gly | Leu | Ala | His | Leu | His | Met | |
| 305 | | | | | 310 | | | | | 315 | | | | | 320 | |
| GAG | ATT | GTG | GGC | ACT | CAG | GGG | AAG | CCT | GGA | ATT | GCT | CAT | CGA | GAC | TTG | 1008 |
| Glu | Ile | Val | Gly | Thr | Gln | Gly | Lys | Pro | Gly | Ile | Ala | His | Arg | Asp | Leu | |
| | | | | 325 | | | | | 330 | | | | | 335 | | |
| AAG | TCA | AAG | AAC | ATT | CTG | GTG | AAG | AAG | AAT | GGC | ATG | TGT | GCC | ATT | GCA | 1056 |
| Lys | Ser | Lys | Asn | Ile | Leu | Val | Lys | Lys | Asn | Gly | Met | Cys | Ala | Ile | Ala | |
| | | | 340 | | | | | 345 | | | | | 350 | | | |
| GAC | CTG | GGC | CTA | GCT | GTC | CGT | CAC | GAT | GCT | GTC | ACT | GAC | ACC | ATA | GAC | 1104 |
| Asp | Leu | Gly | Leu | Ala | Val | Arg | His | Asp | Ala | Val | Thr | Asp | Thr | Ile | Asp | |
| | | 355 | | | | | 360 | | | | | 365 | | | | |
| ATT | GCT | CCA | AAT | CAG | AGG | GTG | GGA | ACC | AAA | CGA | TAC | ATG | GCT | CCT | GAA | 1152 |
| Ile | Ala | Pro | Asn | Gln | Arg | Val | Gly | Thr | Lys | Arg | Tyr | Met | Ala | Pro | Glu | |
| | 370 | | | | | 375 | | | | | 380 | | | | | |
| GTA | CTT | GAC | GAG | ACC | ATC | AAC | ATG | AAG | CAC | TTT | GAC | TCC | TTC | AAG | TGT | 1200 |

| | | | | | | | | | | | | | | | | |
|---|---|---|---|---|---|---|---|---|---|---|---|---|---|---|---|---|
| Val | Leu | Asp | Glu | Thr | Ile | Asn | Met | Lys | His | Phe | Asp | Ser | Phe | Lys | Cys | |
| 385 | | | | 390 | | | | | 395 | | | | | | 400 | |

| GCC | GAT | ATC | TAC | GCC | CTC | GGG | CTT | GTC | TAT | TGG | GAG | ATT | GCT | CGG | AGG | 1248 |
|---|---|---|---|---|---|---|---|---|---|---|---|---|---|---|---|---|
| Ala | Asp | Ile | Tyr | Ala | Leu | Gly | Leu | Val | Tyr | Trp | Glu | Ile | Ala | Arg | Arg | |
| | | | | 405 | | | | | 410 | | | | | 415 | | |

| TGC | AAT | TCT | GGA | GGA | GTC | CAT | GAA | GAG | TAT | CAA | CTG | CCA | TAT | TAT | GAT | 1296 |
|---|---|---|---|---|---|---|---|---|---|---|---|---|---|---|---|---|
| Cys | Asn | Ser | Gly | Gly | Val | His | Glu | Glu | Tyr | Gln | Leu | Pro | Tyr | Tyr | Asp | |
| | | | 420 | | | | | 425 | | | | | 430 | | | |

| TTA | GTG | CCC | TCT | GAC | CCT | TCC | ATT | GAG | GAA | ATG | CGA | AAG | GTC | GTC | TGT | 1344 |
|---|---|---|---|---|---|---|---|---|---|---|---|---|---|---|---|---|
| Leu | Val | Pro | Ser | Asp | Pro | Ser | Ile | Glu | Glu | Met | Arg | Lys | Val | Val | Cys | |
| | | 435 | | | | | 440 | | | | | 445 | | | | |

| GAC | CAG | AAG | CTA | CGG | CCC | AAT | GTC | CCC | AAC | TGG | TGG | CAG | AGT | TAT | GAG | 1392 |
|---|---|---|---|---|---|---|---|---|---|---|---|---|---|---|---|---|
| Asp | Gln | Lys | Leu | Arg | Pro | Asn | Val | Pro | Asn | Trp | Trp | Gln | Ser | Tyr | Glu | |
| | 450 | | | | | 455 | | | | | 460 | | | | | |

| GCC | TTG | CGA | GTG | ATG | GGG | AAG | ATG | ATG | CGG | GAG | TGC | TGG | TAC | GCC | AAT | 1440 |
|---|---|---|---|---|---|---|---|---|---|---|---|---|---|---|---|---|
| Ala | Leu | Arg | Val | Met | Gly | Lys | Met | Met | Arg | Glu | Cys | Trp | Tyr | Ala | Asn | |
| 465 | | | | | 470 | | | | | 475 | | | | | 480 | |

| GGT | GCT | GCC | CGC | CTG | ACA | GCG | CTG | CGC | ATC | AAG | AAG | ACT | TTG | TCC | CAG | 1488 |
|---|---|---|---|---|---|---|---|---|---|---|---|---|---|---|---|---|
| Gly | Ala | Ala | Arg | Leu | Thr | Ala | Leu | Arg | Ile | Lys | Lys | Thr | Leu | Ser | Gln | |
| | | | | 485 | | | | 490 | | | | | | 495 | | |

| GAA | GAC | GTG | AAG | ATT | TAA | | | | | | | | | | | 1506 |
|---|---|---|---|---|---|---|---|---|---|---|---|---|---|---|---|---|
| Glu | Asp | Val | Lys | Ile | | | | | | | | | | | | |
| | | | | 500 | | | | | | | | | | | | |

( 2 ) INFORMATION FOR SEQ ID NO: 3:

( i ) SEQUENCE CHARACTERISTICS:
        ( A ) LENGTH: 1518
        ( B ) TYPE: nucleic acid
        ( C ) STRANDEDNESS: double
        ( D ) TOPOLOGY: linear ( x i ) SEQUENCE DESCRIPTION: SEQ ID NO: 3:

| ATG | ACC | CTG | GGG | ATT | TTT | CGA | AGG | GTC | TTT | TTG | ATG | CTG | TCG | GTG | GCC | 48 |
|---|---|---|---|---|---|---|---|---|---|---|---|---|---|---|---|---|
| Met | Thr | Leu | Gly | Ile | Phe | Arg | Arg | Val | Phe | Leu | Met | Leu | Ser | Val | Ala | |
| 1 | | | | 5 | | | | | 10 | | | | | 15 | | |

| TTG | GGC | CTA | ACT | AAG | GGA | GAC | TTG | GTG | AAG | CCC | TCC | AGG | GGT | CAG | CTG | 96 |
|---|---|---|---|---|---|---|---|---|---|---|---|---|---|---|---|---|
| Leu | Gly | Leu | Thr | Lys | Gly | Asp | Leu | Val | Lys | Pro | Ser | Arg | Gly | Gln | Leu | |
| | | | 20 | | | | | 25 | | | | | 30 | | | |

| GTA | AAC | TGC | ACT | TGT | GAG | AAC | CCA | CAC | TGC | AAG | AGG | CCA | ATC | TGC | CAG | 144 |
|---|---|---|---|---|---|---|---|---|---|---|---|---|---|---|---|---|
| Val | Asn | Cys | Thr | Cys | Glu | Asn | Pro | His | Cys | Lys | Arg | Pro | Ile | Cys | Gln | |
| | | 35 | | | | | 40 | | | | | 45 | | | | |

| GGG | GCA | TGG | TGC | ACA | GTG | GTG | CTA | GTT | CGA | GAG | CAG | GGC | AGG | CAC | CCC | 192 |
|---|---|---|---|---|---|---|---|---|---|---|---|---|---|---|---|---|
| Gly | Ala | Trp | Cys | Thr | Val | Val | Leu | Val | Arg | Glu | Gln | Gly | Arg | His | Pro | |
| | 50 | | | | | 55 | | | | | 60 | | | | | |

| CAG | GTC | TAT | CGG | GGC | TGC | GGG | AGC | CTG | AAC | CAG | GAG | CTC | TGC | CTG | GGA | 240 |
|---|---|---|---|---|---|---|---|---|---|---|---|---|---|---|---|---|
| Gln | Val | Tyr | Arg | Gly | Cys | Gly | Ser | Leu | Asn | Gln | Glu | Leu | Cys | Leu | Gly | |
| 65 | | | | 70 | | | | | 75 | | | | | 80 | | |

| CGT | CCC | ACG | GAG | TTT | GTG | AAC | CAT | CAC | TGC | TGC | TAT | AGA | TCC | TTC | TGC | 288 |
|---|---|---|---|---|---|---|---|---|---|---|---|---|---|---|---|---|
| Arg | Pro | Thr | Glu | Phe | Val | Asn | His | His | Cys | Cys | Tyr | Arg | Ser | Phe | Cys | |
| | | | | 85 | | | | | 90 | | | | | 95 | | |

| AAC | CAC | AAT | GTG | TCC | CTG | ATG | CTG | GAG | GCC | ACC | CAA | ACT | CCT | TCG | GAG | 336 |
|---|---|---|---|---|---|---|---|---|---|---|---|---|---|---|---|---|
| Asn | His | Asn | Val | Ser | Leu | Met | Leu | Glu | Ala | Thr | Gln | Thr | Pro | Ser | Glu | |
| | | | 100 | | | | | 105 | | | | | 110 | | | |

| GAG | CCA | GAA | GTA | GAT | GCC | CAT | CTG | CCT | CTG | ATC | CTG | GGT | CCC | GTG | CTG | 384 |
|---|---|---|---|---|---|---|---|---|---|---|---|---|---|---|---|---|
| Glu | Pro | Glu | Val | Asp | Ala | His | Leu | Pro | Leu | Ile | Leu | Gly | Pro | Val | Leu | |
| | | | 115 | | | | | 120 | | | | | 125 | | | |

| GCC | TTG | CTG | GTC | CTG | GTG | GCC | CTG | GGC | ACT | CTG | GGC | TTG | TGG | CGT | GTC | 432 |
|---|---|---|---|---|---|---|---|---|---|---|---|---|---|---|---|---|
| Ala | Leu | Leu | Val | Leu | Val | Ala | Leu | Gly | Thr | Leu | Gly | Leu | Trp | Arg | Val | |
| | | 130 | | | | | 135 | | | | | 140 | | | | |

| CGG | AGA | AGG | CAG | GAG | AAG | CAG | CGG | GGT | CTG | CAC | AGT | GAC | CTG | GGC | GAG | 480 |
|---|---|---|---|---|---|---|---|---|---|---|---|---|---|---|---|---|
| Arg | Arg | Arg | Gln | Glu | Lys | Gln | Arg | Gly | Leu | His | Ser | Asp | Leu | Gly | Glu | |

| | | | | | | | | | | | | | | | | |
|---|---|---|---|---|---|---|---|---|---|---|---|---|---|---|---|---|
| 145 | | | | | 150 | | | | | 155 | | | | | 160 | |
| TCC | AGT | CTC | ATC | CTG | AAG | GCA | TCG | GAA | CAG | GGA | GAC | AGC | ATG | TTG | GGG | 528 |
| Ser | Ser | Leu | Ile | Leu | Lys | Ala | Ser | Glu | Gln | Gly | Asp | Ser | Met | Leu | Gly | |
| | | | 165 | | | | | 170 | | | | | 175 | | | |
| GAC | TTC | CTG | GTC | AGC | GAC | TGT | ACC | ACA | GGC | AGC | GGC | TCA | GGG | CTA | CCC | 576 |
| Asp | Phe | Leu | Val | Ser | Asp | Cys | Thr | Thr | Gly | Ser | Gly | Ser | Gly | Leu | Pro | |
| | | | 180 | | | | | 185 | | | | | 190 | | | |
| TTC | TTG | GTG | CAG | AGG | ACA | GTA | GCG | CGA | CAG | GTT | GCA | CTG | GTG | GAG | TGT | 624 |
| Phe | Leu | Val | Gln | Arg | Thr | Val | Ala | Arg | Gln | Val | Ala | Leu | Val | Glu | Cys | |
| | | | 195 | | | | | 200 | | | | | 205 | | | |
| GTG | GGA | AAG | GGC | CGA | TAT | GGC | GAG | GTG | TGG | CGC | GGT | TCG | TGG | CAT | GGC | 672 |
| Val | Gly | Lys | Gly | Arg | Tyr | Gly | Glu | Val | Trp | Arg | Gly | Ser | Trp | His | Gly | |
| | | | 210 | | | | | 215 | | | | | 220 | | | |
| GAG | AGT | GTG | GCG | GTC | AAG | ATT | TTC | TCC | TCA | CGA | GAT | GAG | CAG | TCC | TGG | 720 |
| Glu | Ser | Val | Ala | Val | Lys | Ile | Phe | Ser | Ser | Arg | Asp | Glu | Gln | Ser | Trp | |
| 225 | | | | | 230 | | | | | 235 | | | | | 240 | |
| TTC | CGG | GAG | ACA | GAG | ATC | TAC | AAC | ACA | GTT | CTG | CTT | AGA | CAC | GAC | AAC | 768 |
| Phe | Arg | Glu | Thr | Glu | Ile | Tyr | Asn | Thr | Val | Leu | Leu | Arg | His | Asp | Asn | |
| | | | | 245 | | | | | 250 | | | | | 255 | | |
| ATC | CTA | GGC | TTC | ATC | GCC | TCC | GAC | ATG | ACC | TCG | CGG | AAC | TCC | AGC | ACG | 816 |
| Ile | Leu | Gly | Phe | Ile | Ala | Ser | Asp | Met | Thr | Ser | Arg | Asn | Ser | Ser | Thr | |
| | | | 260 | | | | | 265 | | | | | 270 | | | |
| CAG | CTG | TGG | CTT | ATC | ACC | CAC | TAC | CAC | GAG | CAT | GGC | TCC | CTC | TAT | GAC | 864 |
| Gln | Leu | Trp | Leu | Ile | Thr | His | Tyr | His | Glu | His | Gly | Ser | Leu | Tyr | Asp | |
| | | | 275 | | | | | 280 | | | | | 285 | | | |
| TTT | CTG | CAG | AGG | CAG | ACG | CTG | GAG | CCC | CAG | TTG | GCC | CTG | AGG | CTG | GCT | 912 |
| Phe | Leu | Gln | Arg | Gln | Thr | Leu | Glu | Pro | Gln | Leu | Ala | Leu | Arg | Leu | Ala | |
| | | | 290 | | | | | 295 | | | | | 300 | | | |
| GTG | TCC | GCG | GCC | TGC | GCT | GGC | CTG | GCG | CAC | CTG | CAT | GTA | GAG | ATC | TTT | 960 |
| Val | Ser | Ala | Ala | Cys | Ala | Gly | Leu | Ala | His | Leu | His | Val | Glu | Ile | Phe | |
| 305 | | | | | 310 | | | | | 315 | | | | | 320 | |
| GGC | ACT | CAA | GGC | AAA | CCA | GCC | ATC | GCC | CAT | CGT | GAC | CTC | AAG | AGC | CGC | 1008 |
| Gly | Thr | Gln | Gly | Lys | Pro | Ala | Ile | Ala | His | Arg | Asp | Leu | Lys | Ser | Arg | |
| | | | | 325 | | | | | 330 | | | | | 335 | | |
| AAC | GTG | CTG | GTC | AAG | AGC | AAC | TTG | CAG | TGT | TGC | ATT | GCA | GAC | CTG | GGA | 1056 |
| Asn | Val | Leu | Val | Lys | Ser | Asn | Leu | Gln | Cys | Cys | Ile | Ala | Asp | Leu | Gly | |
| | | | 340 | | | | | 345 | | | | | 350 | | | |
| TTG | GCT | GTG | ATG | CAC | TCG | CAA | AGC | AGC | GAT | TAC | CTG | GAC | ATT | GGT | AAC | 1104 |
| Leu | Ala | Val | Met | His | Ser | Gln | Ser | Ser | Asp | Tyr | Leu | Asp | Ile | Gly | Asn | |
| | | | 355 | | | | | 360 | | | | | 365 | | | |
| AAC | CCC | CGA | GTG | GGT | ACC | AAG | AGA | TAC | ATG | GCA | CCC | GAG | GTG | CTG | GAT | 1152 |
| Asn | Pro | Arg | Val | Gly | Thr | Lys | Arg | Tyr | Met | Ala | Pro | Glu | Val | Leu | Asp | |
| | | 370 | | | | | 375 | | | | | 380 | | | | |
| GAG | CAG | ATC | CGC | ACA | GAC | TGT | TTT | GAG | TCG | TAC | AAG | TGG | ACA | GAC | ATC | 1200 |
| Glu | Gln | Ile | Arg | Thr | Asp | Cys | Phe | Glu | Ser | Tyr | Lys | Trp | Thr | Asp | Ile | |
| 385 | | | | | 390 | | | | | 395 | | | | | 400 | |
| TGG | GCC | TTC | GGC | TTA | GTG | CTA | TGG | GAG | ATT | GCC | CGG | CGG | ACC | ATC | ATC | 1248 |
| Trp | Ala | Phe | Gly | Leu | Val | Leu | Trp | Glu | Ile | Ala | Arg | Arg | Thr | Ile | Ile | |
| | | | 405 | | | | | 410 | | | | | 415 | | | |
| AAT | GGC | ATT | GTG | GAG | GAC | TAC | AGG | CCA | CCC | TTC | TAT | GAC | ATG | GTA | CCC | 1296 |
| Asn | Gly | Ile | Val | Glu | Asp | Tyr | Arg | Pro | Pro | Phe | Tyr | Asp | Met | Val | Pro | |
| | | | 420 | | | | | 425 | | | | | 430 | | | |
| AAT | GAC | CCC | AGT | TTT | GAG | GAC | ATG | AAA | AAG | GTG | GTG | TGT | GTT | GAC | CAG | 1344 |
| Asn | Asp | Pro | Ser | Phe | Glu | Asp | Met | Lys | Lys | Val | Val | Cys | Val | Asp | Gln | |
| | | | 435 | | | | | 440 | | | | | 445 | | | |
| CAG | ACC | CCC | ACC | ATC | CCT | AAC | CGA | CTG | GCA | GCA | GAT | CCG | GTC | CTC | TCC | 1392 |
| Gln | Thr | Pro | Thr | Ile | Pro | Asn | Arg | Leu | Ala | Ala | Asp | Pro | Val | Leu | Ser | |
| | | | 450 | | | | | 455 | | | | | 460 | | | |
| GGG | CTG | GCC | CAG | ATG | ATG | CGA | GAG | TGC | TGG | TAC | CCC | AAC | CCC | TCC | GCT | 1440 |
| Gly | Leu | Ala | Gln | Met | Met | Arg | Glu | Cys | Trp | Tyr | Pro | Asn | Pro | Ser | Ala | |

```
465                          470                          475                          480
CGC  CTC  ACC  GCA  CTG  CGC  ATA  AAG  AAG  ACA  TTA  CAG  AAG  CTC  AGC  CAG      1488
Arg  Leu  Thr  Ala  Leu  Arg  Ile  Lys  Lys  Thr  Leu  Gln  Lys  Leu  Ser  Gln
               485                         490                         495

AAT  CCA  GAG  AAA  CCC  AAA  GTG  ATT  CAC  TAG                                    1518
Asn  Pro  Glu  Lys  Pro  Lys  Val  Ile  His
               500                    505
```

( 2 ) INFORMATION FOR SEQ ID NO: 4:

( i ) SEQUENCE CHARACTERISTICS:
        ( A ) LENGTH: 1506
        ( B ) TYPE: nucleic acid
        ( C ) STRANDEDNESS: double
        ( D ) TOPOLOGY: linear ( x i ) SEQUENCE DESCRIPTION: SEQ ID NO: 4:

```
ATG  GAG  GCG  GCG  TCG  GCT  GCT  TTG  CGT  CGC  TGC  CTG  CTT  CTC  ATC  GTG       48
Met  Glu  Ala  Ala  Ser  Ala  Ala  Leu  Arg  Arg  Cys  Leu  Leu  Leu  Ile  Val
1                        5                         10                        15

TTG  GTG  GCG  GCG  GCG  ACG  CTC  CCG  GGG  GCG  AAG  GCA  TTA  CAG  TGT            96
Leu  Val  Ala  Ala  Ala  Thr  Leu  Leu  Pro  Gly  Ala  Lys  Ala  Leu  Gln  Cys
                    20                       25                        30

TTC  TGC  CAC  CTC  TGT  ACA  AAG  GAC  AAT  TTT  ACT  TGT  GAG  ACA  GAT  GGT      144
Phe  Cys  His  Leu  Cys  Thr  Lys  Asp  Asn  Phe  Thr  Cys  Glu  Thr  Asp  Gly
               35                        40                        45

CTC  TGC  TTT  GTC  TCA  GTC  ACC  GAG  ACC  ACA  GAC  AAA  GTT  ATA  CAC  AAT      192
Leu  Cys  Phe  Val  Ser  Val  Thr  Glu  Thr  Thr  Asp  Lys  Val  Ile  His  Asn
          50                        55                        60

AGC  ATG  TGT  ATA  GCT  GAA  ATC  GAC  CTA  ATT  CCC  CGA  GAC  AGG  CCA  TTT      240
Ser  Met  Cys  Ile  Ala  Glu  Ile  Asp  Leu  Ile  Pro  Arg  Asp  Arg  Pro  Phe
65                       70                        75                        80

GTT  TGT  GCA  CCA  TCT  TCA  AAA  ACA  GGG  GCA  GTT  ACG  TAT  TGC  TGC  AAT      288
Val  Cys  Ala  Pro  Ser  Ser  Lys  Thr  Gly  Ala  Val  Thr  Tyr  Cys  Cys  Asn
                    85                        90                        95

CAG  GAT  CAC  TGC  AAT  AAA  ATA  GAA  CTC  CCA  ACT  ACA  GGA  CCT  TTT  TCA      336
Gln  Asp  His  Cys  Asn  Lys  Ile  Glu  Leu  Pro  Thr  Thr  Gly  Pro  Phe  Ser
               100                       105                       110

GAA  AAG  CAG  TCA  GCT  GGC  CTC  GGT  CCT  GTG  GAG  CTG  GCA  GCT  GTC  ATT      384
Glu  Lys  Gln  Ser  Ala  Gly  Leu  Gly  Pro  Val  Glu  Leu  Ala  Ala  Val  Ile
          115                       120                       125

GCT  GGT  CCA  GTC  TGC  TTC  GTC  TGC  ATT  GCA  CTT  ATG  CTG  ATG  GTC  TAT      432
Ala  Gly  Pro  Val  Cys  Phe  Val  Cys  Ile  Ala  Leu  Met  Leu  Met  Val  Tyr
     130                       135                       140

ATC  TGC  CAT  AAC  CGC  ACT  GTC  ATT  CAC  CAC  CGC  GTG  CCA  AAT  GAA  GAG      480
Ile  Cys  His  Asn  Arg  Thr  Val  Ile  His  His  Arg  Val  Pro  Asn  Glu  Glu
145                      150                       155                      160

GAT  CCC  TCA  CTA  GAT  CGC  CCT  TTC  ATT  TCA  GAG  GGC  ACC  ACC  TTA  AAA      528
Asp  Pro  Ser  Leu  Asp  Arg  Pro  Phe  Ile  Ser  Glu  Gly  Thr  Thr  Leu  Lys
                    165                       170                       175

GAT  TTA  ATT  TAT  GAT  ATG  ACA  ACA  TCA  GGG  TCT  GGA  TCA  GGT  TTA  CCA      576
Asp  Leu  Ile  Tyr  Asp  Met  Thr  Thr  Ser  Gly  Ser  Gly  Ser  Gly  Leu  Pro
               180                       185                       190

CTG  CTT  GTT  CAA  AGA  ACA  ATT  GCA  AGG  ACC  ATT  GTG  CTA  CAA  GAA  AGC      624
Leu  Leu  Val  Gln  Arg  Thr  Ile  Ala  Arg  Thr  Ile  Val  Leu  Gln  Glu  Ser
          195                       200                       205

ATC  GGC  AAA  GGT  CGG  TTT  GGA  GAA  GTT  TGG  CGA  GGC  AAA  TGG  CGG  GGA      672
Ile  Gly  Lys  Gly  Arg  Phe  Gly  Glu  Val  Trp  Arg  Gly  Lys  Trp  Arg  Gly
     210                       215                       220

GAA  GAA  GTT  GCC  GTG  AAG  ATA  TTC  TCT  TCT  AGA  GAA  GAA  CGT  TCA  TGG      720
Glu  Glu  Val  Ala  Val  Lys  Ile  Phe  Ser  Ser  Arg  Glu  Glu  Arg  Ser  Trp
225                      230                       235                      240
```

| | | | | | | | | | | | | | | | | |
|---|---|---|---|---|---|---|---|---|---|---|---|---|---|---|---|---|
| TTC | CGA | GAG | GCA | GAG | ATT | TAT | CAG | ACT | GTA | ATG | TTA | CGC | CAT | GAA | AAT | 768 |
| Phe | Arg | Glu | Ala | Glu | Ile | Tyr | Gln | Thr | Val | Met | Leu | Arg | His | Glu | Asn | |
| | | | | 245 | | | | | 250 | | | | | 255 | | |
| ATC | CTG | GGG | TTT | ATA | GCA | GCA | GAC | AAC | AAA | GAC | AAT | GGT | ACA | TGG | ACT | 816 |
| Ile | Leu | Gly | Phe | Ile | Ala | Ala | Asp | Asn | Lys | Asp | Asn | Gly | Thr | Trp | Thr | |
| | | | 260 | | | | | 265 | | | | | 270 | | | |
| CAG | CTG | TGG | TTG | GTG | TCG | GAT | TAT | CAT | GAG | CAT | GGA | TCC | CTT | TTC | GAT | 864 |
| Gln | Leu | Trp | Leu | Val | Ser | Asp | Tyr | His | Glu | His | Gly | Ser | Leu | Phe | Asp | |
| | | 275 | | | | | 280 | | | | | 285 | | | | |
| TAC | TTG | AAT | AGA | TAC | ACT | GTT | ACT | GTG | GAA | GGA | ATG | ATC | AAA | CTC | GCT | 912 |
| Tyr | Leu | Asn | Arg | Tyr | Thr | Val | Thr | Val | Glu | Gly | Met | Ile | Lys | Leu | Ala | |
| | 290 | | | | | 295 | | | | | 300 | | | | | |
| CTG | TCC | ACG | GCA | AGT | GGT | CTT | GCC | CAT | CTT | CAC | ATG | GAG | ATT | GTT | GGT | 960 |
| Leu | Ser | Thr | Ala | Ser | Gly | Leu | Ala | His | Leu | His | Met | Glu | Ile | Val | Gly | |
| 305 | | | | | 310 | | | | | 315 | | | | | 320 | |
| ACC | CAA | GGA | AAA | CCA | GCT | ATT | GCC | CAT | AGA | GAT | TTG | AAA | TCA | AAG | AAT | 1008 |
| Thr | Gln | Gly | Lys | Pro | Ala | Ile | Ala | His | Arg | Asp | Leu | Lys | Ser | Lys | Asn | |
| | | | | 325 | | | | | 330 | | | | | 335 | | |
| ATC | TTG | GTG | AAG | AAA | AAT | GGA | ACC | TGT | TGT | ATT | GCA | GAT | TTG | GGA | CTT | 1056 |
| Ile | Leu | Val | Lys | Lys | Asn | Gly | Thr | Cys | Cys | Ile | Ala | Asp | Leu | Gly | Leu | |
| | | | 340 | | | | | 345 | | | | | 350 | | | |
| GCT | GTG | AGA | CAT | GAT | TCT | GCC | ACA | GAT | ACA | ATT | GAT | ATT | GCT | CCA | AAC | 1104 |
| Ala | Val | Arg | His | Asp | Ser | Ala | Thr | Asp | Thr | Ile | Asp | Ile | Ala | Pro | Asn | |
| | | 355 | | | | | 360 | | | | | 365 | | | | |
| CAC | AGA | GTA | GGC | ACT | AAA | AGG | TAT | ATG | GCC | CCT | GAA | GTT | CTA | GAT | GAT | 1152 |
| His | Arg | Val | Gly | Thr | Lys | Arg | Tyr | Met | Ala | Pro | Glu | Val | Leu | Asp | Asp | |
| | 370 | | | | | 375 | | | | | 380 | | | | | |
| TCC | ATA | AAT | ATG | AAA | CAT | TTT | GAA | TCC | TTC | AAA | CGT | GCT | GAC | ATC | TAT | 1200 |
| Ser | Ile | Asn | Met | Lys | His | Phe | Glu | Ser | Phe | Lys | Arg | Ala | Asp | Ile | Tyr | |
| 385 | | | | | 390 | | | | | 395 | | | | | 400 | |
| GCA | ATG | GGC | TTA | GTA | TTC | TGG | GAA | ATC | GCT | CGA | CGC | TGT | TCC | ATT | GGC | 1248 |
| Ala | Met | Gly | Leu | Val | Phe | Trp | Glu | Ile | Ala | Arg | Arg | Cys | Ser | Ile | Gly | |
| | | | | 405 | | | | | 410 | | | | | 415 | | |
| GGA | ATC | CAC | GAA | GAC | TAC | CAG | TTG | CCT | TAC | TAT | GAT | CTT | GTA | CCT | TCT | 1296 |
| Gly | Ile | His | Glu | Asp | Tyr | Gln | Leu | Pro | Tyr | Tyr | Asp | Leu | Val | Pro | Ser | |
| | | | 420 | | | | | 425 | | | | | 430 | | | |
| GAT | CCA | TCC | GTT | GAA | GAA | ATG | AGA | AAA | GTA | GTT | TGT | GAA | CAG | AAG | TTA | 1344 |
| Asp | Pro | Ser | Val | Glu | Glu | Met | Arg | Lys | Val | Val | Cys | Glu | Gln | Lys | Leu | |
| | | 435 | | | | | 440 | | | | | 445 | | | | |
| AGG | CCA | AAT | ATT | CCC | AAC | AGA | TGG | CAG | AGC | TGT | GAG | GCC | TTG | AGA | GTG | 1392 |
| Arg | Pro | Asn | Ile | Pro | Asn | Arg | Trp | Gln | Ser | Cys | Glu | Ala | Leu | Arg | Val | |
| | | 450 | | | | | 455 | | | | | 460 | | | | |
| ATG | GCC | AAA | ATT | ATG | AGA | GAA | TGT | TGG | TAT | GCC | AAT | GGA | GCA | GCT | AGG | 1440 |
| Met | Ala | Lys | Ile | Met | Arg | Glu | Cys | Trp | Tyr | Ala | Asn | Gly | Ala | Ala | Arg | |
| 465 | | | | | 470 | | | | | 475 | | | | | 480 | |
| CTG | ACA | GCT | TTG | CGA | ATT | AAA | AAA | ACA | TTG | TCA | CAG | CTC | AGC | CAA | CAG | 1488 |
| Leu | Thr | Ala | Leu | Arg | Ile | Lys | Lys | Thr | Leu | Ser | Gln | Leu | Ser | Gln | Gln | |
| | | | | 485 | | | | | 490 | | | | | 495 | | |
| GAA | GGC | ATC | AAA | ATG | TAA | | | | | | | | | | | 1506 |
| Glu | Gly | Ile | Lys | Met | | | | | | | | | | | | |
| | | | | 500 | | | | | | | | | | | | |

( 2 ) INFORMATION FOR SEQ ID NO: 5:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO: 5:

GTCTACCAGA AGGGCTGCTT                    20

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CCGGAGCCTC CTCCTTCTTC                    20

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TCCCTACTGG GTTTGAGACA                    20

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 8:

GCTGCGGGAG CCTGAACCAG                    20

( 2 ) INFORMATION FOR SEQ ID NO: 9:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 9:

AAATCCAATG TTTGAATACT                    20

( 2 ) INFORMATION FOR SEQ ID NO: 10:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GTGGCCGTSA ARATYTT                       17

( 2 ) INFORMATION FOR SEQ ID NO: 11:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GACYTCTGGR GCCATRTA                      18

( 2 ) INFORMATION FOR SEQ ID NO: 12:

( i ) SEQUENCE CHARACTERISTICS:
        ( A ) LENGTH: 21
        ( B ) TYPE: amino acid
        ( C ) STRANDEDNESS:
        ( D ) TOPOLOGY: linear ( x i ) SEQUENCE DESCRIPTION: SEQ ID NO: 12:

```
Gly  Lys  Gly  Arg  Tyr  Gly  Glu  Val  Xaa  Xaa  Xaa  Xaa  Xaa  Xaa  Xaa  Xaa
 1                   5                        10                            15

Xaa  Xaa  Xaa  Xaa  Lys
               20
```

( 2 ) INFORMATION FOR SEQ ID NO: 13:

( i ) SEQUENCE CHARACTERISTICS:
        ( A ) LENGTH: 21
        ( B ) TYPE: amino acid
        ( C ) STRANDEDNESS:
        ( D ) TOPOLOGY: linear ( x i ) SEQUENCE DESCRIPTION: SEQ ID NO: 13:

```
Gly  Lys  Gly  Arg  Phe  Gly  Glu  Val  Xaa  Xaa  Xaa  Xaa  Xaa  Xaa  Xaa  Xaa
 1                   5                        10                            15

Xaa  Xaa  Xaa  Xaa  Lys
               20
```

( 2 ) INFORMATION FOR SEQ ID NO: 14:

( i ) SEQUENCE CHARACTERISTICS:
        ( A ) LENGTH: 509
        ( B ) TYPE: amino acid
        ( C ) STRANDEDNESS:
        ( D ) TOPOLOGY: linear ( x i ) SEQUENCE DESCRIPTION: SEQ ID NO: 14:

```
Met  Val  Asp  Gly  Ala  Met  Ile  Leu  Ser  Val  Leu  Met  Met  Met  Ala  Leu
 1                   5                        10                            15

Pro  Ser  Pro  Ser  Met  Glu  Asp  Glu  Glu  Pro  Lys  Val  Asn  Pro  Lys  Leu
               20                       25                        30

Tyr  Met  Cys  Val  Cys  Glu  Gly  Leu  Ser  Cys  Gly  Asn  Glu  Asp  His  Cys
          35                        40                        45

Glu  Gly  Gln  Gln  Cys  Phe  Ser  Ser  Leu  Ser  Val  Asn  Asp  Gly  Phe  Arg
     50                        55                        60

Val  Tyr  Gln  Lys  Gly  Cys  Phe  Gln  Val  Tyr  Glu  Gln  Gly  Lys  Met  Thr
65                        70                        75                        80

Cys  Lys  Thr  Pro  Pro  Ser  Pro  Gly  Gln  Ala  Val  Glu  Cys  Cys  Gln  Gly
                    85                        90                        95

Asp  Trp  Cys  Asn  Arg  Asn  Val  Thr  Ala  Arg  Leu  Pro  Thr  Lys  Gly  Lys
               100                      105                      110

Ser  Phe  Pro  Gly  Ser  Gln  Asn  Phe  His  Leu  Glu  Val  Gly  Leu  Ile  Ile
          115                      120                      125

Leu  Ser  Val  Val  Phe  Ala  Val  Cys  Leu  Phe  Ala  Cys  Ile  Leu  Gly  Val
     130                      135                      140

Ala  Leu  Arg  Lys  Phe  Lys  Arg  Arg  Asn  Gln  Glu  Arg  Leu  Asn  Pro  Arg
145                      150                      155                      160

Asp  Val  Glu  Tyr  Gly  Thr  Ile  Glu  Gly  Leu  Ile  Thr  Thr  Asn  Val  Gly
                    165                      170                      175

Asp  Ser  Thr  Leu  Ala  Glu  Leu  Leu  Asp  His  Ser  Cys  Thr  Ser  Gly  Ser
               180                      185                      190
```

| | | | | | | | | | | | | | | |
|---|---|---|---|---|---|---|---|---|---|---|---|---|---|---|
| Gly | Ser | Gly | Leu | Pro | Phe | Leu | Val | Gln | Arg | Thr | Val | Ala | Arg | Gln | Ile |
| | | 195 | | | | | 200 | | | | | 205 | | | |
| Thr | Leu | Leu | Glu | Cys | Val | Gly | Lys | Gly | Arg | Tyr | Gly | Glu | Val | Trp | Arg |
| | | 210 | | | | | 215 | | | | | 220 | | | |
| Gly | Ser | Trp | Gln | Gly | Glu | Asn | Val | Ala | Val | Lys | Ile | Phe | Ser | Ser | Arg |
| 225 | | | | | 230 | | | | | 235 | | | | | 240 |
| Asp | Glu | Lys | Ser | Trp | Phe | Arg | Glu | Thr | Glu | Leu | Tyr | Asn | Thr | Val | Met |
| | | | | 245 | | | | | 250 | | | | | 255 | |
| Leu | Arg | His | Glu | Asn | Ile | Leu | Gly | Phe | Ile | Ala | Ser | Asp | Met | Thr | Ser |
| | | | 260 | | | | | 265 | | | | | 270 | | |
| Arg | His | Ser | Ser | Thr | Gln | Leu | Trp | Leu | Ile | Thr | His | Tyr | His | Glu | Met |
| | | 275 | | | | | 280 | | | | | 285 | | | |
| Gly | Ser | Leu | Tyr | Asp | Tyr | Leu | Gln | Leu | Thr | Thr | Leu | Asp | Thr | Val | Ser |
| | | 290 | | | | | 295 | | | | | 300 | | | |
| Cys | Leu | Arg | Ile | Val | Leu | Ser | Ile | Ala | Ser | Gly | Leu | Ala | His | Leu | His |
| 305 | | | | | 310 | | | | | 315 | | | | | 320 |
| Ile | Glu | Ile | Phe | Gly | Thr | Gln | Gly | Lys | Ser | Ala | Ile | Ala | His | Arg | Asp |
| | | | | 325 | | | | | 330 | | | | | 335 | |
| Leu | Lys | Ser | Lys | Asn | Ile | Leu | Val | Lys | Lys | Asn | Gly | Gln | Cys | Cys | Ile |
| | | | 340 | | | | | 345 | | | | | 350 | | |
| Ala | Asp | Leu | Gly | Leu | Ala | Val | Met | His | Ser | Gln | Ser | Thr | Asn | Gln | Leu |
| | | 355 | | | | | 360 | | | | | 365 | | | |
| Asp | Val | Gly | Asn | Asn | Pro | Arg | Val | Gly | Thr | Lys | Arg | Tyr | Met | Ala | Pro |
| | 370 | | | | | 375 | | | | | 380 | | | | |
| Glu | Val | Leu | Asp | Glu | Thr | Ile | Gln | Val | Asp | Cys | Phe | Asp | Ser | Tyr | Lys |
| 385 | | | | | 390 | | | | | 395 | | | | | 400 |
| Arg | Val | Asp | Ile | Trp | Ala | Phe | Gly | Leu | Val | Leu | Trp | Glu | Val | Ala | Arg |
| | | | | 405 | | | | | 410 | | | | | 415 | |
| Arg | Met | Val | Ser | Asn | Gly | Ile | Val | Glu | Asp | Tyr | Lys | Pro | Pro | Phe | Tyr |
| | | | 420 | | | | | 425 | | | | | 430 | | |
| Asp | Val | Val | Pro | Asn | Asp | Pro | Ser | Phe | Glu | Asp | Met | Arg | Lys | Val | Val |
| | | 435 | | | | | 440 | | | | | 445 | | | |
| Cys | Val | Asp | Gln | Gln | Arg | Pro | Asn | Ile | Pro | Asn | Arg | Trp | Phe | Ser | Asp |
| | 450 | | | | | 455 | | | | | 460 | | | | |
| Pro | Thr | Leu | Thr | Ser | Leu | Ala | Asn | Val | Met | Lys | Glu | Cys | Trp | Tyr | Gln |
| 465 | | | | | 470 | | | | | 475 | | | | | 480 |
| Asn | Pro | Ser | Ala | Arg | Leu | Thr | Ala | Leu | Arg | Ile | Lys | Lys | Thr | Leu | Thr |
| | | | | 485 | | | | | 490 | | | | | 495 | |
| Lys | Ile | Asp | Asn | Ser | Leu | Asp | Lys | Leu | Lys | Thr | Asp | Cys | | | |
| | | | 500 | | | | | 505 | | | | | | | |

( 2 ) INFORMATION FOR SEQ ID NO: 15:

( i ) SEQUENCE CHARACTERISTICS:
        ( A ) LENGTH: 501
        ( B ) TYPE: amino acid
        ( C ) STRANDEDNESS:
        ( D ) TOPOLOGY: linear ( x i ) SEQUENCE DESCRIPTION: SEQ ID NO: 15:

| | | | | | | | | | | | | | | |
|---|---|---|---|---|---|---|---|---|---|---|---|---|---|---|
| Met | Ala | Glu | Ser | Ala | Gly | Ala | Ser | Ser | Phe | Phe | Pro | Leu | Val | Val | Leu |
| 1 | | | | 5 | | | | | 10 | | | | | 15 | |
| Leu | Leu | Ala | Gly | Ser | Gly | Gly | Ser | Gly | Pro | Arg | Gly | Ile | Gln | Ala | Leu |
| | | | 20 | | | | | 25 | | | | | 30 | | |
| Leu | Cys | Ala | Cys | Thr | Ser | Cys | Leu | Gln | Thr | Asn | Tyr | Thr | Cys | Glu | Thr |
| | | 35 | | | | | 40 | | | | | 45 | | | |

| | | | | | | | | | | | | | | |
|---|---|---|---|---|---|---|---|---|---|---|---|---|---|---|
| Asp | Gly | Ala | Cys | Met | Val | Ser | Ile | Phe | Asn | Leu | Asp | Gly | Met | Glu | His |
| | 50 | | | | 55 | | | | | 60 | | | | |
| His | Val | Arg | Thr | Cys | Ile | Pro | Lys | Val | Glu | Leu | Val | Pro | Ala | Gly | Lys |
| 65 | | | | | 70 | | | | 75 | | | | | 80 |
| Pro | Phe | Tyr | Cys | Leu | Ser | Ser | Glu | Asp | Leu | Arg | Asn | Thr | His | Cys | Cys |
| | | | | 85 | | | | | 90 | | | | | 95 |
| Tyr | Ile | Asp | Phe | Cys | Asn | Lys | Ile | Asp | Leu | Arg | Val | Pro | Ser | Gly | His |
| | | | 100 | | | | | 105 | | | | | 110 | |
| Leu | Lys | Glu | Pro | Glu | His | Pro | Ser | Met | Trp | Gly | Pro | Val | Glu | Leu | Val |
| | | 115 | | | | | 120 | | | | | 125 | | |
| Gly | Ile | Ile | Ala | Gly | Pro | Val | Phe | Leu | Leu | Phe | Leu | Ile | Ile | Ile | Ile |
| | 130 | | | | | 135 | | | | | 140 | | | | |
| Val | Phe | Leu | Val | Ile | Asn | Tyr | His | Gln | Arg | Val | Tyr | His | Asn | Arg | Gln |
| 145 | | | | | 150 | | | | | 155 | | | | | 160 |
| Arg | Leu | Asp | Met | Glu | Asp | Pro | Ser | Cys | Glu | Met | Cys | Leu | Ser | Lys | Asp |
| | | | | 165 | | | | | 170 | | | | | 175 | |
| Lys | Thr | Leu | Gln | Asp | Leu | Val | Tyr | Asp | Leu | Ser | Thr | Ser | Gly | Ser | Gly |
| | | | 180 | | | | | 185 | | | | | 190 | | |
| Ser | Gly | Leu | Pro | Leu | Phe | Val | Gln | Arg | Thr | Val | Ala | Arg | Thr | Ile | Val |
| | | 195 | | | | | 200 | | | | | 205 | | | |
| Leu | Gln | Glu | Ile | Ile | Gly | Lys | Gly | Arg | Phe | Gly | Glu | Val | Trp | Arg | Gly |
| | 210 | | | | | 215 | | | | | 220 | | | | |
| Arg | Trp | Arg | Gly | Gly | Asp | Val | Ala | Val | Lys | Ile | Phe | Ser | Ser | Arg | Glu |
| 225 | | | | | 230 | | | | | 235 | | | | | 240 |
| Glu | Arg | Ser | Trp | Phe | Arg | Glu | Ala | Glu | Ile | Tyr | Gln | Thr | Val | Met | Leu |
| | | | | 245 | | | | | 250 | | | | | 255 | |
| Arg | His | Glu | Asn | Ile | Leu | Gly | Phe | Ile | Ala | Ala | Asp | Asn | Lys | Asp | Asn |
| | | | | 260 | | | | | 265 | | | | | 270 | |
| Gly | Thr | Trp | Thr | Gln | Leu | Trp | Leu | Val | Ser | Asp | Tyr | His | Glu | His | Gly |
| | | | 275 | | | | | 280 | | | | | 285 | | |
| Ser | Leu | Phe | Asp | Tyr | Leu | Asn | Arg | Tyr | Thr | Val | Thr | Ile | Glu | Gly | Met |
| | | 290 | | | | | 295 | | | | | 300 | | | |
| Ile | Lys | Leu | Ala | Leu | Ser | Ala | Ala | Ser | Gly | Leu | Ala | His | Leu | His | Met |
| 305 | | | | | 310 | | | | | 315 | | | | | 320 |
| Glu | Ile | Val | Gly | Thr | Gln | Gly | Lys | Pro | Gly | Ile | Ala | His | Arg | Asp | Leu |
| | | | | 325 | | | | | 330 | | | | | 335 | |
| Lys | Ser | Lys | Asn | Ile | Leu | Val | Lys | Lys | Asn | Gly | Met | Cys | Ala | Ile | Ala |
| | | | 340 | | | | | 345 | | | | | 350 | | |
| Asp | Leu | Gly | Leu | Ala | Val | Arg | His | Asp | Ala | Val | Thr | Asp | Thr | Ile | Asp |
| | | 355 | | | | | 360 | | | | | 365 | | | |
| Ile | Ala | Pro | Asn | Gln | Arg | Val | Gly | Thr | Lys | Arg | Tyr | Met | Ala | Pro | Glu |
| | 370 | | | | | 375 | | | | | 380 | | | | |
| Val | Leu | Asp | Glu | Thr | Ile | Asn | Met | Lys | His | Phe | Asp | Ser | Phe | Lys | Cys |
| 385 | | | | | 390 | | | | | 395 | | | | | 400 |
| Ala | Asp | Ile | Tyr | Ala | Leu | Gly | Leu | Val | Tyr | Trp | Glu | Ile | Ala | Arg | Arg |
| | | | | 405 | | | | | 410 | | | | | 415 | |
| Cys | Asn | Ser | Gly | Gly | Val | His | Glu | Glu | Tyr | Gln | Leu | Pro | Tyr | Tyr | Asp |
| | | | 420 | | | | | 425 | | | | | 430 | | |
| Leu | Val | Pro | Ser | Asp | Pro | Ser | Ile | Glu | Glu | Met | Arg | Lys | Val | Val | Cys |
| | | 435 | | | | | 440 | | | | | 445 | | | |
| Asp | Gln | Lys | Leu | Arg | Pro | Asn | Val | Pro | Asn | Trp | Trp | Gln | Ser | Tyr | Glu |
| | 450 | | | | | 455 | | | | | 460 | | | | |
| Ala | Leu | Arg | Val | Met | Gly | Lys | Met | Met | Arg | Glu | Cys | Trp | Tyr | Ala | Asn |

```
465                         470                         475                         480
Gly Ala Ala Arg Leu Thr Ala Leu Arg Ile Lys Lys Thr Leu Ser Gln
                485                         490                         495
Glu Asp Val Lys Ile
            500
```

( 2 ) INFORMATION FOR SEQ ID NO: 16:

( i ) SEQUENCE CHARACTERISTICS:
        ( A ) LENGTH: 505
        ( B ) TYPE: amino acid
        ( C ) STRANDEDNESS:
        ( D ) TOPOLOGY: linear ( x i ) SEQUENCE DESCRIPTION: SEQ ID NO: 16:

```
Met Thr Leu Gly Ile Phe Arg Arg Val Phe Leu Met Leu Ser Val Ala
1               5                   10                  15
Leu Gly Leu Thr Lys Gly Asp Leu Val Lys Pro Ser Arg Gly Gln Leu
                20                  25                  30
Val Asn Cys Thr Cys Glu Asn Pro His Cys Lys Arg Pro Ile Cys Gln
            35                  40                  45
Gly Ala Trp Cys Thr Val Val Leu Val Arg Glu Gln Gly Arg His Pro
        50                  55                  60
Gln Val Tyr Arg Gly Cys Gly Ser Leu Asn Gln Glu Leu Cys Leu Gly
65                  70                  75                  80
Arg Pro Thr Glu Phe Val Asn His His Cys Cys Tyr Arg Ser Phe Cys
                85                  90                  95
Asn His Asn Val Ser Leu Met Leu Glu Ala Thr Gln Thr Pro Ser Glu
            100                 105                 110
Glu Pro Glu Val Asp Ala His Leu Pro Leu Ile Leu Gly Pro Val Leu
        115                 120                 125
Ala Leu Leu Val Leu Val Ala Leu Gly Thr Leu Gly Leu Trp Arg Val
        130                 135                 140
Arg Arg Arg Gln Glu Lys Gln Arg Gly Leu His Ser Asp Leu Gly Glu
145                 150                 155                 160
Ser Ser Leu Ile Leu Lys Ala Ser Glu Gln Gly Asp Ser Met Leu Gly
                165                 170                 175
Asp Phe Leu Val Ser Asp Cys Thr Thr Gly Ser Gly Ser Gly Leu Pro
            180                 185                 190
Phe Leu Val Gln Arg Thr Val Ala Arg Gln Val Ala Leu Val Glu Cys
        195                 200                 205
Val Gly Lys Gly Arg Tyr Gly Glu Val Trp Arg Gly Ser Trp His Gly
    210                 215                 220
Glu Ser Val Ala Val Lys Ile Phe Ser Ser Arg Asp Glu Gln Ser Trp
225                 230                 235                 240
Phe Arg Glu Thr Glu Ile Tyr Asn Thr Val Leu Leu Arg His Asp Asn
                245                 250                 255
Ile Leu Gly Phe Ile Ala Ser Asp Met Thr Ser Arg Asn Ser Ser Thr
            260                 265                 270
Gln Leu Trp Leu Ile Thr His Tyr His Glu His Gly Ser Leu Tyr Asp
        275                 280                 285
Phe Leu Gln Arg Gln Thr Leu Glu Pro Gln Leu Ala Leu Arg Leu Ala
        290                 295                 300
Val Ser Ala Ala Cys Ala Gly Leu Ala His Leu His Val Glu Ile Phe
305                 310                 315                 320
Gly Thr Gln Gly Lys Pro Ala Ile Ala His Arg Asp Leu Lys Ser Arg
```

|     |     |     |     | 325 |     |     |     | 330 |     |     |     | 335 |     |     |
| --- | --- | --- | --- | --- | --- | --- | --- | --- | --- | --- | --- | --- | --- | --- |
| Asn | Val | Leu | Val | Lys | Ser | Asn | Leu | Gln | Cys | Cys | Ile | Ala | Asp | Leu | Gly |
|     |     |     | 340 |     |     |     | 345 |     |     |     | 350 |     |     |     |

```
Leu  Ala  Val  Met  His  Ser  Gln  Ser  Ser  Asp  Tyr  Leu  Asp  Ile  Gly  Asn
               355                 360                 365

Asn  Pro  Arg  Val  Gly  Thr  Lys  Arg  Tyr  Met  Ala  Pro  Glu  Val  Leu  Asp
     370                 375                      380

Glu  Gln  Ile  Arg  Thr  Asp  Cys  Phe  Glu  Ser  Tyr  Lys  Trp  Thr  Asp  Ile
385                      390                      395                      400

Trp  Ala  Phe  Gly  Leu  Val  Leu  Trp  Glu  Ile  Ala  Arg  Arg  Thr  Ile  Ile
                    405                 410                      415

Asn  Gly  Ile  Val  Glu  Asp  Tyr  Arg  Pro  Pro  Phe  Tyr  Asp  Met  Val  Pro
                    420                 425                      430

Asn  Asp  Pro  Ser  Phe  Glu  Asp  Met  Lys  Lys  Val  Val  Cys  Val  Asp  Gln
               435                 440                      445

Gln  Thr  Pro  Thr  Ile  Pro  Asn  Arg  Leu  Ala  Ala  Asp  Pro  Val  Leu  Ser
          450                 455                 460

Gly  Leu  Ala  Gln  Met  Met  Arg  Glu  Cys  Trp  Tyr  Pro  Asn  Pro  Ser  Ala
465                      470                 475                      480

Arg  Leu  Thr  Ala  Leu  Arg  Ile  Lys  Lys  Thr  Leu  Gln  Lys  Leu  Ser  Gln
                    485                 490                      495

Asn  Pro  Glu  Lys  Pro  Lys  Val  Ile  His
               500                 505
```

(2) INFORMATION FOR SEQ ID NO: 17:

(i) SEQUENCE CHARACTERISTICS:
        (A) LENGTH: 501
        (B) TYPE: amino acid
        (C) STRANDEDNESS:
        (D) TOPOLOGY: linear (xi) SEQUENCE DESCRIPTION: SEQ ID NO: 17:

```
Met  Glu  Ala  Ala  Ser  Ala  Ala  Leu  Arg  Arg  Cys  Leu  Leu  Leu  Ile  Val
1                   5                   10                       15

Leu  Val  Ala  Ala  Ala  Thr  Leu  Leu  Pro  Gly  Ala  Lys  Ala  Leu  Gln  Cys
               20                  25                       30

Phe  Cys  His  Leu  Cys  Thr  Lys  Asp  Asn  Phe  Thr  Cys  Glu  Thr  Asp  Gly
          35                  40                       45

Leu  Cys  Phe  Val  Ser  Val  Thr  Glu  Thr  Thr  Asp  Lys  Val  Ile  His  Asn
     50                  55                       60

Ser  Met  Cys  Ile  Ala  Glu  Ile  Asp  Leu  Ile  Pro  Arg  Asp  Arg  Pro  Phe
65                   70                       75                            80

Val  Cys  Ala  Pro  Ser  Ser  Lys  Thr  Gly  Ala  Val  Thr  Tyr  Cys  Cys  Asn
               85                  90                       95

Gln  Asp  His  Cys  Asn  Lys  Ile  Glu  Leu  Pro  Thr  Thr  Gly  Pro  Phe  Ser
               100                 105                      110

Glu  Lys  Gln  Ser  Ala  Gly  Leu  Gly  Pro  Val  Glu  Leu  Ala  Ala  Val  Ile
          115                 120                      125

Ala  Gly  Pro  Val  Cys  Phe  Val  Cys  Ile  Ala  Leu  Met  Leu  Met  Val  Tyr
     130                 135                      140

Ile  Cys  His  Asn  Arg  Thr  Val  Ile  His  His  Arg  Val  Pro  Asn  Glu  Glu
145                 150                      155                           160

Asp  Pro  Ser  Leu  Asp  Arg  Pro  Phe  Ile  Ser  Glu  Gly  Thr  Thr  Leu  Lys
               165                 170                      175

Asp  Leu  Ile  Tyr  Asp  Met  Thr  Thr  Ser  Gly  Ser  Gly  Ser  Gly  Leu  Pro
```

|     |     |     |     |     | 180 |     |     |     | 185 |     |     |     | 190 |     |     |
| --- | --- | --- | --- | --- | --- | --- | --- | --- | --- | --- | --- | --- | --- | --- | --- |
| Leu | Leu | Val<br>195 | Gln | Arg | Thr | Ile | Ala<br>200 | Arg | Thr | Ile | Val | Leu<br>205 | Gln | Glu | Ser |
| Ile | Gly<br>210 | Lys | Gly | Arg | Phe | Gly<br>215 | Glu | Val | Trp | Arg | Gly<br>220 | Lys | Trp | Arg | Gly |
| Glu<br>225 | Glu | Val | Ala | Val | Lys<br>230 | Ile | Phe | Ser | Ser | Arg<br>235 | Glu | Glu | Arg | Ser | Trp<br>240 |
| Phe | Arg | Glu | Ala | Glu<br>245 | Ile | Tyr | Gln | Thr | Val<br>250 | Met | Leu | Arg | His | Glu<br>255 | Asn |
| Ile | Leu | Gly | Phe<br>260 | Ile | Ala | Ala | Asp | Asn<br>265 | Lys | Asp | Asn | Gly | Thr<br>270 | Trp | Thr |
| Gln | Leu | Trp<br>275 | Leu | Val | Ser | Asp | Tyr<br>280 | His | Glu | His | Gly | Ser<br>285 | Leu | Phe | Asp |
| Tyr | Leu<br>290 | Asn | Arg | Tyr | Thr | Val<br>295 | Thr | Val | Glu | Gly | Met<br>300 | Ile | Lys | Leu | Ala |
| Leu<br>305 | Ser | Thr | Ala | Ser | Gly<br>310 | Leu | Ala | His | Leu | His<br>315 | Met | Glu | Ile | Val | Gly<br>320 |
| Thr | Gln | Gly | Lys | Pro<br>325 | Ala | Ile | Ala | His | Arg<br>330 | Asp | Leu | Lys | Ser | Lys<br>335 | Asn |
| Ile | Leu | Val | Lys<br>340 | Lys | Asn | Gly | Thr | Cys<br>345 | Cys | Ile | Ala | Asp | Leu<br>350 | Gly | Leu |
| Ala | Val | Arg<br>355 | His | Asp | Ser | Ala | Thr<br>360 | Asp | Thr | Ile | Asp | Ile<br>365 | Ala | Pro | Asn |
| His | Arg<br>370 | Val | Gly | Thr | Lys | Arg<br>375 | Tyr | Met | Ala | Pro | Glu<br>380 | Val | Leu | Asp | Asp |
| Ser<br>385 | Ile | Asn | Met | Lys | His<br>390 | Phe | Glu | Ser | Phe | Lys<br>395 | Arg | Ala | Asp | Ile | Tyr<br>400 |
| Ala | Met | Gly | Leu | Val<br>405 | Phe | Trp | Glu | Ile | Ala<br>410 | Arg | Arg | Cys | Ser | Ile<br>415 | Gly |
| Gly | Ile | His | Glu<br>420 | Asp | Tyr | Gln | Leu | Pro<br>425 | Tyr | Tyr | Asp | Leu | Val<br>430 | Pro | Ser |
| Asp | Pro | Ser<br>435 | Val | Glu | Glu | Met | Arg<br>440 | Lys | Val | Val | Cys | Glu<br>445 | Gln | Lys | Leu |
| Arg | Pro<br>450 | Asn | Ile | Pro | Asn | Arg<br>455 | Trp | Gln | Ser | Cys | Glu<br>460 | Ala | Leu | Arg | Val |
| Met<br>465 | Ala | Lys | Ile | Met | Arg<br>470 | Glu | Cys | Trp | Tyr | Ala<br>475 | Asn | Gly | Ala | Ala | Arg<br>480 |
| Leu | Thr | Ala | Leu | Arg<br>485 | Ile | Lys | Lys | Thr | Leu<br>490 | Ser | Gln | Leu | Ser | Gln<br>495 | Gln |
| Glu | Gly | Ile | Lys | Met<br>500 |     |     |     |     |     |     |     |     |     |     |     |

Other embodiments are within the following claims.

What is claimed is:

1. Isolated DNA comprising a nucleotide sequence encoding a transforming growth factor-beta (TGF-β) type I receptor having the amino acid sequence of a receptor endogenously expressed in a mammalian tissue, wherein said nucleotide sequence hybridizes under high stringency conditions with a 50 nucleotide portion of either strand of misr4 (SEQ ID NO: 4).

2. The isolated DNA of claim 1, wherein said receptor is a human protein.

3. The isolated DNA of claim 1, wherein said receptor is a mouse protein.

4. The isolated DNA of claim 1, wherein said receptor is a rat protein.

5. The isolated DNA of claim 4, wherein said receptor has at least 70% amino acid sequence identity with the amino acid sequence of MISR4 (SEQ ID NO: 17).

6. The isolated DNA of claim 4, wherein said receptor has the amino acid sequence of MISR4 (SEQ ID NO: 17).

7. The isolated DNA of claim 1, wherein said sequence encoding said receptor hybridizes under high stringency conditions with the coding sequence of misr4 (SEQ ID NO: 4).

8. Isolated DNA comprising a nucleotide sequence encoding the receptor encoded by the isolated DNA of claim 1, wherein said receptor is a human TGF-β type I receptor.

9. Isolated DNA comprising a nucleotide sequence encoding the receptor encoded by the isolated DNA of claim 1, wherein said receptor is a rat TGF-β type I receptor.

10. Isolated DNA comprising a nucleotide sequence encoding the receptor encoded by the isolated DNA of claim 1, wherein said receptor is a mouse TGF-β type I receptor.

11. A cell comprising the isolated DNA of claim 1.

12. The cell of claim 8, wherein said cell is capable of expressing said receptor.

13. The cell of claim 11, wherein said cell is a eukaryotic cell.

14. The cell of claim 11, wherein said receptor is a human protein.

15. The isolated DNA of claim 1, wherein said sequence encoding said receptor is under the transcriptional control of a heterologous promoter.

16. A vector comprising the isolated DNA of claim 1.

17. The vector of claim 16, wherein said vector is a viral nucleic acid.

18. The vector of claim 16, wherein said receptor is a human protein.

19. A substantially pure nucleic acid at least 50 nucleotides in length having the nucleotide sequence of a fragment of the isolated DNA of claim 1.

20. The nucleic acid of claim 19, wherein said nucleic acid is incorporated into a vector.

21. The nucleic acid of claim 19, wherein said receptor is a human protein.

* * * * *